United States Patent
Lafont et al.

(10) Patent No.: US 10,316,056 B2
(45) Date of Patent: Jun. 11, 2019

(54) CHEMICAL COMPOUNDS AND USE THEREOF FOR IMPROVING MUSCULAR QUALITY

(71) Applicants: BIOPHYTIS, Paris (FR); UNIVERSITE PARIS 6 PIERRE ET MARIE CURIE, Paris (FR)

(72) Inventors: René Lafont, Paris (FR); Waly Dioh, Bretigny sur Orge (FR); Sophie Raynal, Paris (FR); Stanislas Veillet, Savigny sur Orge (FR); Franck Lepifre, Saclay (FR); Jean-Denis Durand, Montreuil sous Bois (FR)

(73) Assignees: BIOPHYTIS, Paris (FR); SORBONNE UNVERSITÉ, Paris (FR)

( * ) Notice: Subject to any disclaimer, the term of this patent is extended or adjusted under 35 U.S.C. 154(b) by 0 days.

(21) Appl. No.: 15/949,010

(22) Filed: Apr. 9, 2018

(65) Prior Publication Data
US 2018/0327444 A1    Nov. 15, 2018

Related U.S. Application Data

(62) Division of application No. 15/311,967, filed as application No. PCT/FR2015/051332 on May 20, 2015, now Pat. No. 9,938,315.

(30) Foreign Application Priority Data

May 20, 2014    (FR) ..................... 14 54538

(51) Int. Cl.
  C07J 5/00    (2006.01)
  C07J 17/00   (2006.01)
  C07J 31/00   (2006.01)
  C07J 41/00   (2006.01)
  C07J 43/00   (2006.01)

(52) U.S. Cl.
  CPC ........... *C07J 41/005* (2013.01); *C07J 5/0015* (2013.01); *C07J 17/00* (2013.01); *C07J 31/006* (2013.01); *C07J 41/0016* (2013.01); *C07J 41/0055* (2013.01); *C07J 43/003* (2013.01)

(58) Field of Classification Search
  None
  See application file for complete search history.

(56) References Cited

U.S. PATENT DOCUMENTS

2007/0259837 A1   11/2007   Meier et al.
2009/0298175 A1   12/2009   Hormann et al.
2014/0309203 A1   10/2014   Lafont et al.

FOREIGN PATENT DOCUMENTS

WO    2006/007910 A1    1/2006
WO    2009/114201 A2    9/2009
WO    2013/068704 A1    5/2013

OTHER PUBLICATIONS

Kumpun et al., "The metabolism of 20-hydroxyecdysone in mice: Relevance to pharmacological effects and gene switch applications of ecdysteroids," The J. Steroid Biochem. and Molecular Biol., Aug. 1, 2011, pp. 1-9, vol. 126, No. 1-2.
Syrov, "Comparative experimental investigation of the anabolic activity of phytoecdysteroids and steranabols," Pharm. Chem. J., Apr. 1, 2000, pp. 193-197, vol. 34, No. 4.
Toth et al., "20-Hydroxyecdysone increases fiber size in a muscle-specific fashion in rat," Phytomedicine, Sep. 3, 2008, pp. 691-698, vol. 15, No. 9, Gustav Fischer Verlag, Stuttgart, DE.
Kizelsztein et al., 20-Hydroxyecdysone decreases weight and hyperglycemia in a diet-induced obesity mice model, American J. of Physiol.: Endocrinology and Metab., Mar. 1, 2009, pp. E433-E439, vol. 296, No. 3, American Physiological Society, Bethesda, MD, US.
Zhao et al., "Coordinate activation of autophagy and the proteasome pathway by FoxO transcription factor," Autophagy, 2008, pp. 378-380, vol. 4, No. 3.
Little et al. "Resistance exercise and nutrition to counteract muscle wasting," Appl. Physiol. Nutr. Metab., Oct. 2009, pp. 817-828, vol. 34.
Bathori et al., "Complex Phytoecdysteroid Cocktail of Silene otites (*Caryophyllaceae*)," Archives of Insect Biochem. and Physiol., 1999, pp. 1-8, vol. 41.
Communications to the Editor, "Synthesis of Ecdysterone," Chem. Pharm. Bull., 1969, pp. 1970-1973, vol. 17.
Galbraith et al., "The Structure of Podecdysone B, a New Phytoecdysone," Chemical Communications, 1969, pp. 402-403.

*Primary Examiner* — Zinna Northington Davis
(74) *Attorney, Agent, or Firm* — Im IP Law; C. Andrew Im; Chai Im

(57) ABSTRACT

Chemical compounds and the therapeutic use thereof, in particular for improving muscular quality in mammals. More particularly, a method of improving muscular quality in sarcopenic mammals and treating and/or preventing sarcopenia using the chemical compounds and, in particular, sarcopenic obesity and the associated complications and/or pathologies thereof, such as loss of strength, muscle mass, performance and of physical and movement capacity. Also, a method of improving muscle quality in obese mammals and treating and/or preventing of obesity and associated complications and/or pathologies, advantageously type 2 diabetes and metabolic syndrome, using the chemical compounds.

15 Claims, 3 Drawing Sheets
Specification includes a Sequence Listing.

| Compound number | Myostatin gene expression | Myostatin gene expression | Protein synthesis | Protein synthesis | C=X | Y | V-U | Q | R1 |
|---|---|---|---|---|---|---|---|---|---|
| 4 | A | 48% | | 85% | C=O | H | C-C | C=N-OCH2CO2H | Me |
| 5 | A | 41% | | 86% | C=O | H | C-C | C=N-OEt | Me |
| 7 | A | 67% | | | C=N-OMe | Absent | C-C | C=N-OH | Me |
| 21 | A | 44% | | | C=N-OH | alpha-OH | C-C | C=N-OCH2-CH=CMe2 | Me |
| 25 | A | 67% | | 104% | C=O | alpha-OH | C-C | C=N-OMe | Me |
| 27 | A | 59% | | | C=O | alpha-OH | C-C | C=N-O(CH2)2-OPh | Me |
| 28 | A | 56% | A | 194% | C=O | alpha-OH | C-C | C=N-O(CH2)2-CH=CH2 | Me |
| 29 | A | 62% | | 107% | C=O | alpha-OH | C-C | C=N-O(CH2)2-OMe | Me |
| 31 | A | 57% | | 94% | C=O | alpha-OH | C-C | C=N-O(CH2)2-Morpholine | Me |
| 32 | A | 35% | B | 117% | C=O | alpha-OH | C-C | C=N-O(CH2)2-NH2 | Me |
| 33 | A | 48% | | | C=O | Absent | C=C | C=N-O(CH2)2-OPh | Me |
| 38 | A | 35% | | | C=N-OMe | alpha-OH | C-C | CH-N(iPr)-CH2-CH(OMe)2 | Me |
| 41 | A | 59% | B | 121% | C=O | alpha-OH | C-C | CH-N(CO-CH2-OMe)-(CH2)2-OMe | Me |
| 42 | | 100% | A | 136% | C=O | alpha-OH | C-C | CH-NH-(CH2)2-OMe | Me |
| 43 | A | 57% | B | 115% | C=O | alpha-OH | C-C | CH-NH-CH2-(3-Py) | Me |
| 46 | A | 59% | B | 120% | C=O | alpha-OH | C-C | CH-NH-CH2-(2-THF) | Me |
| 47 | A | 57% | | | C=O | alpha-OH | C-C | CH-N(cycloPropyl)-CH2-(2-THF) | Me |
| 51 | A | 51% | B | 124% | C=O | alpha-OH | C-C | CH-N(CO-CHEt2)-(CH2)2-OMe | Me |
| 52 | A | 30% | B | 110% | C=O | alpha-OH | C-C | CH-N(CO-(CH2)2-CH=CH2)-(CH2)2-OMe | Me |
| 53 | A | 59% | | 87% | C=O | alpha-OH | C-C | CH-N(CO-2-Thienyl)-(CH2)2-OMe | Me |
| 54 | A | 70% | | 100% | C=O | alpha-OH | C-C | CH-N(CO-CH2-OMe)-cycloPropyl | Me |
| 62 | A | 58% | A | 134% | C=O | alpha-OH | C-C | CH-N(CO-CH2-OMe)-CH2-(2-THF) | Me |
| 63 | A | 38% | B | 116% | C=O | alpha-OH | C-C | CH-N(CO-2-Furyl)-CH2-(2-THF) | Me |
| 64 | A | 51% | | | C=O | alpha-OH | C-C | CH-N(CO-2-Thienyl)-CH2-CH(OMe)2 | Me |
| 65 | A | 63% | | | C=O | alpha-OH | C-C | CH-N(CO-cycloPropyl)-CH2-CH(OMe)2 | Me |
| 67 | A | 65% | A | 135% | C=O | alpha-OH | C-C | CH-N(CO-2-Furyl)-CH2-CHF2 | Me |
| 68 | A | 69% | | 102% | C=O | alpha-OH | C-C | CH-N(CO-cycloPropyl)-CH2-CHF2 | Me |
| 71 | A | 46% | | | C=O | alpha-OH | C-C | CH-NBoc-CH2-CHF2 | Me |
| 75 | A | 64% | | | C=O | alpha-OH | C-C | CH-N(isopropyl)-(CH2)2-OMe | Me |
| 76 | A | 51% | B | 122% | C=O | alpha-OH | C-C | CH-NMe-(CH2)2-OMe | Me |
| 79 | A | 59% | | | C=O | alpha-OH | C-C | CH-NMe-CH2-CH(OMe)2 | Me |
| 81 | A | 69% | B | 126% | C=O | alpha-OH | C-C | C=O | -CH2-Morpholine |
| 86 | A | 63% | A | 133% | C=O | alpha-OH | C-C | C=O | -CH2-1-(3-HO-Pyrrolid) |
| 88 | B | 78% | B | 122% | C=O | alpha-OH | C-C | C=O | -CH2-1-(4-HO-Piperidine) |
| 89 | A | 57% | A | 151% | C=O | alpha-OH | C-C | C=O | -CH2-1-{4-[HO(CH2)2]-Piperidine} |
| 91 | B | 80% | B | 125% | C=O | alpha-OH | C-C | C=O | -CH2-NMe-(CH2)3-NMe2 |
| 92 | A | 46% | B | 109% | C=O | alpha-OH | C-C | C=O | -CH2-S-CH2-CO2Et |
| 93 | A | 40% | A | 132% | C=O | alpha-OH | C-C | C=O | -CH2-SEt |
| 94 | A | 68% | A | 137% | C=O | alpha-OH | C-C | C=O | -CH2-S-(CH2)2-OH |
| 99 | A | 66% | | | C=O | alpha-OH | C-C | CH-OH | -CH2-1-{4-[HO(CH2)2]-Piperidine} |
| 101 | A | 65% | | | C=N-OMe | alpha-OH | C-C | C=N-OMe | -CH2-Morpholine |

Fig.6

SEQUENCE LISTING

<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Mus musculus/homo sapiens/Rattus norvegicus

```
<400> SEQUENCE: 1
gagtctgact ttctaatgca ag                                          22

<210> SEQ ID NO 2
<211> LENGTH: 20
<212> TYPE: DNA
<213> ORGANISM: Artificial Sequence
<220> FEATURE:
<223> OTHER INFORMATION: Mus musculus/homo sapiens/Rattus norvegicus

<400> SEQUENCE: 2
tgttgtagga gtcttgacgg                                             20

<210> SEQ ID NO 3
<211> LENGTH: 20
<212> TYPE: DNA
<213> ORGANISM: Artificial Sequence
<220> FEATURE:
<223> OTHER INFORMATION: Mus musculus/homo sapiens/Rattus norvegicus

<400> SEQUENCE: 3
agagtcggca agtctgtgct                                             20

<210> SEQ ID NO 4
<211> LENGTH: 19
<212> TYPE: DNA
<213> ORGANISM: Artificial Sequence
<220> FEATURE:
<223> OTHER INFORMATION: Mus musculus/homo sapiens/Rattus norvegicus

<400> SEQUENCE: 4
gtgaggcctt tgaaggcag                                              19

<210> SEQ ID NO 5
<211> LENGTH: 20
<212> TYPE: DNA
<213> ORGANISM: Mus musculus

<400> SEQUENCE: 5
ctctagactt cgagcaggag                                             20

<210> SEQ ID NO 6
<211> LENGTH: 19
<212> TYPE: DNA
<213> ORGANISM: Mus musculus

<400> SEQUENCE: 6
ggtaccacca gacagcact                                              19
```

CHEMICAL COMPOUNDS AND USE THEREOF FOR IMPROVING MUSCULAR QUALITY

RELATED APPLICATION

This application is a divisional of application Ser. No. 15/311,967 filed Jan. 3, 2017, which is a § 371 application from PCT/FR2015/051332 filed May 20, 2015, which claims priority from French Patent Application No. 14 54538 filed May 20, 2014, each of which is herein incorporated by reference in its entirety.

REFERENCE TO ELECTRONIC SEQUENCE

The contents of the electronic sequence listing (seq.txt; Size: 1.41 kilobytes; and Date of Creation: Apr. 9, 2018) is herein incorporate by reference in its entirety.

FIELD OF THE INVENTION

The present invention relates to chemical compounds and to the therapeutic use thereof, in particular for improving muscle quality in mammals.

More particularly, the invention makes it possible to improve muscle quality in obese mammals.

The invention also makes it possible to improve the muscle quality of sarcopenic mammals.

The invention also relates to the use of these chemical compounds in the treatment and/or prevention of obesity in mammals.

BACKGROUND OF THE INVENTION

Muscle atrophy can result from several different causes: under nutrition, non-use of the muscles (for example immobilization following a fracture), cancer or other serious disease (heart or kidney failure) inducing cachexia, or resulting naturally from the aging of individuals (sarcopenia). This atrophy can result from a reduction in protein synthesis and/or from an increase in proteolysis and, as appropriate, is accompanied by fibrosis and/or by infiltration by adipose tissue. The identification of the factors and mechanisms controlling muscle protein synthesis and muscle proteolysis thus represents a prerequisite for designing appropriate treatments for these pathological conditions.

FIG. 1, which is part of the prior art, shows the principal pathways of protein synthesis and proteolysis in muscles (reconstructed according to Zhao et al., 2008 and Little et al., 2009).

Muscle protein synthesis is essential, and is essentially controlled at the translational level. It requires of course an adequate nutritional intake of amino acids. It is stimulated by physical activity and regulated by numerous factors, at the forefront of which are IGF-1 and androgens (Little et al., 2009).

TABLE 1 factors and molecules which act on protein synthesis and proteolysis in muscles

| Factor | Protein synthesis | | Proteolysis | |
| --- | --- | --- | --- | --- |
| | Stimulation | Inhibition | Stimulation | Inhibition |
| Exercise | + | | (+) | |
| Denervation | | − | | |
| Fasting, anorexia | | − | + | |
| Amino acids | + | | | − |
| Insulin | + | | | − |
| GH/IGF-1 | + | | | − |
| FGF | + | | + | |
| Vitamin D | + | | | |
| Adrenaline | + | | | − |
| Acetylcholine | | | | − |
| Ocytocine | + | | | |
| Apelin | + | | | |
| Testosterone | + | | | − |
| Estradiol | + | | | − |
| Triiodothyronine (T3) | + | | | |
| Myostatin | | − | + | |
| TGFβ | | − | + | |
| Follistatin | | | | − |
| Angiotensin II | | − | + | |
| Angiotensin-(1-7) | | | | − |
| Glucocorticoids | | − | + | |
| PIF | | − | + | |
| IL-1β | | | + | |
| IL-6 | | (−) | + | |
| TNF-α, IFN-γ | | − | + | |
| Anti-inflammatories | | | | − |

Myofibril proteolysis is performed via the proteasome, while the mitochondria are destroyed by autophagy (Zhao et al., 2008). Satellite cell apoptosis mechanisms are also described (Murphy et al., 2010).

Myostatin, produced in an autocrine manner by the muscles themselves, represents a particularly important factor, since it acts both by stimulating proteolysis and by inhibiting protein synthesis. It also stimulates fibrosis (Li et al., 2008).

Aging is accompanied by a modification of the various regulatory factors (Walston et al., 2012): physical activity is often reduced, protein/vitamin nutrition may be insufficient and, following meals, the contents of circulating amino acids, an increase of which is required to stimulate protein synthesis, show a reduced increase that may be due to splanchnic sequestration (Boirie et al., 1997). Moreover, aging is accompanied by considerable hormonal modifications: an increase in myostatin (Leger et al., 2008), a reduction in androgens (Seidman, 2007) and in growth hormone (Macell et al., 2001; Sattler, 2013), and also an increase in inflammation markers (IL-6, TNF-α etc., Schaap et al., 2009; Verghese et al., 2011), will in particular be noted. These various modifications are unfavorable for protein synthesis, whereas these promote proteolysis, hence the gradual reduction in muscle size (sarcopenia). They also cause a modification in the distribution of muscle fiber types to the detriment of the fast fibers, which is reflected by a decrease in muscle strength (dynapenia). Finally, the development of connective tissue within the muscles (fibrosis) is witnessed.

In an obesity context, the situation is worsened for several additional reasons: fat infiltration of the muscles worsens the inflammatory context, insulin resistance reduces the effect of IGF-1 on protein synthesis, without considering that mobility is reduced by the excess weight (Stenholm et al., 2009).

FIG. 2, which is part of the prior art, illustrates the worsening of sarcopenia in an obesity context (according to Quillot et al., 2013).

In any event, in the absence of treatment, sarcopenia is a process which can only get worse, until total loss of mobility. However, sarcopenia is not the only process which results in skeletal muscle atrophy. Atrophy also occurs during immobilization (for example following a fracture), during prolonged fasting (or a slimming diet), or during serious pathological conditions (for example cancers, AIDS) which cause cachexia.

Mention may also be made of various muscle dystrophies of genetic origin. These various situations have a certain number of characteristics in common with sarcopenia, but with a respective weight different than the triggering factors (Tisdale, 2007; Saini et al., 2009).

Known Possible Treatments

Various methods for preventing/treating sarcopenia have thus been envisaged and tested. They are first and foremost physical exercise, the effectiveness of which is established (Bonnefoy et al, 2000; Bonnefoy, 2008; Ryan et al., 2013). Thus, following exercise carried out over a period of 8 weeks, increases in muscle strength of 180% and in muscle mass of 11% have been observed (Fiatarone et al., 1990). However, optimal effectiveness would require several hours of physical exercise per day, which is difficult to envision over long periods of time.

An increased intake of protein synthesis substrates, whether by giving rapidly digestive proteins according to an optimized timing (Coëffier et al., 2009; Aussel et al., 2013), and also a supplement of certain amino acids or their metabolites (leucine, HMB [β-hydroxy-β-methylbutyrate], citrulline, ornithine), can increase muscle protein synthesis (Li & Heber, 2011).

Various pharmaceutical treatments aim to correct the modifications of the hormonal context associated with aging (Crenn, 2013). They comprise:

- sex hormones such as testosterone (White et al., 2013) or variants thereof, SARMs (Selective Androgen Receptor Modulators), or non-sex hormones such as growth hormone (Liu et al., 2003) and IGF-1, ghrelin or progranulin, or even vitamin D;
- myostatin inhibitors (antibodies directed against the molecule or its receptor, or myostatin precursor peptide) (Murphy et al., 2010; Han & Mitch, 2011);
- molecules which target the renin-angiotensin system, such as inhibitors of ACE or angiotensin 1-7 (Dalla Libera et al., 2001; Shiuchi et al., 2004; Kalupahana & Moustaid-Moussa, 2012; Allen et al., 2013);
- β-adrenergic receptor agonists (Ryall et al., 2004, 2007);
- varied natural substances, or even more complex extracts of plant origin (for example, isoflavones: Aubertin-Leheudre et al., 2007; olive oil extract: Pierno et al., 2014; resveratrol: Shadfar et al., 2011; Bennett et al., 2013).

The great diversity of these treatments attests to the difficulty of treating a multifactorial pathological condition, the triggering factors of which have not been totally identified. Furthermore, several candidate molecules have side effects (in the case of sex hormones, SARMs or β-agonists, for example), or have as yet been studied only on animal models. All these elements explain the lack of available medicaments on the market.

To date, research studies target more particularly myostatin, by inhibiting its action with, for example, anti-myostatin antibodies or anti-receptor antibodies (Dumonceaux et al., 2010; Greenberg, 2012; Sakuma & Yamaguchi, 2012; Arounleut et al., 2013; Buehring & Binkley, 2013; Collins-Hooper et al., 2014; White & Le Brasseur, 2014).

Phytoecdysones, and more particularly the 20-hydroxyecdysone (20E), have been the subject of numerous pharmacological studies, which began in Japan and then in Uzbekistan, and have subsequently developed in various other countries.

These studies have revealed the antidiabetic and anabolic properties of this molecule. Its stimulating effects on protein syntheses in muscles are observed in rats in vivo (Syrov, 2000; Tóth et al., 2008; Lawrence, 2012) and on C2C12 murine myotubes in vitro (Gorelick-Feldman et al., 2008). It is an effect at the level of translation, which involves the phosphorylation of the p70S6K ribosomal protein, at the end of a cascade involving the Akt/PkB protein kinase, a pathway also used by IGF-1 to stimulate protein synthesis.

Using the same C2C12 cells, Zubeldia et al. (2012) have moreover shown that an *Ajuga turkestanica* extract enriched with phytoecdysones (20-hydroxyecdysone and turkesterone) inhibits the transcription of myostatin and of caspase 3 (a protein involved in apoptosis processes).

Moreover, 20-hydroxyecdysone has antifibrotic properties, which have not been demonstrated on muscles, but in the kidneys, where the fibrosis mechanisms take place very similarly (Hung et al., 2012). It thus opposes the effects of TGFβ, a protein similar to myostatin, and in particular the stimulation of Smad 2,3 caused by this substance. It can thus be considered that 20-hydroxyecdysone could have similar effects on muscles (or the heart).

20-Hydroxyecdysone reduces body fat in mice fed with a fat-enriched diet (Kizelsztein et al., 2009; Foucault et al., 2012) or in ovariectomized female rats, a model of menopause (Seidlova-Wuttke et al., 2010).

Some of the effects described above in animal models have been found in clinical studies, which are even fewer in number. Thus, 20-hydroxyecdysone increases physical capacity (Azizov et al., 1995; Gadhzieva et al., 1995) and muscle mass (Simakin et al., 1988) and causes a loss of abdominal fat mass in obese and overweight volunteers (Wuttke et al., 2013; Foucault et al., 2014; PCT patent application WO 2013/068704).

However, 20E and the metabolites thereof have poor bioavailability in mice (Dzhukharova et al., 1987; Hikino et al., 1972), in rats (Kapur et al., 2010 and Seidlova-Wuttke et al., 2010) and in humans (Brandt 2003; Bolduc, 2006). Their overall performance is among other things not entirely satisfactory in relation to muscle quality improvement applications.

Several studies have shown that turkesterone (11α,20-dihydroxyecdysone), a metabolite derived from 20E, shows a greater activity than that of 20E in vivo (Syrov et al., 2001: Bathori et al., 2008). There is still today, for therapeutic applications targeting an improvement in muscle quality both in obese mammals and in sarcopenic mammals, a need for novel compounds which have good bioavailability, expressed more particularly in terms of high plasma exposure coefficient, while at the same time having an overall activity greater than that of 20E on muscle quality improvement, this overall activity being expressed in terms of performance relating to inhibition of myostatin gene expression combined with increased protein synthesis in the mammal.

SUMMARY OF THE INVENTION

The inventors have now discovered that, entirely unexpectedly, certain compounds of the steroid family corresponding to a particular general formula, the structure of which differs from that of 20E and metabolites thereof, have a plasma exposure coefficient that is higher than that of said 20E and effects that are greater than or equal to those of 20-hydroxyecdysone (20E) with respect to the inhibition of myostatin and the stimulation of protein synthesis via phosphorylation of the S6K1 protein. These effects make it possible to improve the muscle quality and/or strength in sarcopenic mammals and sarcopenic obese mammals.

The compounds of the invention do not interact with steroid nuclear receptors of the sex sphere (androgen receptors and estrogen receptors). They show good chemical stability in plasma and in microsomes. Finally, several of them have a pharmacokinetic profile that is much improved compared with 20-hydroxyecdysone. They also induce better inhibition of myostatin gene expression and a better improvement of protein synthesis.

The invention thus provides a compound of general formula (I) below:

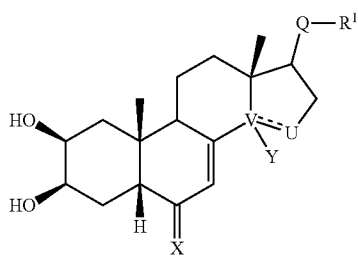

(I)

wherein:

V-U is a carbon-carbon single bond and Y is a hydroxyl group or a hydrogen, or V—U is a C=C ethylenic bond;

X is chosen from: an oxygen; an N—$OR^5$ group, $R^5$ then being chosen from: a hydrogen; a $C_1$-$C_6$ alkyl group optionally having unsaturations on the chain; a $(C_1$-$C_6)CO_2R^6$ group with $R^6$ possibly being a hydrogen or a $C_1$-$C_6$ group; a $(C_1$-$C_6)OR^7$ group, $R^7$ being an aromatic or heteroaromatic ring optionally monosubstituted or polysubstituted with an alkyl or alkoxyl group, $CF_3$, Cl; a $(C_1$-$C_6)NR^8R^9$ group, $R^8$ and $R^9$ being $C_1$-$C_6$ groups, or $(C_1$-$C_6)N(C_1$-$C_6)$ groups or $(C_1$-$C_6)N(C_1$-$C_6)OR^6$ groups with $R^6$ as defined above, $NR^8R^9$ can also be a heterocycle; and wherein:

Q is a carbonyl group;
with $R^1$ being chosen from: a $(C_1$-$C_6)W(C_1$-$C_6)$ group; a $(C_1$-$C_6)W(C_1$-$C_6)W(C_1$-$C_6)$ group; a $(C_1$-$C_6)W(C_1$-$C_6)CO_2(C_1$-$C_6)$ group; a $(C_1$-$C_6)A$ group, A representing a heterocycle optionally substituted with a group of the type OH, OMe, $(C_1$-$C_6)$, $N(C_1$-$C_6)$ or $CO_2(C_1$-$C_6)$; a $CH_2Br$ group;

W being a heteroatom chosen from N, O and S;

or,

Q is a CHOH group;
with $R^1$ being chosen from: a $(C_1$-$C_6)W(C_1$-$C_6)$ group; a $(C_1$-$C_6)W(C_1$-$C_6)W(C_1$-$C_6)$ group; a $(C_1$-$C_6)W(C_1$-$C_6)CO_2(C_1$-$C_6)$ group;

W being a heteroatom chosen from N and S;

or,

Q is chosen from: a C=$NOR^5$ group, $R^5$ being defined as above; a $CHNR^2R^3$ group,
with $R^1$ being a $(C_1$-$C_6)$ alkyl group;
with $R^2$ and $R^3$, which may be identical or different, each chosen from: a hydrogen atom; a $(C_1$-$C_6)$ alkyl group; a $(C_1$-$C_6)W(C_1$-$C_6)$ group; a cycloalkyl group; a $(C_1$-$C_6)CHF_2$ group; a $(C_1$-$C_6)A$ group with A representing a heterocycle defined as above; a group of $COR^4$ type, $R^4$ being chosen from: an optionally unsaturated $(C_1$-$C_6)$ alkyl or cycloalkyl group; a heterocyclic group of A type as defined above, an aromatic or heteroaromatic group optionally substituted with a group of the type OH, OMe, $(C_1$-$C_6)$, $N(C_1$-$C_6)$, $CO_2(C_1$-$C_6)$, $CF_3$, $OCF_3$, CN, Cl, F; a $(C_1$-$C_6)W(C_1$-$C_6)$ group;

W being a heteroatom chosen from N, O and S;

the compound being in the form of an enantiomer, a diastereoisomer, a hydrate, a solvate, a tautomer, a racemic mixture or a pharmaceutically acceptable salt.

Another particular form of the invention uses the compound of general formula (I) mentioned above wherein Q represents a carbonyl group.

One particular form of the invention uses the compound of general formula (I), wherein:

X is an oxygen;
V—U is a carbon-carbon single bond;
Y is a hydroxyl group;
Q is a carbonyl group;
$R^1$ is chosen from: a $(C_1$-$C_6)W(C_1$-$C_6)$ group; a $(C_1$-$C_6)W(C_1$-$C_6)W(C_1$-$C_6)$ group; a $(C_1$-$C_6)W(C_1$-$C_6)CO_2(C_1$-$C_6)$ group; a $(C_1$-$C_6)A$ group, A representing a heterocycle optionally substituted with a group of the type OH, OMe, $(C_1$-$C_6)$, $N(C_1$-$C_6)$ or $CO_2(C_1$-$C_6)$;

W being a heteroatom chosen from N, O and S.

Another particular form of the invention uses the compound of general formula (I), wherein Q represents a $CHNR^2R^3$ group, with $R^2$ and $R^3$ being chosen from: a hydrogen atom; a $(C_1$-$C_6)$ alkyl group; a $(C_1$-$C_6)W(C_1$-$C_6)$ group; a cycloalkyl group; a $(C_1$-$C_6)CHF_2$ group; a $(C_1$-$C_6)A$ group, with A representing a heterocycle defined as above; a group of $COR^4$ type, $R^4$ being chosen from: an optionally unsaturated $(C_1$-$C_6)$ alkyl or cycloalkyl group; a heterocyclic group of A type as defined above, an aromatic or heteroaromatic group optionally substituted with a group of the type OH, OMe, $(C_1$-$C_6)$, $N(C_1$-$C_6)$, $CO_2(C_1$-$C_6)$, $CF_3$, $OCF_3$, CN, Cl, F; a $(C_1$-$C_6)W(C_1$-$C_6)$ group.

Another particular form of the invention uses the compound of general formula (I), wherein:

X is an oxygen;
V—U is a carbon-carbon single bond;
Y is a hydroxyl group;
$R^1$ is a methyl group;
Q is a $CHNR^2R^3$ group;
with $R^2$ and $R^3$ being chosen from: a hydrogen atom; a $(C_1$-$C_6)$ alkyl group; a $(C_1$-$C_6)W(C_1$-$C_6)$ group; a cycloalkyl group; a $(C_1$-$C_6)CHF_2$ group; a $(C_1$-$C_6)A$ group, with A representing a heterocycle defined as above; a group of $COR^4$ type, $R^4$ being chosen from: an optionally unsaturated $(C_1$-$C_6)$ alkyl or cycloalkyl group; a heterocyclic group of A type as defined above, an aromatic or heteroaromatic group optionally substituted with a group of the type OH, OMe, $(C_1$-$C_6)$, $N(C_1$-$C_6)$, $CO_2(C_1$-$C_6)$, $CF_3$, $OCF_3$, CN, Cl, F; a $(C_1$-$C_6)W(C_1$-$C_6)$ group;

W being an heteroatom chosen from N, O and S.

Another particular form of the invention uses the compound of general formula (I), wherein Q represents a C=$NOR^5$ group, $R^5$ being defined as above.

Another particular form of the invention uses the compound of general formula (I), wherein:

X is an oxygen;
V—U is a carbon-carbon single bond;
Y is a hydroxyl group;
$R^1$ is a methyl group;
Q is a C=$NOR^5$ group, $R^5$ being defined as above.

Another particular form of the invention uses the compound of general formula (I), wherein V—U is a C=C ethylenic bond.

Another particular form of the invention uses the compound of general formula (I), wherein X is an N—$OR^5$ group, $R^5$ being defined as above.

Another particular form of the invention uses the compound of general formula (I), chosen from the following compounds:

No. 28: (2S,3R,5R,10R,13R,14S,17S)-17-(N-but-3-enoxy-C-methyl-carbonimidoyl)-2,3,14-trihydroxy-10,13-dimethyl-2,3,4,5,9,11,12,15,16,17-decahydro-1H-cyclopenta[a]phenanthren-6-one No. 32: (2S,3R,5R,10R,13R,14S,17S)-17-(N-(2-diethylaminoethoxy)-C-methyl-carbonimidoyl)-2,3,14-trihydroxy-10,13-dimethyl-2,3,4,5,9,11,12,15,16,17-decahydro-1H-cyclopenta[a]phenanthren-6-one No. 41: 2-methoxy-N-(2-methoxyethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]acetamide No. 42: (2S,3R,5R,10R,13R,14S,17S)-2,3,14-trihydroxy-17-[1-(2-methoxyethylamino)ethyl]-10,13-dimethyl-2,3,4,5,9,11,12,15,16,17-decahydro-1H-cyclopenta[a]phenanthren-6-one No. 43: (2S,3R,5R,10R,13R,14S,17S)-2,3,14-trihydroxy-10,13-dimethyl-17-[1-(3-pyridylmethylamino)ethyl]-2,3,4,5,9,11,12,15,16,17-decahydro-1H-cyclopenta[a]phenanthren-6-one No. 46: (2S,3R,5R,10R,13R,14S,17S)-2,3,14-trihydroxy-10,13-dimethyl-17-[1-(tetrahydrofuran-2-ylmethylamino)ethyl]-2,3,4,5,9,11,12,15,16,17-decahydro-1H-cyclopenta[a]phenanthren-6-one No. 51: 2-ethyl-N-(2-methoxyethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]butanamide No. 62: 2-methoxy-N-(tetrahydrofuran-2-ylmethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]acetamide No. 63: N-(tetratetrahydrofuran-2-ylmethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]furan-2-carboxamide No. 67: N-(2,2-difluoroethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]furan-2-carboxamide No. 76: (2S,3R,5R,10R,13R,14S,17S)-2,3,14-trihydroxy-17-[1-(2-methoxyethyl(methyl)amino)ethyl]-10,13-dimethyl-2,3,4,5,9,11,12,15,16,17-decahydro-1H-cyclopenta[a]phenanthren-6-one No. 81: (2S,3R,5R,10R,13R,14S,17S)-2,3,14-trihydroxy-10,13-dimethyl-17-(2-morpholinoacetyl)-2,3,4,5,9,11,12,15,16,17-decahydro-1H-cyclopenta[a]phenanthren-6-one No. 86: (2S,3R,5R,10R,13R,14S,17S)-2,3,14-trihydroxy-17-[2-(3-hydroxypyrrolidin-1-yl)acetyl]-10,13-dimethyl-2,3,4,5,9,11,12,15,16,17-decahydro-1H-cyclopenta[a]phenanthren-6-one No. 88: (2S,3R,5R,10R,13R,14S,17S)-2,3,14-trihydroxy-17-[2-(4-hydroxy-1-piperidypacetyl]-10,13-dimethyl-2,3,4,5,9,11,12,15,16,17-decahydro-1H-cyclopenta[a]phenanthren-6-one No. 89: (2S,3R,5R,10R,13R,14S,17S)-2,3,14-trihydroxy-17-[2-[4-(2-hydroxyethyl)-1-piperidyl]acetyl]-10,13-dimethyl-2,3,4,5,9,11,12,15,16,17-decahydro-1H-cyclopenta[a]phenanthren-6-one No. 91: (2S,3R,5R,10R,13R,14S,17S)-17-[2-(3-dimethylaminopropyl(methyl)amino)acetyl]-2,3,14-trihydroxy-10,13-dimethyl-2,3,4,5,9,11,12,15,16,17-decahydro-1H-cyclopenta[a]phenanthren-6-one No. 92: 2-[2-oxo-2-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]sulfanylacetate ethyl No. 93: (2S,3R,5R,10R,13R,14S,17S)-17-(2-ethylsulfanylacetyl)-2,3,14-trihydroxy-10,13-dimethyl-2,3,4,5,9,11,12,15,16,17-decahydro-1H-cyclopenta[a]phenanthren-6-one No. 94: (2S,3R,5R,10R,13R,14S,17S)-2,3,14-trihydroxy-17-[2-(2-hydroxyethylsulfanyl)acetyl]-10,13-dimethyl-2,3,4,5,9,11,12,15,16,17-decahydro-1H-cyclopenta[a]phenanthren-6-one.

Another subject of the invention relates to the use of a compound of general formula (I) as a medicament, in particular in a pharmaceutically acceptable carrier.

Another subject of the invention uses the compound of general formula (I), for use in the treatment and/or prevention of sarcopenia and of sarcopenic obesity, and the associated complications and/or pathological conditions thereof, such as loss of strength, of muscle mass, of physical performance and capacity and of mobility in mammals. The physical performance and capacity can be characterized by means of walking tests and physical effort tests.

Another subject of the invention uses the compound of general formula (I), for use in the treatment and/or prevention of obesity and the complications thereof and/or of the associated pathological conditions, advantageously type 2 diabetes or metabolic syndrome in mammals.

BRIEF DESCRIPTION OF THE DRAWINGS

FIG. 6 illustrates, in the form of a table, the results obtained for compounds of the present invention during experiments in which myostatin gene expression and protein synthesis were analyzed.

DETAILED DESCRIPTION

Figure 1:
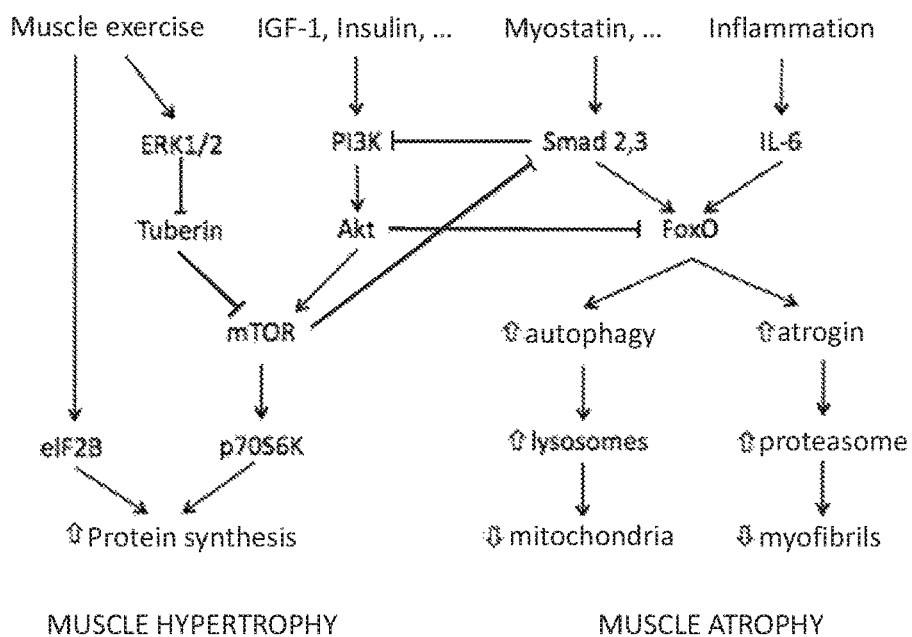
FIG. 1, which is part of the prior art, illustrates the principal pathways of protein synthesis and proteolysis in muscles (constructed according to Zhao et al., 2008 and Little et al., 2009).
Figure 2:
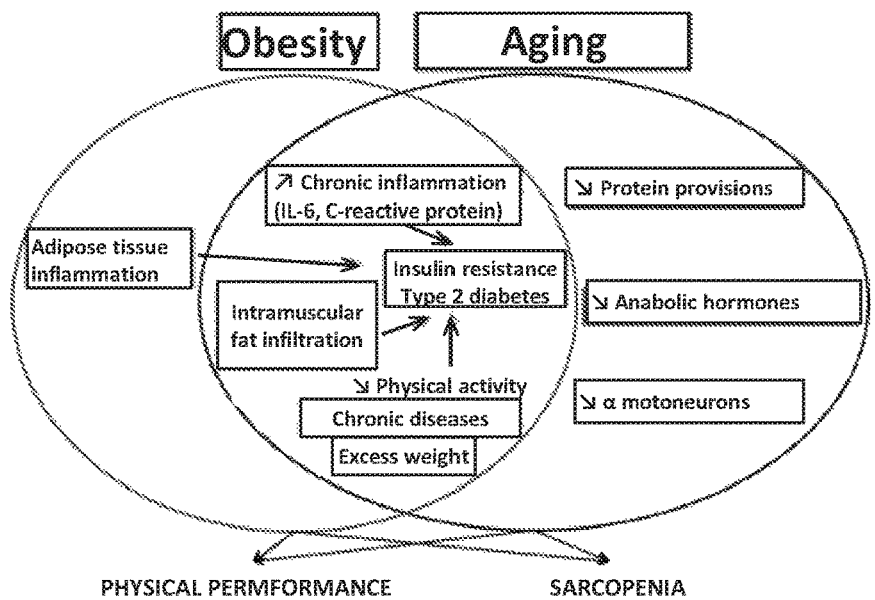
FIG. 2, which is part of the prior art, illustrates the worsening of sarcopenia in an obesity context (according to Quillot et al., 2013).

The object of the invention is to develop novel chemical compounds which meet in particular the objectives set above, in relation to therapeutic applications for the treatment and/or prevention of obesity and/or of sarcopenia in mammals. The latter compounds are novel since they do not exist in the chemical databases. They can advantageously be synthesized according to industrializable processes, that is to say processes with a minimum number of synthesis steps and an optimal yield. They have effects greater than those of 20E in terms of the inhibition of myostatin and the stimulation of protein synthesis via the phosphorylation of the S6K1 protein. They show good chemical stability in plasma and in microsomes. They have an improved pharmacokinetic profile and a defined dosage regimen. They stimulate muscle anabolism in C2C12 cells and show an anti-hyperglycemic effect.

In the context of the present invention, the term "aryl group" is intended to mean an aromatic ring having 5 to 8 carbon atoms or several fused aromatic rings having 5 to 14 carbon atoms. In particular, the aryl groups can be monocyclic or bicyclic groups, preferably phenyl or naphthyl. Advantageously, it is a phenyl group (Ph).

In the context of the present invention, the term "heteroaryl group" is intended to mean any hydrocarbon-based aromatic group of 3 to 9 atoms containing one or more heteroatoms, such as for example sulfur, nitrogen or oxygen atoms. The heteroaryl according to the present invention may consist of one or more fused rings. Examples of a heteroaryl group are furyl, isoxazyl, pyridyl, thiazolyl, pyrimidyl, benzimidazol, benzoxazole and benzothiazole groups. Advantageously, the heteroaryl group is chosen from furyl, pyridyl and thiazolyl groups. Advantageously, it is the furyl group.

In the context of the present invention, the term "halogen atom" is intended to mean any halogen atom, advantageously chosen from Cl, Br, I or F, in particular chosen from F, Cl or Br, in particular F or Cl.

In the context of the present invention, the term "$C_1$-$C_6$ alkyl group" is intended to mean any linear or branched alkyl group having from 1 to 6 carbon atoms, in particular methyl, ethyl, n-propyl, isopropyl, n-butyl, isobutyl, sec-butyl, t-butyl, n-pentyl or n-hexyl groups. Advantageously, it is a methyl, ethyl, isopropyl or t-butyl group, in particular a methyl or ethyl group, more particularly a methyl group.

In the context of the present invention, the term "$C_3$-$C_6$ cycloalkyl group" is intended to mean any saturated and hydrocarbon-based ring comprising from 3 to 6 carbon atoms, in particular the cyclopropyl, cyclobutyl, cyclopentyl or cyclohexyl group. Advantageously, it is a cyclopropyl or cyclohexyl group.

In the context of the present invention, the term "($C_1$-$C_6$ alkyl group) aryl" is intended to mean any aryl group as defined above, bonded by means of a $C_1$-$C_6$ alkyl group as defined above. In particular, an example of a ($C_1$-$C_6$ alkyl group) aryl is a benzyl or —$(CH_2)_2$ phenyl group.

In the context of the present invention, the term "pharmaceutically acceptable" is intended to mean what is of use in the preparation of a pharmaceutical composition which is generally safe, nontoxic and neither biologically undesirable or undesirable in another way, and which is acceptable for both veterinary use and human pharmaceutical use.

In the context of the present invention, the term "pharmaceutically acceptable salts of a compound" is intended to mean salts which are pharmaceutically acceptable, as defined herein, and which have the desired pharmacological activity of the parent compound. Such salts comprise:

(1) the acid addition salts formed with inorganic acids such as hydrochloric acid, hydrobromic acid, sulfuric acid, nitric acid, phosphoric acid and the like; or formed with organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionoic acid, salicylic acid, succinic acid, dibenzoyl-L-tartaric acid, tartaric acid, p-toluenesulfonic acid, trimethylacetic acid, trifluoroacetic acid and the like; or (2) the salts formed when an acid proton present in the parent compound is either replaced with a metal ion, for example an alkali metal ion, an alkaline-earth metal ion or an aluminum ion; or coordinates with an organic or inorganic base. The acceptable organic bases comprise diethanolamine, ethanolamine, N-methylglucamine, triethanolamine, tromethamine and the like. The acceptable inorganic bases comprise aluminum hydroxide, calcium hydroxide, potassium hydroxide, sodium carbonate and sodium hydroxide.

In the context of the present invention, the term "solvate of a compound" is intended to mean any compound obtained by addition of an inert solvent molecule to the compound according to the invention, the solvate forming because of their mutual attraction force. The solvates are, for example, alkoxides of the compound. A hydrate is a solvate in which the inert solvent used is water. It may be mono-, di- or trihydrated.

In the context of the present invention, the term "tautomer" is intended to mean any constitutional isomer of the compounds according to the present invention which are interconvertible by means of the reversible chemical reaction known as tautomerization. In most cases, the reaction occurs by migration of a hydrogen atom accompanied by a change in location of a double bond. In a solution of a compound capable of tautomerization, an equilibrium between the two tautomers is created. The ratio between tautomers then depends on the solvent, on the temperature and on the pH. Tautomerism is thus the conversion of one functional group into another, usually by concomitant shift of a hydrogen atom and of a π bond (double or triple bond). Common tautomers are, for example, the following pairs: aldehydes/ketones—alcohols or more specifically enol; amides—imidic acids; lactams—lactims; imines—enamines; enamines—enamines. In particular, it may include a ring-chain tautomerism which takes place when the movement of the proton is accompanied by the conversion of an open structure to a ring.

Description of the General Syntheses and Schemes

The compounds of general formula (I) can be prepared by applying or adapting any method known per se to those skilled in the art and/or within the scope of the latter, in particular those described by Larock (1989), or by applying or adapting the processes described in the procedures which follow.

The various groups refer to the definitions given above.

Scheme A: The 20-hydroxyecdysone $A_1$ can be reduced to the compound $A_2$ by the action of zinc in acetic acid as described in Zhu et al. (2002). This compound $A_2$ can undergo oxidative cleavage at C20-C22 of the chain by reaction of PCC in pyridine to give the compound $A_3$. The alkyloximes of $R^5ONH_2$ type react with the carbonyl at C20 to give the corresponding imines $A_4$ and also the compound $A_5$ from double reaction at C20 and C6.

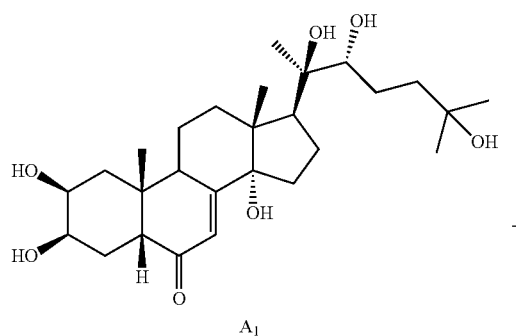

$A_1$

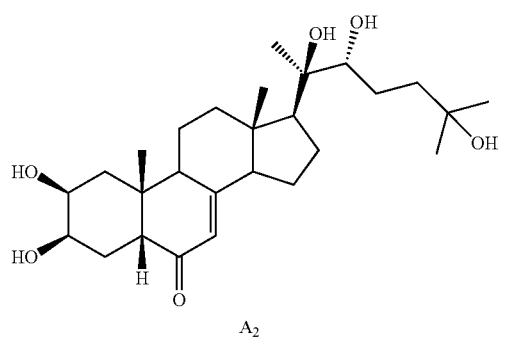

$A_2$

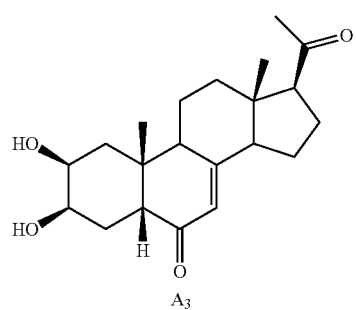

$A_3$

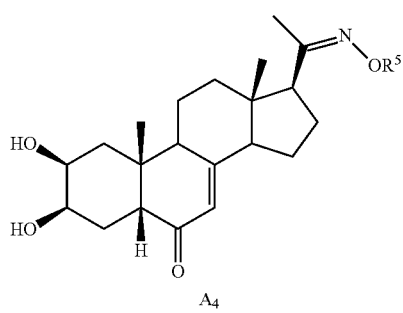

$A_4$

+

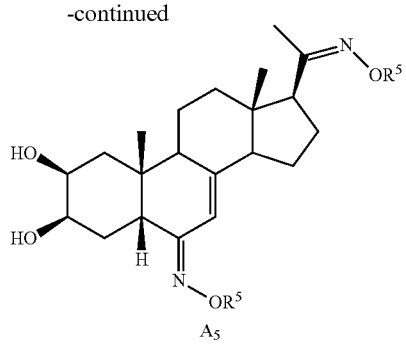

$A_5$

Scheme B: The alkyloximes of $R^5ONH_2$ type react with the carbonyl at C6 of the compound $A_1$ to give the oxime $B_1$ and also, optionally, the compounds $B_2$ (Z conformer) and $B'_2$ (E conformer) from elimination of the hydroxyl at C14-C15. These 3 compounds can independently undergo a chain cleavage as described in scheme A so as to give the compounds $B_3$ and $B_4$, with the (Z)-oxime compound $B'_3$ as by-product. Alkyloximes of $R^5ONH_2$ type react with the carbonyl at C6 of the compounds $B_3$ or $B_4$ to give the compounds $B_5$ and $B_6$.

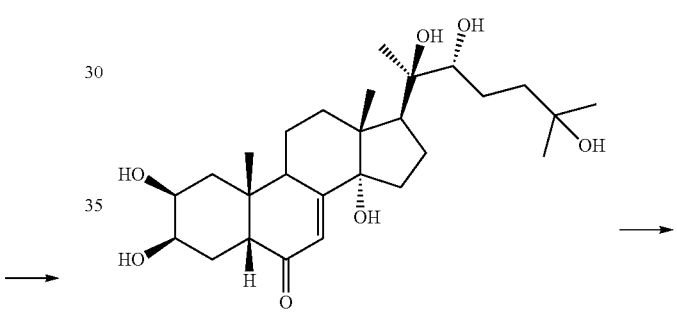

$A_1$

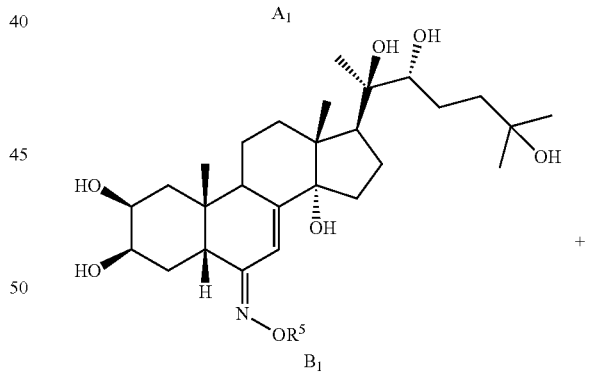

$B_1$

+

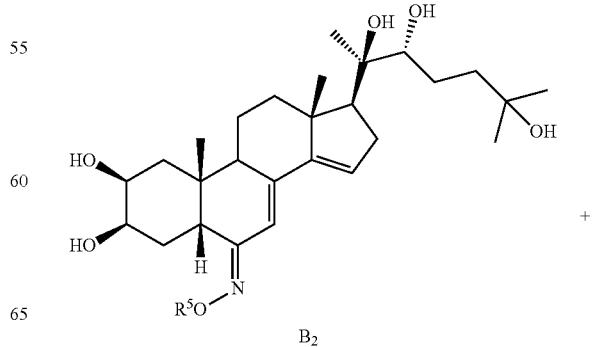

$B_2$

+

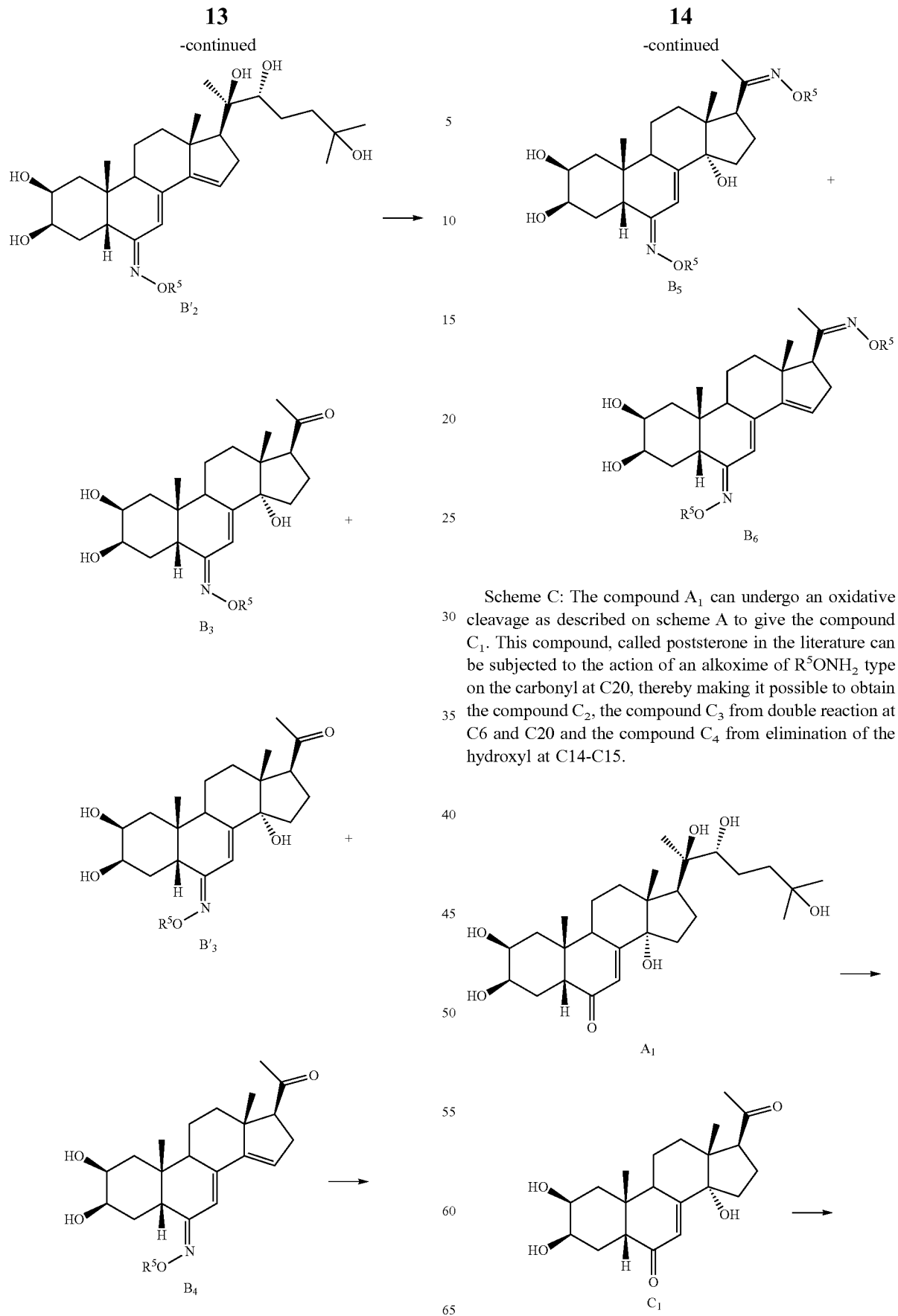

Scheme C: The compound $A_1$ can undergo an oxidative cleavage as described on scheme A to give the compound $C_1$. This compound, called poststerone in the literature can be subjected to the action of an alkoxime of $R^5ONH_2$ type on the carbonyl at C20, thereby making it possible to obtain the compound $C_2$, the compound $C_3$ from double reaction at C6 and C20 and the compound $C_4$ from elimination of the hydroxyl at C14-C15.

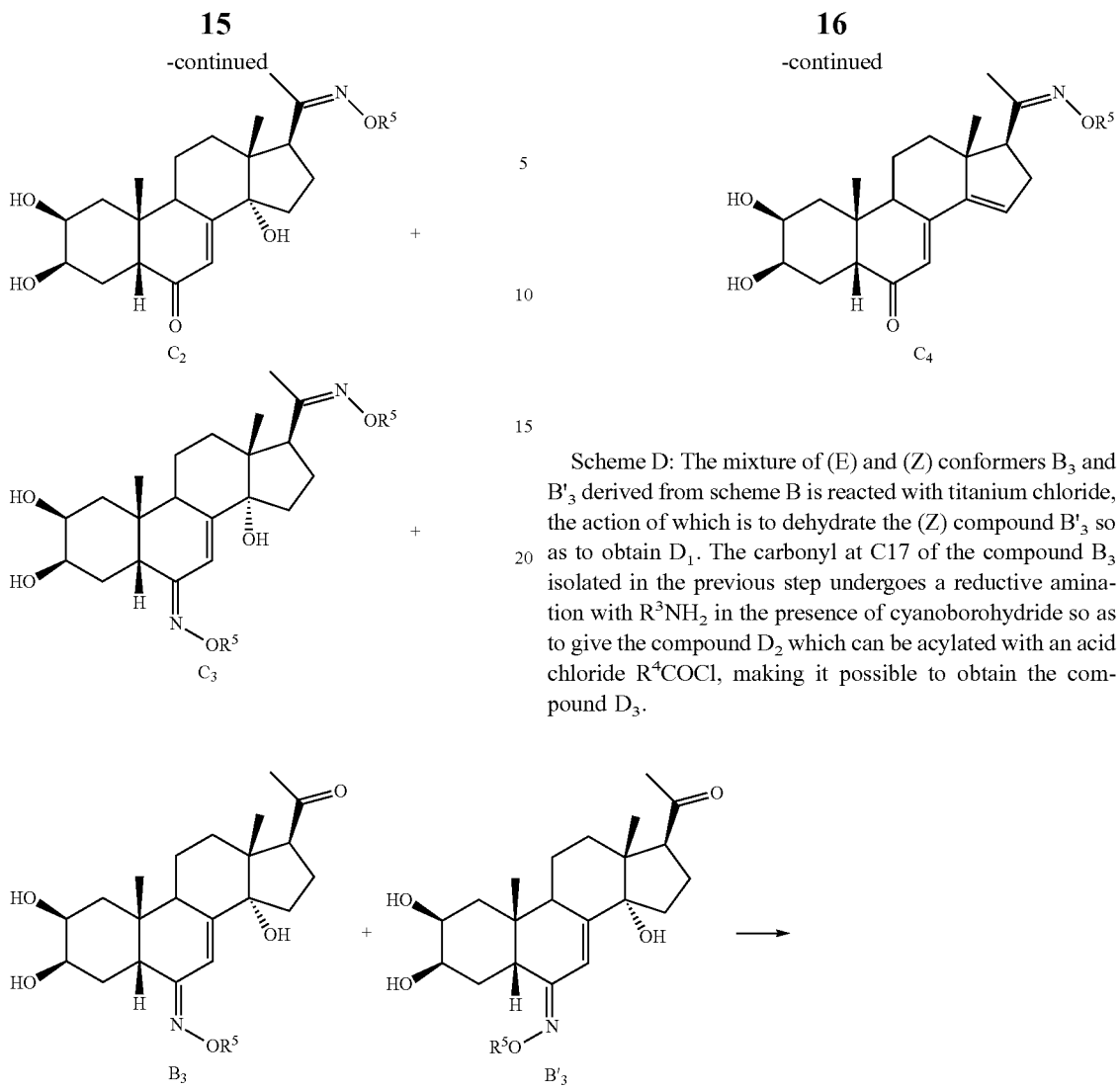

Scheme D: The mixture of (E) and (Z) conformers $B_3$ and $B'_3$ derived from scheme B is reacted with titanium chloride, the action of which is to dehydrate the (Z) compound $B'_3$ so as to obtain $D_1$. The carbonyl at C17 of the compound $B_3$ isolated in the previous step undergoes a reductive amination with $R^3NH_2$ in the presence of cyanoborohydride so as to give the compound $D_2$ which can be acylated with an acid chloride $R^4COCl$, making it possible to obtain the compound $D_3$.

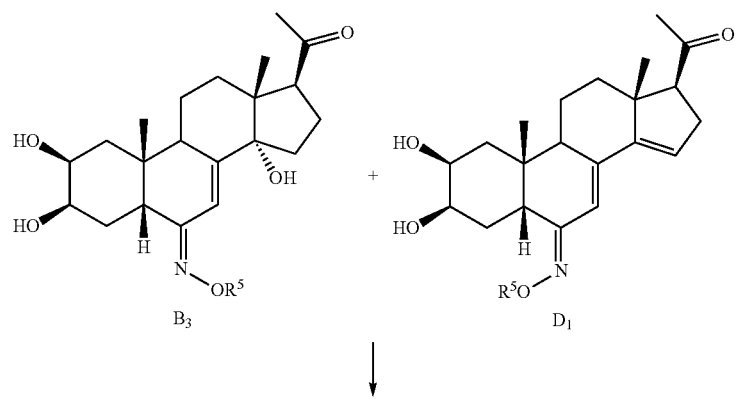

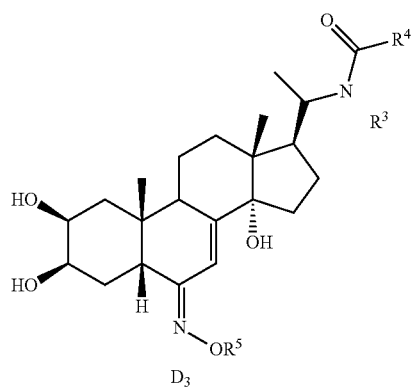

D₃

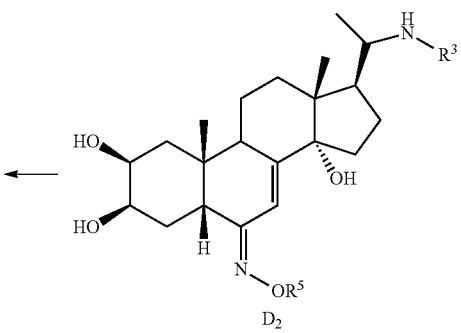

D₂

Scheme E: The poststerone C₁ undergoes a reductive amination and then an acylation of the same type as those described in scheme D and makes it possible to obtain the compounds E₁ and then E₂.

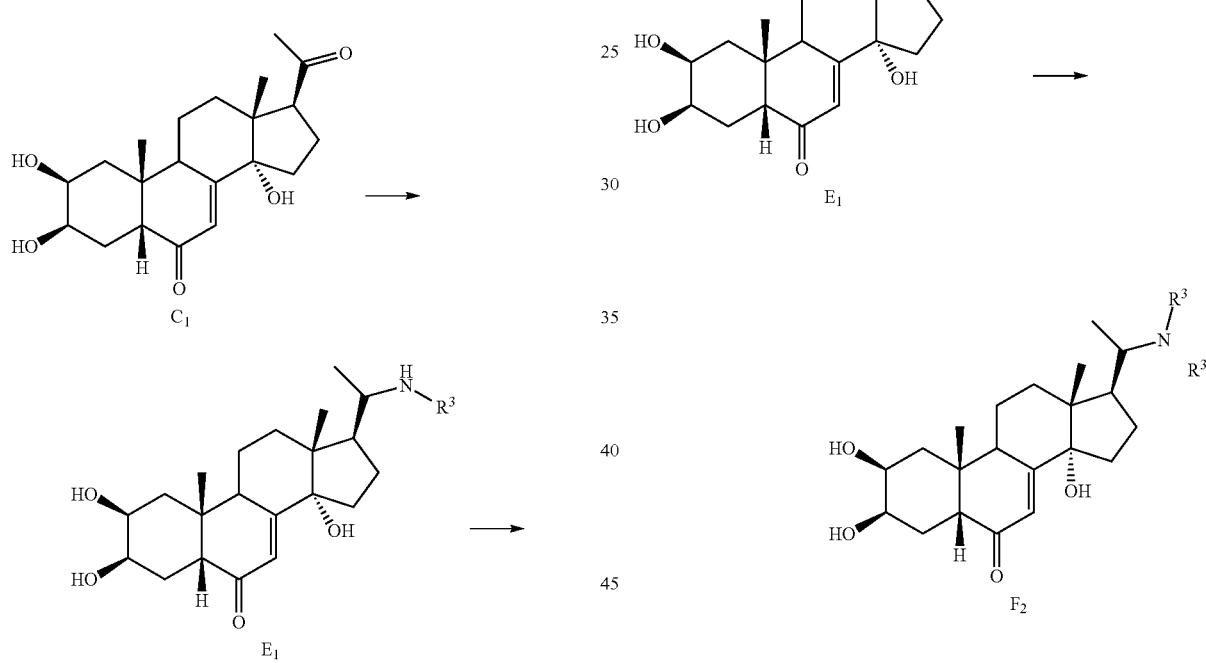

Scheme F: The secondary amine of the compound E₁ derived from scheme F is alkylated with a bromoalkyl compound so as to give the tertiary amine F₂.

Scheme G: The poststerone C₁ can be brominated at C21 using bromine so as to give the brominated compound G₁ which can be alkylated with a nucleophile WR, W possibly being an amine or a thiol, and giving the compound G₂.

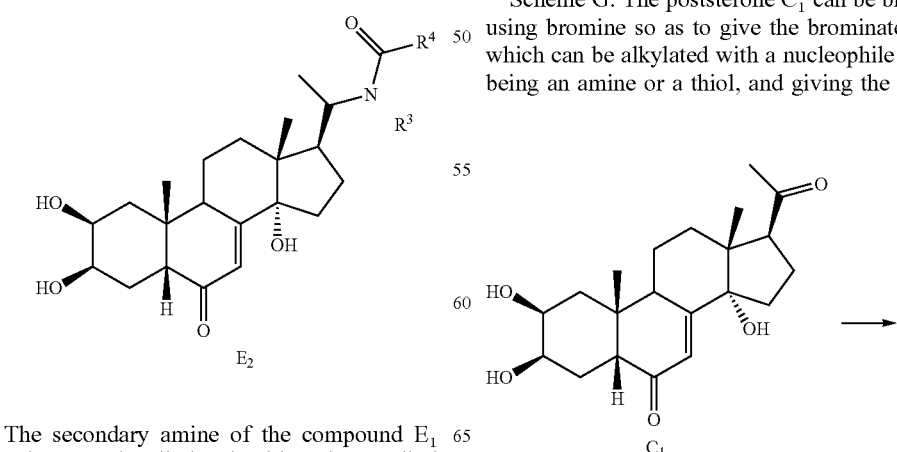

-continued

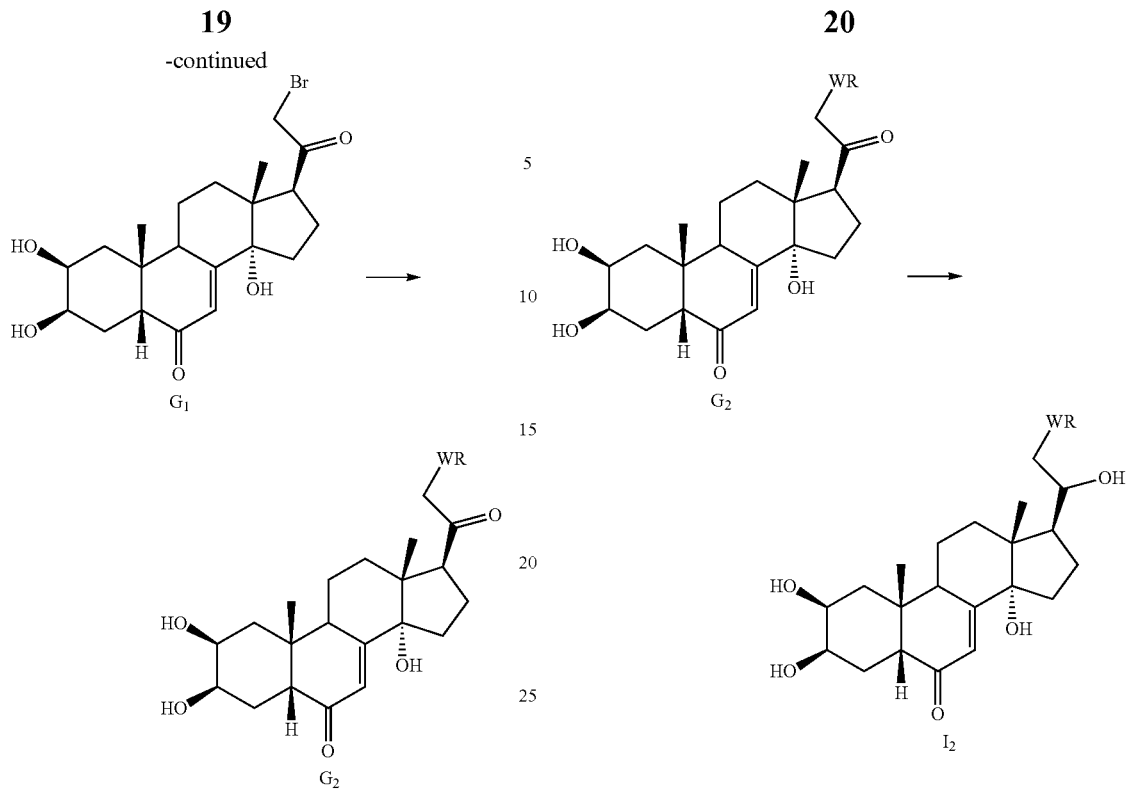

Scheme H: The brominated compound G₁ obtained in scheme G can react with alkoxide compounds of OR type in order to obtain the ethereal compounds H₁.

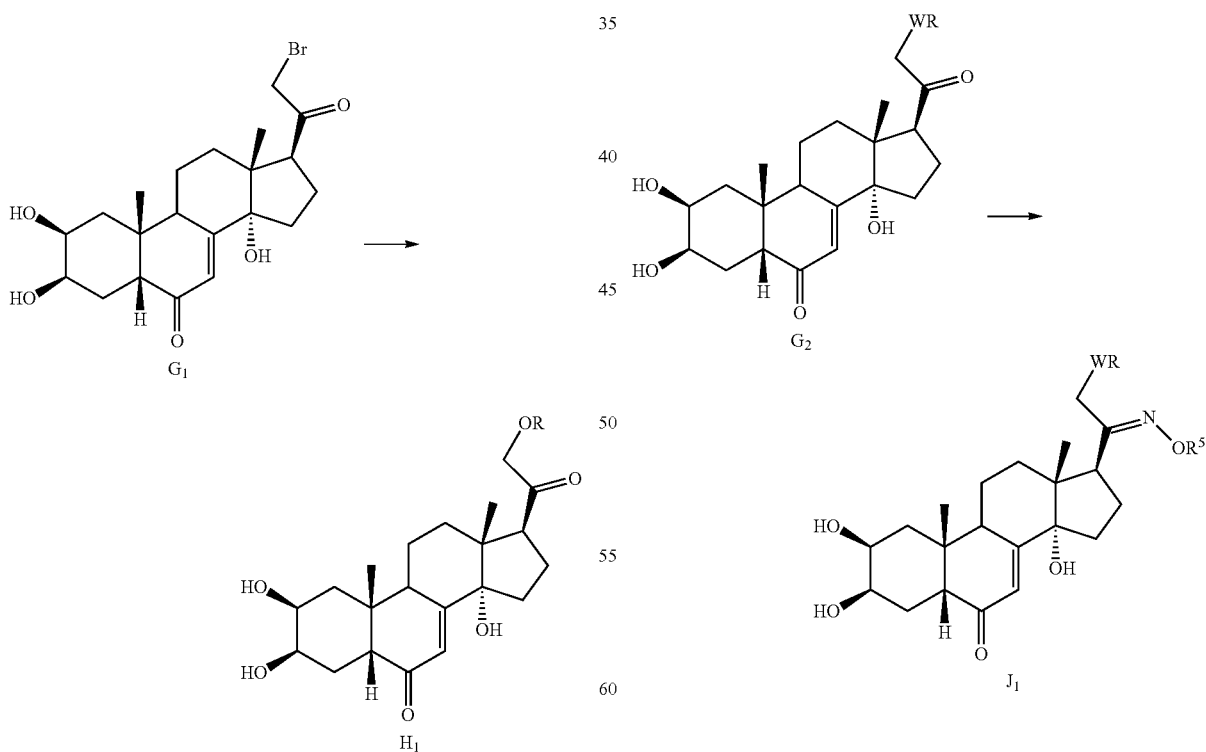

Scheme I: The compounds G₂ derived from scheme G can undergo a reduction of the carbonyl at C20 using sodium borohydride so as to give the alcohols I₂.

Scheme J: The compounds G₂ derived from scheme G can undergo the reaction at C20 of an alkoxamine of $R^5ONH_2$ type as described in scheme C and makes it possible to obtain the compound J₁.

EXAMPLES

Materials and Methods

The proton ($^1$H) nuclear magnetic resonance (NMR) spectra are performed on a Bruker Avance DPX300 apparatus (300.16 MHz). The chemical shifts (δ) are measured in parts per million (ppm). The spectra are calibrated on the chemical shift of the deuterated solvent used. The coupling constants (J) are expressed in Hertz (Hz) and the multiplicity is represented in the following way: singulet (s), doublet (d), doublet of doublets (dd), triplet (t), triplet of doublets (td), quadruplet (q), multiplet (m). The mass spectra (MS) are carried out by an Agilent Technologies MSD, type G1946A, spectrometer, and the samples are ionized by an "atmospheric pressure chemical ionization" (APCI) source.

Abbreviations
TBAF tetrabutylammonium fluoride
THF tetrahydrofuran
DMF dimethylformamide
CDCl₃ deuterated chloroform
CD₃OD deuterated methanol
DMSO-d₆ deuterated dimethyl sulfoxide
PyBop (Benzotriazol-1-yloxy)tripyrrolidinophosphonium hexafluorophosphate
Boc tert-butyloxycarbonyl
mmol millimol(s)
µM micromolar
mL milliliter(s)
g gram(s)
µM mol/liter
N normal
nm nanometer(s)
min minute(s)
h hour(s)
d day(s)
a.t. ambient temperature
UV ultraviolet
ctrl control
MW molecular weight
MS mass spectrometry By way of illustrative examples of the invention, the compounds represented in table 2 were synthesized.

TABLE 2 list of the compounds of which the synthesis is exemplified

| No. | Chemical structure | Chemical name |
|---|---|---|
| 1 | 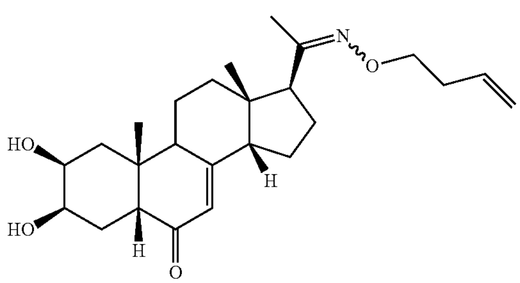 [SMILES: C=CCCON=C(C)[C@H]1CC[C@@H]2C3=CC(=O)[C@@H]4C[C@@H](O)[C@@H](O)C[C@]4(C)C3CC[C@@]21C] | (2S,3R,5R,10R,13S,14S,17S)-17-(N-but-3-enoxy-C-methylcarbonimidoyl)-2,3-dihydroxy-10,13-dimethyl-1,2,3,4,5,9,11,12,14,15,16,17-dodecahydrocyclopenta[a]phenanthren-6-one |
| 2 | 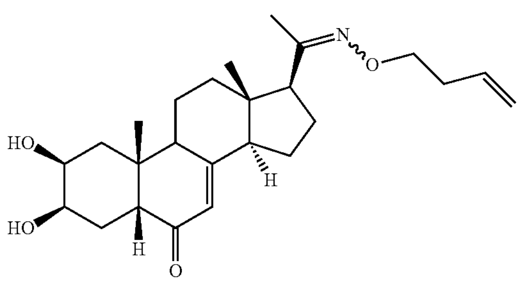 [SMILES: C=CCCON=C(C)[C@H]1CC[C@H]2C3=CC(=O)[C@@H]4C[C@@H](O)[C@@H](O)C[C@]4(C)C3CC[C@]12C] | (2S,3R,5R,10R,13S,14R,17S)-17-(N-but-3-enoxy-C-methylcarbonimidoyl)-2,3-dihydroxy-10,13-dimethyl-1,2,3,4,5,9,11,12,14,15,16,17-dodecahydrocyclopenta[a]phenanthren-6-one |
| 3 | 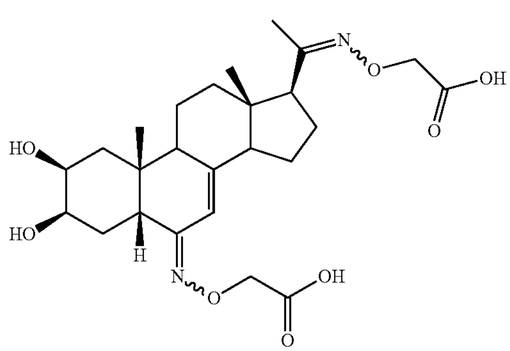 [SMILES: CC(=NOCC(=O)O)[C@H]1CCC2C3=CC(=NOCC(=O)O)[C@@H]4C[C@@H](O)[C@@H](O)C[C@]4(C)C3CC[C@@]21C] | 2-[[(2S,3R,5R,10R,13S,17S)-17-(N-(carboxymethyloxy)-C-methylcarbonimidoyl)-2,3-dihydroxy-10,13-dimethyl-1,2,3,4,5,9,11,12,14,15,16,17-dodecahydrocyclopenta[a]phenanthren-6-ylidene]amino]oxyacetic acid |

TABLE 2-continued list of the compounds of which the synthesis is exemplified

| No. | Chemical structure | Chemical name |
| --- | --- | --- |
| 4 | 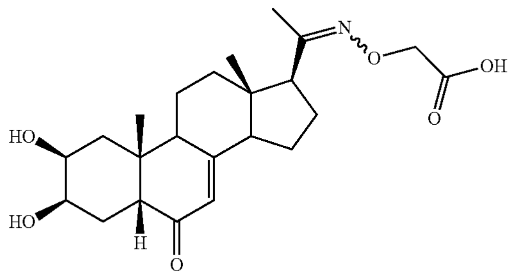 [SMILES: CC(=NOCC(=O)O)[C@H]1CCC2C3=CC(=O)[C@@H]4C[C@@H](O)[C@@H](O)C[C@]4(C)C3CC[C@@]21C] | 2-[1-[(2S,3R,5R,10R,13S,17S)-2,3-dihydroxy-10,13-dimethyl-6-oxo-1,2,3,4,5,9,11,12,14,15,16,17-dodecahydrocyclopenta[a]phenanthren-17-yl]ethylideneamino]oxyacetic acid |
| 5 | 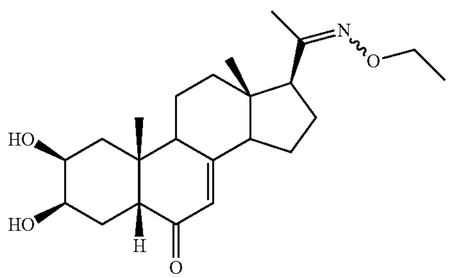 [SMILES: CCON=C(C)[C@H]1CCC2C3=CC(=O)[C@@H]4C[C@@H](O)[C@@H](O)C[C@]4(C)C3CC[C@@]21C] | (2S,3R,5R,10R,13S,17S)-17-(N-ethoxy-C-methylcarbonimidoyl)-2,3-dihydroxy-10,13-dimethyl-1,2,3,4,5,9,11,12,14,15,16,17-dodecahydrocyclopenta[a]phenanthren-6-one |
| 6 | 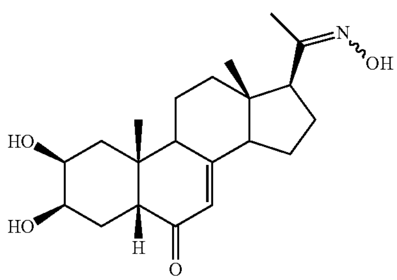 [SMILES: CC(=NO)[C@H]1CCC2C3=CC(=O)[C@@H]4C[C@@H](O)[C@@H](O)C[C@]4(C)C3CC[C@@]21C] | (2S,3R,5R,10R,13S,17S)-2,3-dihydroxy-17-(N-hydroxy-C-methylcarbonimidoyl)-10,13-dimethyl-1,2,3,4,5,9,11,12,14,15,16,17-dodecahydrocyclopenta[a]phenanthren-6-one |
| 7 | 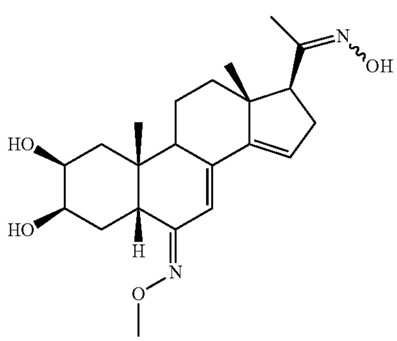 [SMILES: CO/N=C1/C=C2C3=CC[C@H](C(C)=NO)[C@@]3(C)CCC2[C@@]2(C)C[C@H](O)[C@H](O)C[C@@H]12] | 1-[(2S,3R,5R,6Z,10R,13R,17S)-2,3-dihydroxy-6-methoxyimino-10,13-dimethyl-1,2,3,4,5,9,11,12,16,17-decahydrocyclopenta[a]phenanthren-17-yl]ethanone oxime |
| 19 | 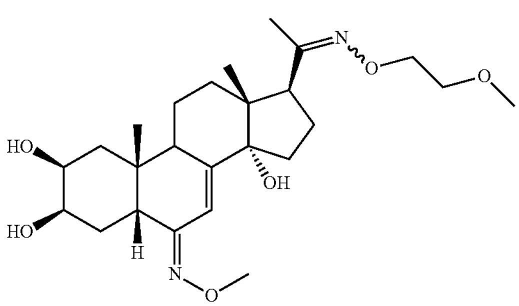 [SMILES: COCCON=C(C)[C@H]1CC[C@@]2(O)C3=C/C(=N\OC)[C@@H]4C[C@@H](O)[C@@H](O)C[C@]4(C)C3CC[C@]12C] | (2S,3R,5R,6E,10R,13R,14S,17S)-17-(N-(2-methoxyethoxy)-C-methylcarbonimidoyl)-6-methoxyimino-10,13-dimethyl-2,3,4,5,9,11,12,15,16,17-decahydro-1H-cyclopenta[a]phenanthrene-2,3,14-triol |

TABLE 2-continued list of the compounds of which the synthesis is exemplified

| No. | Chemical structure | Chemical name |
| --- | --- | --- |
| 21 | 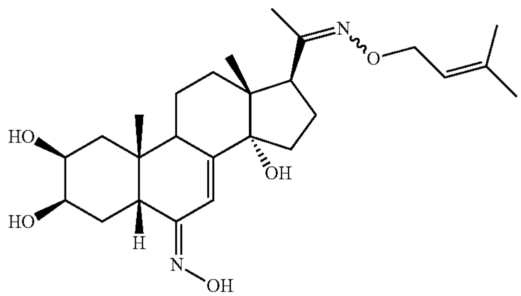 [SMILES: CC(C)=CCON=C(C)[C@H]1CC[C@@]2(O)C3=C/C(=N\O)[C@@H]4C[C@@H](O)[C@@H](O)C[C@]4(C)C3CC[C@]12C] | (2S,3R,5R,10R,13R,14S,17S)-2,3,14-trihydroxy-10,13-dimethyl-17-(C-methyl-N-(3-methylbut-2-enoxy)carbonimidoyl)-2,3,4,5,9,11,12,15,16,17-decahydro-1H-cyclopenta[a]phenanthren-6-one oxime |
| 23 | 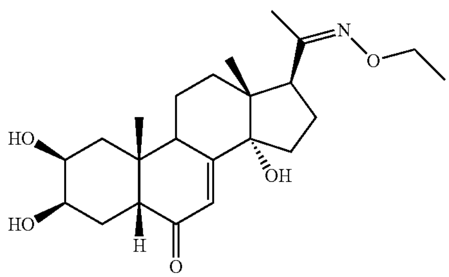 [SMILES: CCO/N=C(/C)[C@H]1CC[C@@]2(O)C3=CC(=O)[C@@H]4C[C@@H](O)[C@@H](O)C[C@]4(C)C3CC[C@]12C] | (2S,3R,5R,10R,13R,14S,17S)-17-(N-ethoxy-C-methylcarbonimidoyl)-2,3,14-trihydroxy-10,13-dimethyl-2,3,4,5,9,11,12,15,16,17-decahydro-1H-cyclopenta[a]phenanthren-6-one |
| 24 | 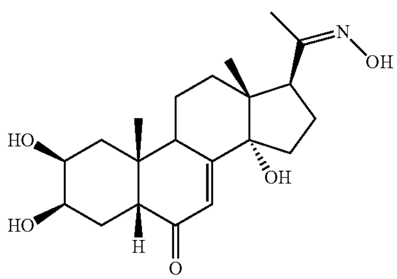 [SMILES: C/C(=N/O)[C@H]1CC[C@@]2(O)C3=CC(=O)[C@@H]4C[C@@H](O)[C@@H](O)C[C@]4(C)C3CC[C@]12C] | (2S,3R,5R,10R,13R,14S,17S)-2,3,14-trihydroxy-17-(N-hydroxy-C-methylcarbonimidoyl)-10,13-dimethyl-2,3,4,5,9,11,12,15,16,17-decahydro-1H-cyclopenta[a]phenanthren-6-one |
| 25 | 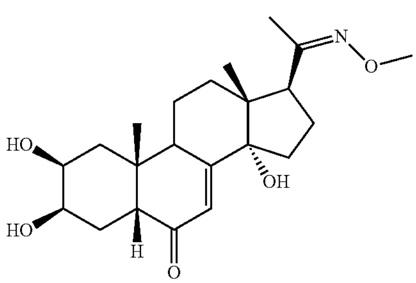 [SMILES: CO/N=C(/C)[C@H]1CC[C@@]2(O)C3=CC(=O)[C@@H]4C[C@@H](O)[C@@H](O)C[C@]4(C)C3CC[C@]12C] | (2S,3R,5R,10R,13R,14S,17S)-17-(N-methoxy-C-methylcarbonimidoyl)-2,3,14-trihydroxy-10,13-dimethyl-2,3,4,5,9,11,12,15,16,17-decahydro-1H-cyclopenta[a]phenanthren-6-one |
| 26 | 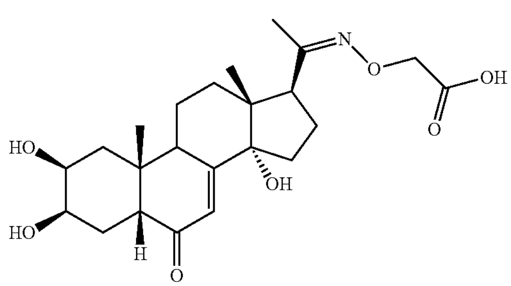 [SMILES: C/C(=N/OCC(=O)O)[C@H]1CC[C@@]2(O)C3=CC(=O)[C@@H]4C[C@@H](O)[C@@H](O)C[C@]4(C)C3CC[C@]12C] | 2-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethylideneamino]oxyacetic acid |

TABLE 2-continued list of the compounds of which the synthesis is exemplified

| No. | Chemical structure | Chemical name |
| --- | --- | --- |
| 27 | 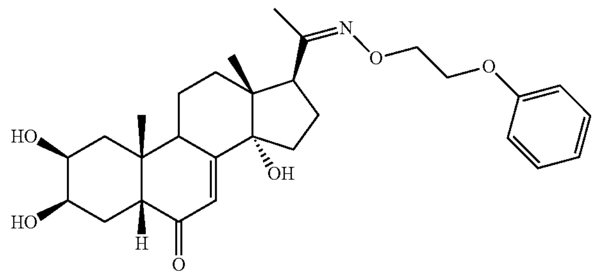 [SMILES: C/C(=N/OCCOc1ccccc1)[C@H]1CC[C@@]2(O)C3=CC(=O)[C@@H]4C[C@@H](O)[C@@H](O)C[C@]4(C)C3CC[C@]12C] | (2S,3R,5R,10R,13R,14S,17S)-2,3,14-trihydroxy-10,13-dimethyl-17-(C-methyl-N-(2-phenoxyethoxy)carbonimidoyl)-2,3,4,5,9,11,12,15,16,17-decahydro-1H-cyclopenta[a]phenanthren-6-one |
| 28 | 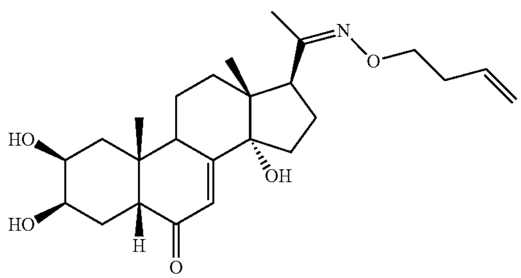 [SMILES: C=CCCO/N=C(/C)[C@H]1CC[C@@]2(O)C3=CC(=O)[C@@H]4C[C@@H](O)[C@@H](O)C[C@]4(C)C3CC[C@]12C] | (2S,3R,5R,10R,13R,14S,17S)-17-(N-but-3-enoxy-C-methylcarbonimidoyl)-2,3,14-trihydroxy-10,13-dimethyl-2,3,4,5,9,11,12,15,16,17-decahydro-1H-cyclopenta[a]phenanthren-6-one |
| 29 | 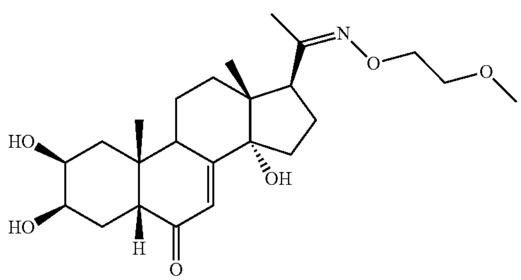 [SMILES: COCCO/N=C(/C)[C@H]1CC[C@@]2(O)C3=CC(=O)[C@@H]4C[C@@H](O)[C@@H](O)C[C@]4(C)C3CC[C@]12C] | (2S,3R,5R,10R,13R,14S,17S)-2,3,14-trihydroxy-17-(N-(2-methoxyethoxy)-C-methylcarbonimidoyl)-10,13-dimethyl-2,3,4,5,9,11,12,15,16,17-decahydro-1H-cyclopenta[a]phenanthren-6-one |
| 30 | 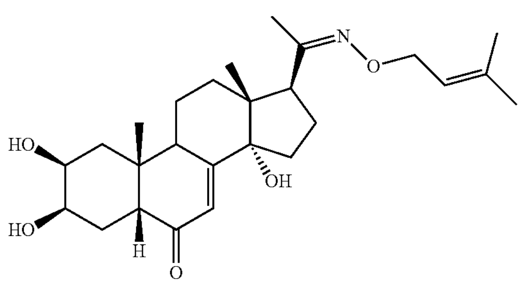 [SMILES: CC(C)=CCO/N=C(/C)[C@H]1CC[C@@]2(O)C3=CC(=O)[C@@H]4C[C@@H](O)[C@@H](O)C[C@]4(C)C3CC[C@]12C] | (2S,3R,5R,10R,13R,14S,17S)-2,3,14-trihydroxy-10,13-dimethyl-17-(C-methyl-N-(3-methylbut-2-enoxy)carbonimidoyl)-2,3,4,5,9,11,12,15,16,17-decahydro-1H-cyclopenta[a]phenanthren-6-one |
| 31 | 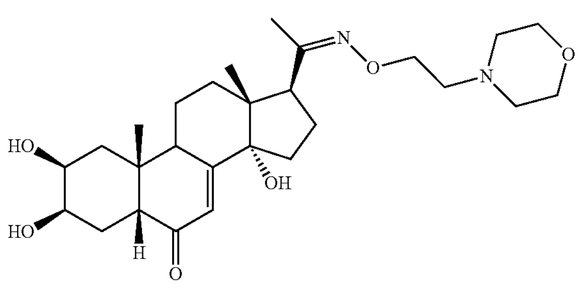 [SMILES: C/C(=N/OCCN1CCOCC1)[C@H]1CC[C@@]2(O)C3=CC(=O)[C@@H]4C[C@@H](O)[C@@H](O)C[C@]4(C)C3CC[C@]12C] | (2S,3R,5R,10R,13R,14S,17S)-2,3,14-trihydroxy-10,13-dimethyl-17-(C-methyl-N-(2-morpholinoethoxy)carbonimidoyl)-2,3,4,5,9,11,12,15,16,17-decahydro-1H-cyclopenta[a]phenanthren-6-one |

TABLE 2-continued list of the compounds of which the synthesis is exemplified

| No. | Chemical structure | Chemical name |
|---|---|---|
| 32 | 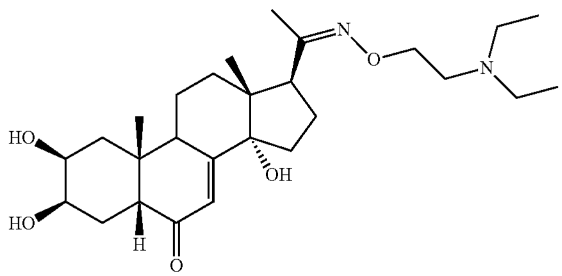 [SMILES: CCN(CC)CCO/N=C(/C)[C@H]1CC[C@@]2(O)C3=CC(=O)[C@@H]4C[C@@H](O)[C@@H](O)C[C@]4(C)C3CC[C@]12C] | (2S,3R,5R,10R,13R,14S,17S)-17-(N-(2-diethylaminoethoxy)-C-methylcarbonimidoyl)-2,3,14-trihydroxy-10,13-dimethyl-2,3,4,5,9,11,12,15,16,17-decahydro-1H-cyclopenta[a]phenanthren-6-one |
| 33 | 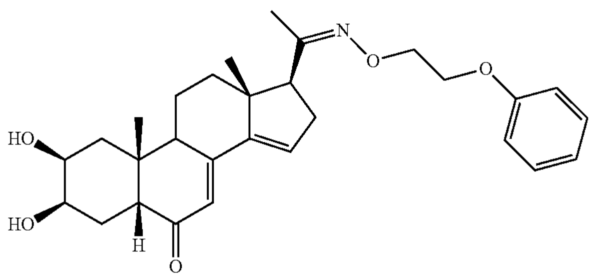 [SMILES: C/C(=N/OCCOc1ccccc1)[C@H]1CC=C2C3=CC(=O)[C@@H]4C[C@@H](O)[C@@H](O)C[C@]4(C)C3CC[C@@]21C] | (2S,3R,5R,10R,13R,17S)-2,3-dihydroxy-10,13-dimethyl-17-(C-methyl-N-(2-phenoxyethoxy)carbonimidoyl)-1,2,3,4,5,9,11,12,16,17-decahydrocyclopenta[a]phenanthren-6-one |
| 34 | 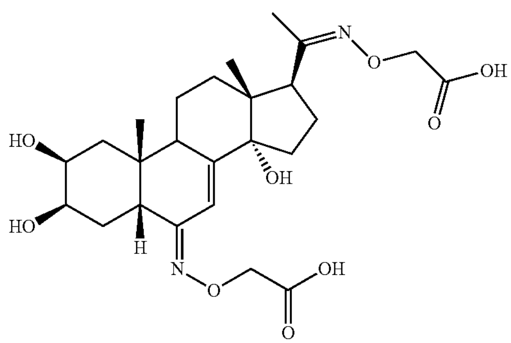 [SMILES: C/C(=N/OCC(=O)O)[C@H]1CC[C@@]2(O)C3=C/C(=N\OCC(=O)O)[C@@H]4C[C@@H](O)[C@@H](O)C[C@]4(C)C3CC[C@]12C] | 2-[[(2S,3R,5R,10R,13R,14S,17S)-17-(N-(carboxymethyloxy)-C-methylcarbonimidoyl)-2,3,14-trihydroxy-10,13-dimethyl-2,3,4,5,9,11,12,15,16,17-decahydro-1H-cyclopenta[a]phenanthren-6-ylidene]amino]oxyacetic acid |
| 35 | 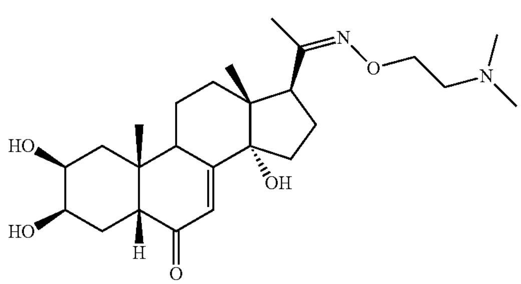 [SMILES: C/C(=N/OCCN(C)C)[C@H]1CC[C@@]2(O)C3=CC(=O)[C@@H]4C[C@@H](O)[C@@H](O)C[C@]4(C)C3CC[C@]12C] | (2S,3R,5R,10R,13R,14S,17S)-17-(N-(2-dimethylaminoethoxy)-C-methylcarbonimidoyl)-2,3,14-trihydroxy-10,13-dimethyl-2,3,4,5,9,11,12,15,16,17-decahydro-1H-cyclopenta[a]phenanthren-6-one |
| 36 | 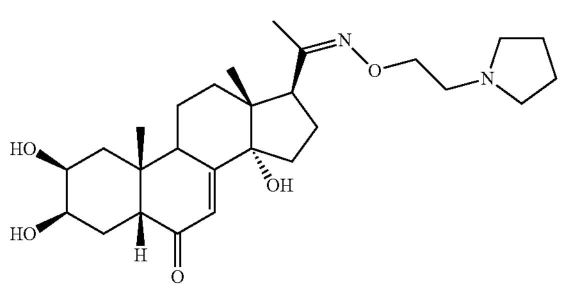 [SMILES: C/C(=N/OCCN1CCCC1)[C@H]1CC[C@@]2(O)C3=CC(=O)[C@@H]4C[C@@H](O)[C@@H](O)C[C@]4(C)C3CC[C@]12C] | (2S,3R,5R,10R,13R,14S,17S)-2,3,14-trihydroxy-10,13-dimethyl-17-(C-methyl-N-(2-pyrrolidin-1-ylethoxy)carbonimidoyl)-2,3,4,5,9,11,12,15,16,17-decahydro-1H-cyclopenta[a]phenanthren-6-one |

TABLE 2-continued list of the compounds of which the synthesis is exemplified

| No. | Chemical structure | Chemical name |
|---|---|---|
| 37 | 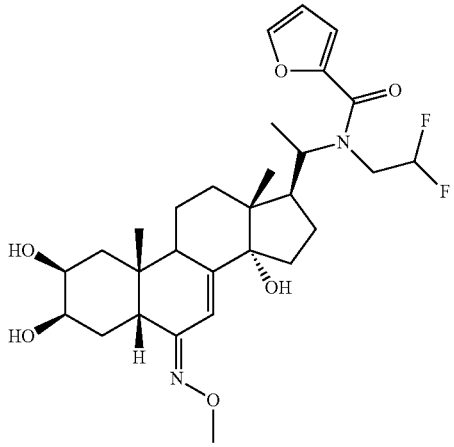 [SMILES: CO/N=C1\C=C2C(CC[C@]3(C)[C@@H](C(C)N(CC(F)F)C(=O)c4ccco4)CC[C@@]23O)[C@@]2(C)C[C@H](O)[C@H](O)C[C@@H]12] | N-(2,2-difluoroethyl)-N-[1-[(2S,3R,5R,6E,10R,13R,14S,17S)-2,3,14-trihydroxy-6-methoxyimino-10,13-dimethyl-2,3,4,5,9,11,12,15,16,17-decahydro-1H-cyclopenta[a]phenanthren-17-yl]ethyl]furan-2-carboxamide |
| 38 | 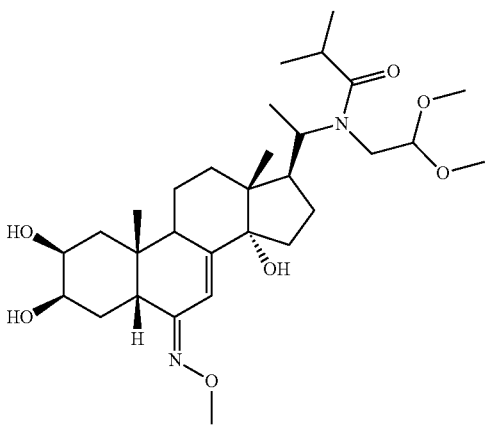 [SMILES: CO/N=C1\C=C2C(CC[C@]3(C)[C@@H](C(C)N(CC(OC)OC)C(=O)C(C)C)CC[C@@]23O)[C@@]2(C)C[C@H](O)[C@H](O)C[C@@H]12] | N-(2,2-dimethoxyethyl)-2-methyl-N-[1-[(2S,3R,5R,6E,10R,13R,14S,17S)-2,3,14-trihydroxy-6-methoxyimino-10,13-dimethyl-2,3,4,5,9,11,12,15,16,17-decahydro-1H-cyclopenta[a]phenanthren-17-yl]ethyl]propanamide |
| 39 | 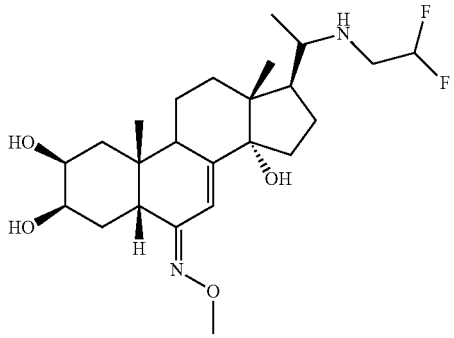 [SMILES: CO/N=C1\C=C2C(CC[C@]3(C)[C@@H](C(C)NCC(F)F)CC[C@@]23O)[C@@]2(C)C[C@H](O)[C@H](O)C[C@@H]12] | (2S,3R,5R,6E,10R,13R,14S,17S)-17-[1-(2,2-difluoroethylamino)ethyl]-6-methoxyimino-10,13-dimethyl-2,3,4,5,9,11,12,15,16,17-decahydro-1H-cyclopenta[a]phenanthrene-2,3,14-triol |

TABLE 2-continued list of the compounds of which the synthesis is exemplified

| No. | Chemical structure | Chemical name |
|---|---|---|
| 40 | 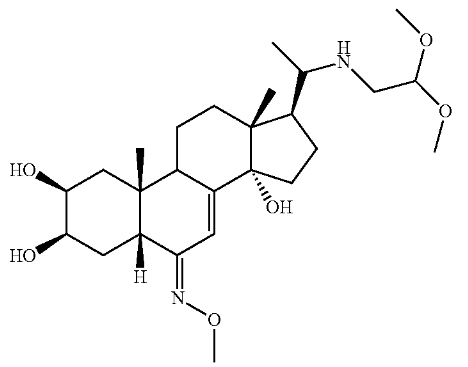 [SMILES: CO/N=C1\C=C2C(CC[C@]3(C)[C@@H](C(C)NCC(OC)OC)CC[C@@]23O)[C@@]2(C)C[C@H](O)[C@H](O)C[C@@H]12] | (2S,3R,5R,6E,10R,13R,14S,17S)-17-[1-(2,2-dimethoxyethylamino)ethyl]-6-methoxyimino-10,13-dimethyl-2,3,4,5,9,11,12,15,16,17-decahydro-1H-cyclopenta[a]phenanthrene-2,3,14-triol |
| 41 | 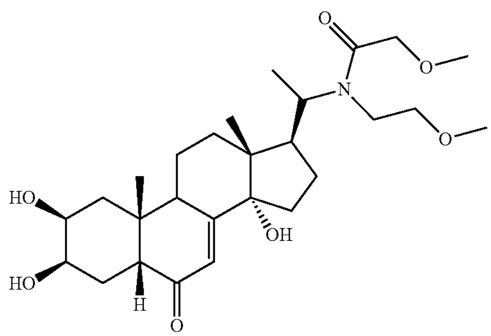 [SMILES: COCCN(C(=O)COC)C(C)[C@H]1CC[C@@]2(O)C3=CC(=O)[C@@H]4C[C@@H](O)[C@@H](O)C[C@]4(C)C3CC[C@]12C] | 2-methoxy-N-(2-methoxyethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]acetamide |
| 42 | 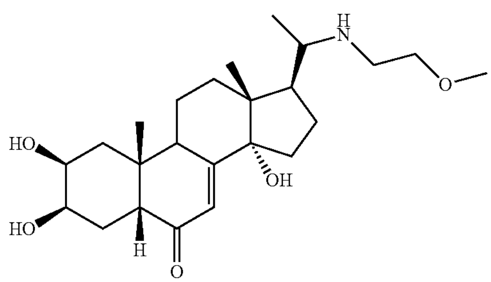 [SMILES: COCCNC(C)[C@H]1CC[C@@]2(O)C3=CC(=O)[C@@H]4C[C@@H](O)[C@@H](O)C[C@]4(C)C3CC[C@]12C] | (2S,3R,5R,10R,13R,14S,17S)-2,3,14-trihydroxy-17-[1-(2-methoxyethylamino)ethyl]-10,13-dimethyl-2,3,4,5,9,11,12,15,16,17-decahydro-1H-cyclopenta[a]phenanthren-6-one |
| 43 | 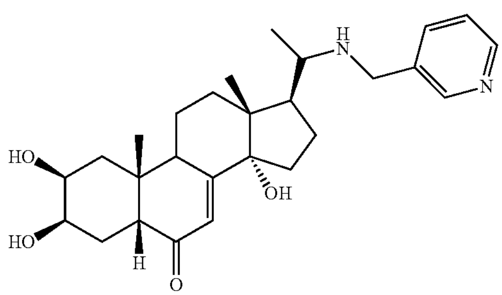 [SMILES: CC(NCc1cccnc1)[C@H]1CC[C@@]2(O)C3=CC(=O)[C@@H]4C[C@@H](O)[C@@H](O)C[C@]4(C)C3CC[C@]12C] | (2S,3R,5R,10R,13R,14S,17S)-2,3,14-trihydroxy-10,13-dimethyl-17-[1-(3-pyridylmethylamino)ethyl]-2,3,4,5,9,11,12,15,16,17-decahydro-1H-cyclopenta[a]phenanthren-6-one |
| 44 | 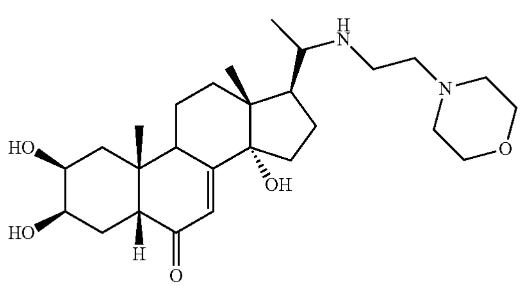 [SMILES: CC(NCCN1CCOCC1)[C@H]1CC[C@@]2(O)C3=CC(=O)[C@@H]4C[C@@H](O)[C@@H](O)C[C@]4(C)C3CC[C@]12C] | (2S,3R,5R,10R,13R,14S,17S)-2,3,14-trihydroxy-10,13-dimethyl-17-[1-(2-morpholinoethylamino)ethyl]-2,3,4,5,9,11,12,15,16,17-decahydro-1H-cyclopenta[a]phenanthren-6-one |

TABLE 2-continued list of the compounds of which the synthesis is exemplified

| No. | Chemical structure | Chemical name |
|---|---|---|
| 45 | 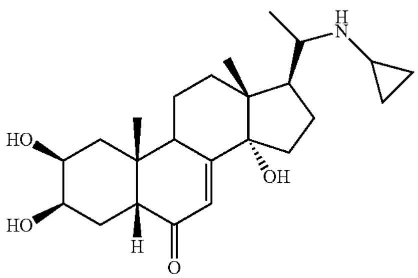 [SMILES: CC(NC1CC1)[C@H]1CC[C@@]2(O)C3=CC(=O)[C@@H]4C[C@@H](O)[C@@H](O)C[C@]4(C)C3CC[C@]12C] | (2S,3R,5R,10R,13R,14S,17S)-17-[1-(cyclopropylamino)ethyl]-2,3,14-trihydroxy-10,13-dimethyl-2,3,4,5,9,11,12,15,16,17-decahydro-1H-cyclopenta[a]phenanthren-6-one |
| 46 | 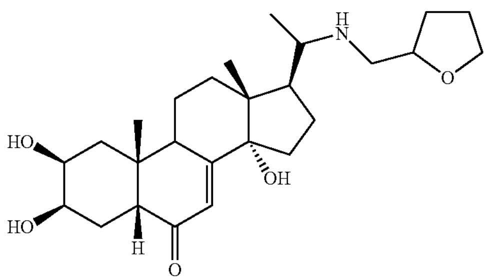 [SMILES: CC(NCC1CCCO1)[C@H]1CC[C@@]2(O)C3=CC(=O)[C@@H]4C[C@@H](O)[C@@H](O)C[C@]4(C)C3CC[C@]12C] | (2S,3R,5R,10R,13R,14S,17S)-2,3,14-trihydroxy-10,13-dimethyl-17-[1-(tetrahydrofuran-2-ylmethylamino)ethyl]-2,3,4,5,9,11,12,15,16,17-decahydro-1H-cyclopenta[a]phenanthren-6-one |
| 47 | 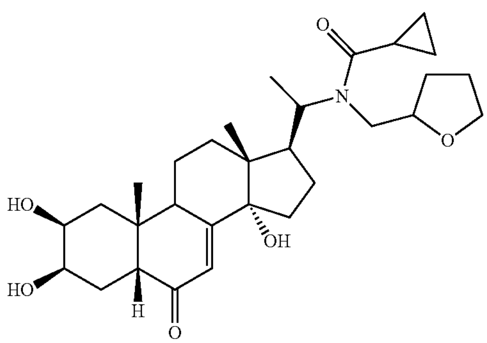 [SMILES: CC([C@H]1CC[C@@]2(O)C3=CC(=O)[C@@H]4C[C@@H](O)[C@@H](O)C[C@]4(C)C3CC[C@]12C)N(CC1CCCO1)C(=O)C1CC1] | N-(tetrahydrofuran-2-ylmethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]cyclopropanecarboxamide |
| 48 | 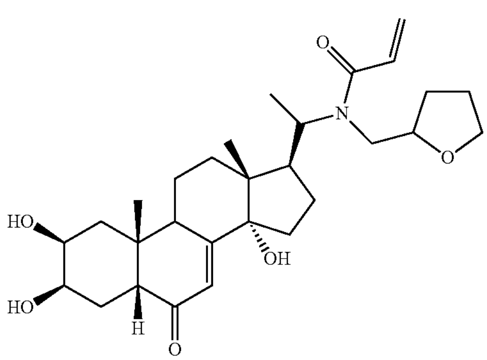 [SMILES: C=CC(=O)N(CC1CCCO1)C(C)[C@H]1CC[C@@]2(O)C3=CC(=O)[C@@H]4C[C@@H](O)[C@@H](O)C[C@]4(C)C3CC[C@]12C] | N-(tetrahydrofuran-2-ylmethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]prop-2-enamide |

TABLE 2-continued list of the compounds of which the synthesis is exemplified

| No. | Chemical structure | Chemical name |
|---|---|---|
| 49 | 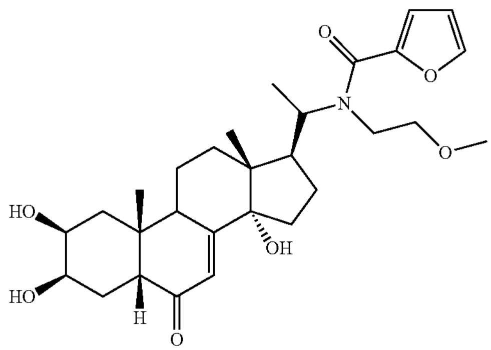 [SMILES: COCCN(C(=O)c1ccco1)C(C)[C@H]1CC[C@@]2(O)C3=CC(=O)[C@@H]4C[C@@H](O)[C@@H](O)C[C@]4(C)C3CC[C@]12C] | N-(2-methoxyethyl)-N-(1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]furan-2-carboxamide |
| 50 | 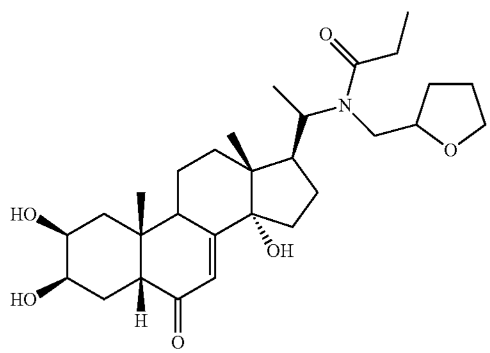 [SMILES: CCC(=O)N(CC1CCCO1)C(C)[C@H]1CC[C@@]2(O)C3=CC(=O)[C@@H]4C[C@@H](O)[C@@H](O)C[C@]4(C)C3CC[C@]12C] | N-(tetrahydrofuran-2-ylmethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]propanamide |
| 51 | 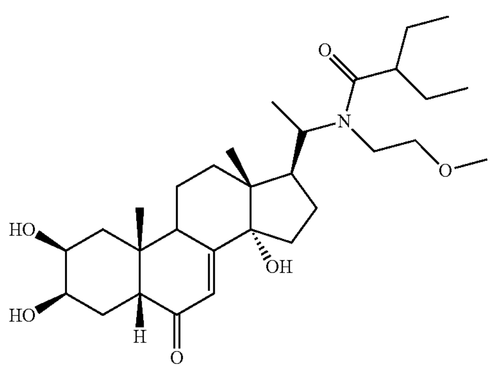 [SMILES: CCC(CC)C(=O)N(CCOC)C(C)[C@H]1CC[C@@]2(O)C3=CC(=O)[C@@H]4C[C@@H](O)[C@@H](O)C[C@]4(C)C3CC[C@]12C] | 2-ethyl-N-(2-methoxyethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]butanamide |
| 52 | 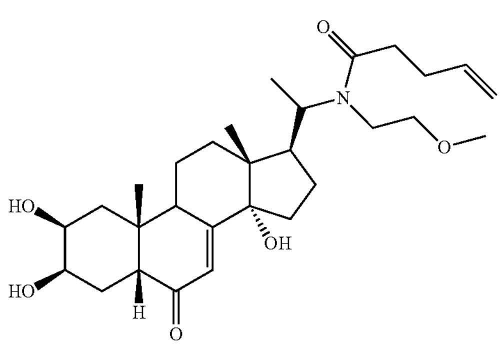 [SMILES: C=CCCC(=O)N(CCOC)C(C)[C@H]1CC[C@@]2(O)C3=CC(=O)[C@@H]4C[C@@H](O)[C@@H](O)C[C@]4(C)C3CC[C@]12C] | N-(2-methoxyethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]pent-4-enamide |

TABLE 2-continued list of the compounds of which the synthesis is exemplified

| No. | Chemical structure | Chemical name |
|---|---|---|
| 53 | 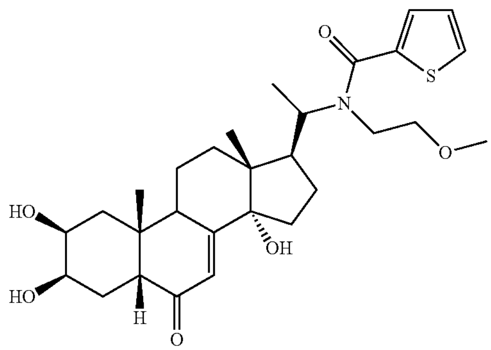 [SMILES: COCCN(C(=O)c1cccs1)C(C)[C@H]1CC[C@@]2(O)C3=CC(=O)[C@@H]4C[C@@H](O)[C@@H](O)C[C@]4(C)C3CC[C@]12C] | N-(2-methoxyethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]thiophene-2-carboxamide |
| 54 | 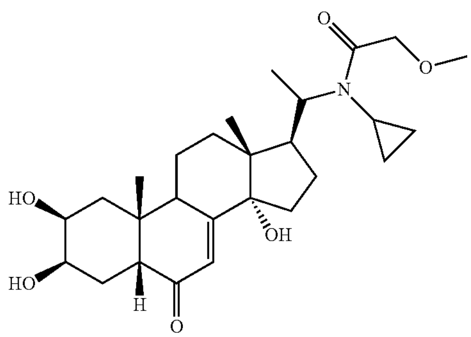 [SMILES: COCC(=O)N(C1CC1)C(C)[C@H]1CC[C@@]2(O)C3=CC(=O)[C@@H]4C[C@@H](O)[C@@H](O)C[C@]4(C)C3CC[C@]12C] | N-cyclopropyl-2-methoxy-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]acetacetamide |
| 55 | 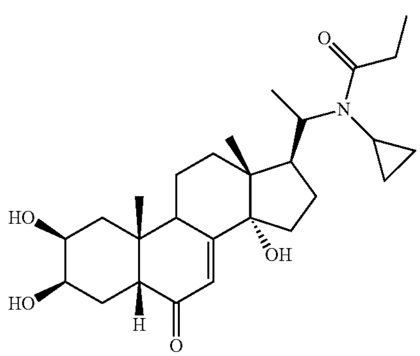 [SMILES: CCC(=O)N(C1CC1)C(C)[C@H]1CC[C@@]2(O)C3=CC(=O)[C@@H]4C[C@@H](O)[C@@H](O)C[C@]4(C)C3CC[C@]12C] | N-cyclopropyl-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]propanamide |
| 56 | 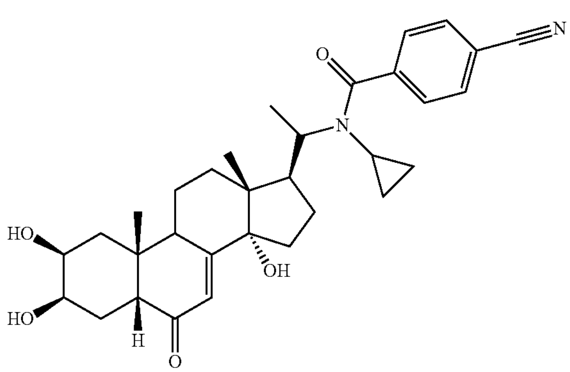 [SMILES: CC([C@H]1CC[C@@]2(O)C3=CC(=O)[C@@H]4C[C@@H](O)[C@@H](O)C[C@]4(C)C3CC[C@]12C)N(C(=O)c1ccc(C#N)cc1)C1CC1] | 4-cyano-N-cyclopropyl-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]benzamide |

TABLE 2-continued list of the compounds of which the synthesis is exemplified

| No. | Chemical structure | Chemical name |
| --- | --- | --- |
| 57 | 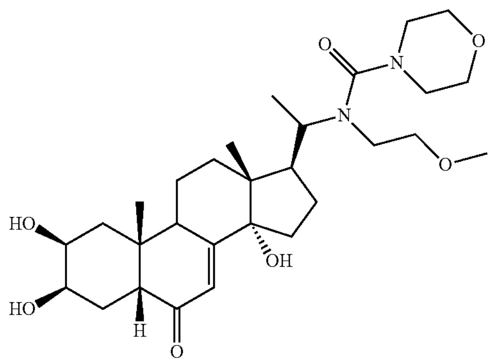 [SMILES: COCCN(C(=O)N1CCOCC1)C(C)[C@H]1CC[C@@]2(O)C3=CC(=O)[C@@H]4C[C@@H](O)[C@@H](O)C[C@]4(C)C3CC[C@]12C] | N-(2-methoxyethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]morpholine-4-carboxamide |
| 58 | 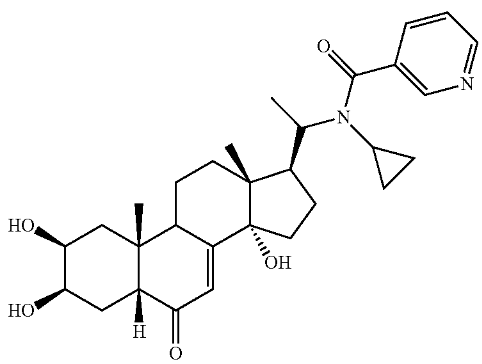 [SMILES: CC([C@H]1CC[C@@]2(O)C3=CC(=O)[C@@H]4C[C@@H](O)[C@@H](O)C[C@]4(C)C3CC[C@]12C)N(C(=O)c1cccnc1)C1CC1] | N-cyclopropyl-N-[1-((2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]pyridine-3-carboxamide |
| 59 | 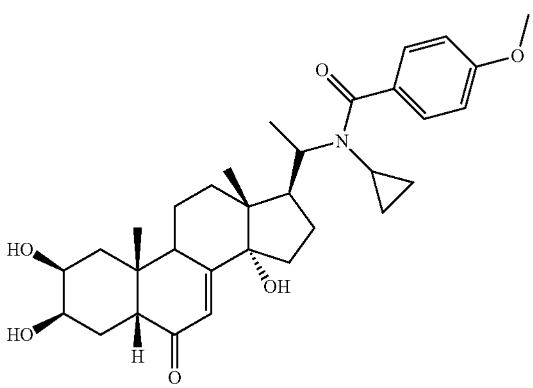 [SMILES: COc1ccc(C(=O)N(C2CC2)C(C)[C@H]2CC[C@@]3(O)C4=CC(=O)[C@@H]5C[C@@H](O)[C@@H](O)C[C@]5(C)C4CC[C@]23C)cc1] | N-cyclopropyl-4-methoxy-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]benzamide |
| 60 | 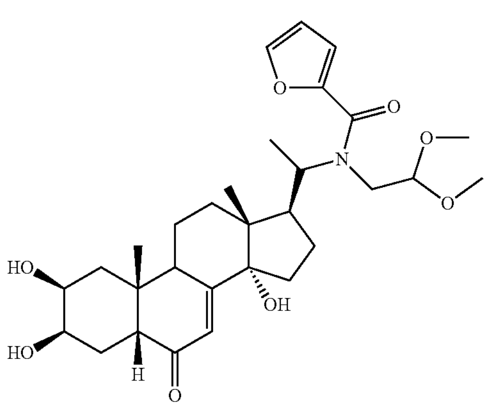 | N-(2,2-dimethoxyethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]furan-2-carboxamide |

TABLE 2-continued list of the compounds of which the synthesis is exemplified

| No. | Chemical structure | Chemical name |
|---|---|---|
| 61 | 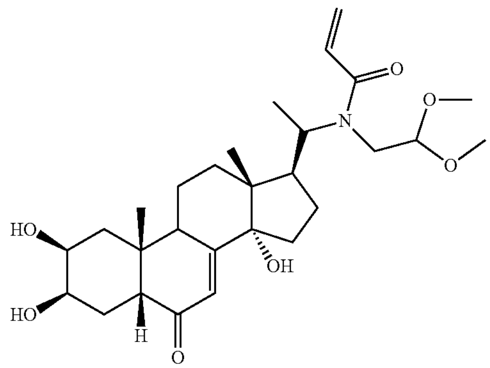 [SMILES: C=CC(=O)N(CC(OC)OC)C(C)[C@H]1CC[C@@]2(O)C3=CC(=O)[C@@H]4C[C@@H](O)[C@@H](O)C[C@]4(C)C3CC[C@]12C] | N-(2,2-dimethoxyethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]prop-2-enamide |
| 62 | 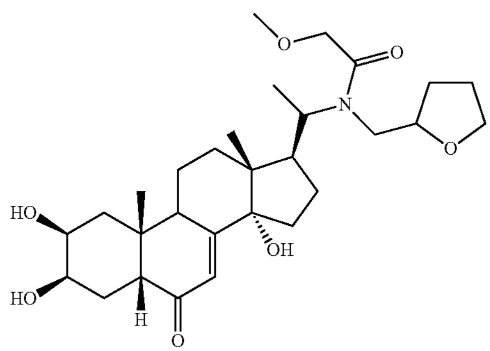 [SMILES: COCC(=O)N(CC1CCCO1)C(C)[C@H]1CC[C@@]2(O)C3=CC(=O)[C@@H]4C[C@@H](O)[C@@H](O)C[C@]4(C)C3CC[C@]12C] | 2-methoxy-N-(tetrahydrofuran-2-ylmethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]acetamide |
| 63 | 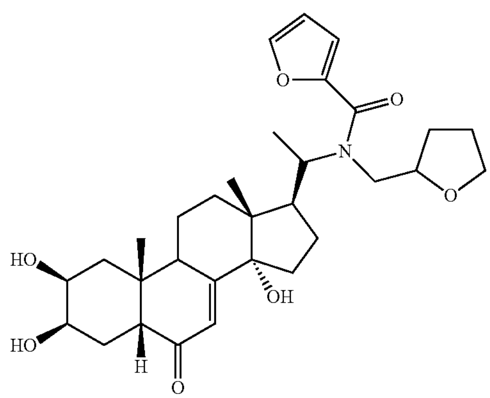 [SMILES: CC([C@H]1CC[C@@]2(O)C3=CC(=O)[C@@H]4C[C@@H](O)[C@@H](O)C[C@]4(C)C3CC[C@]12C)N(CC1CCCO1)C(=O)c1ccco1] | N-(tetrahydrofuran-2-ylmethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]furan-2-carboxamide |
| 64 | 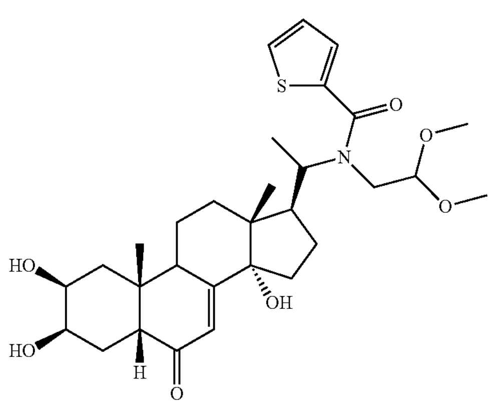 [SMILES: COC(CN(C(=O)c1cccs1)C(C)[C@H]1CC[C@@]2(O)C3=CC(=O)[C@@H]4C[C@@H](O)[C@@H](O)C[C@]4(C)C3CC[C@]12C)OC] | N-(2,2-dimethoxyethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]thiophene-2-carboxamide |

TABLE 2-continued list of the compounds of which the synthesis is exemplified

| No. | Chemical structure | Chemical name |
|---|---|---|
| 65 | 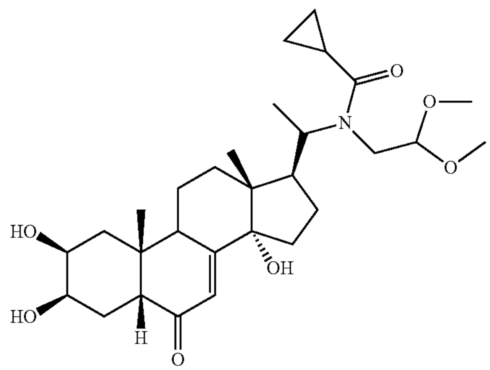 [SMILES: COC(CN(C(=O)C1CC1)C(C)[C@H]1CC[C@@]2(O)C3=CC(=O)[C@@H]4C[C@@H](O)[C@@H](O)C[C@]4(C)C3CC[C@]12C)OC] | N-(2,2-dimethoxyethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]cyclopropanecarboxamide |
| 66 | 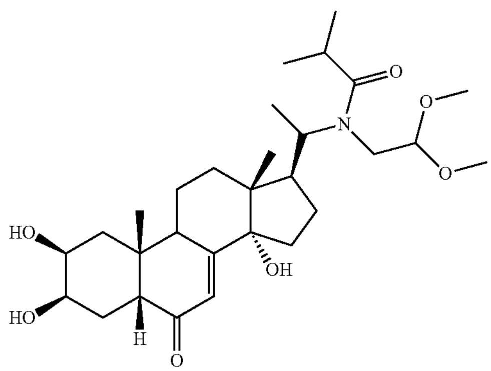 [SMILES: COC(CN(C(=O)C(C)C)C(C)[C@H]1CC[C@@]2(O)C3=CC(=O)[C@@H]4C[C@@H](O)[C@@H](O)C[C@]4(C)C3CC[C@]12C)OC] | N-(2,2-dimethoxyethyl)-2-methyl-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]propanamide |
| 67 | 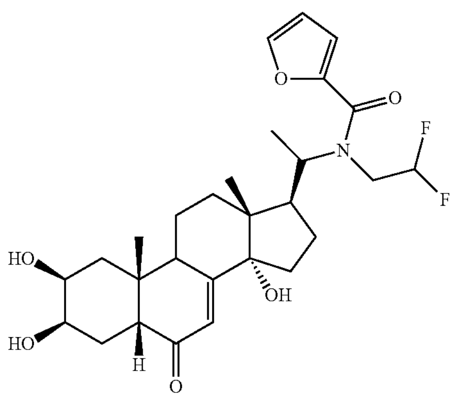 [SMILES: CC([C@H]1CC[C@@]2(O)C3=CC(=O)[C@@H]4C[C@@H](O)[C@@H](O)C[C@]4(C)C3CC[C@]12C)N(CC(F)F)C(=O)c1ccco1] | N-(2,2-difluoroethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]furan-2-carboxamide |
| 68 | 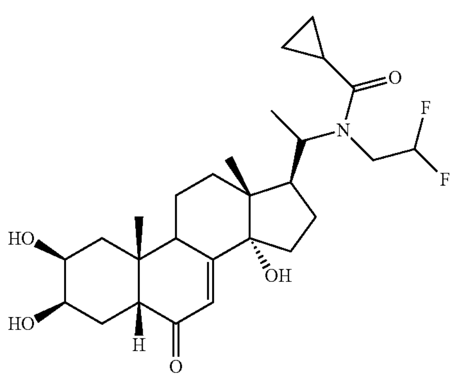 [SMILES: CC([C@H]1CC[C@@]2(O)C3=CC(=O)[C@@H]4C[C@@H](O)[C@@H](O)C[C@]4(C)C3CC[C@]12C)N(CC(F)F)C(=O)C1CC1] | N-(2,2-difluoroethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]cyclopropanecarboxamide |

TABLE 2-continued list of the compounds of which the synthesis is exemplified

| No. | Chemical structure | Chemical name |
| --- | --- | --- |
| 69 | 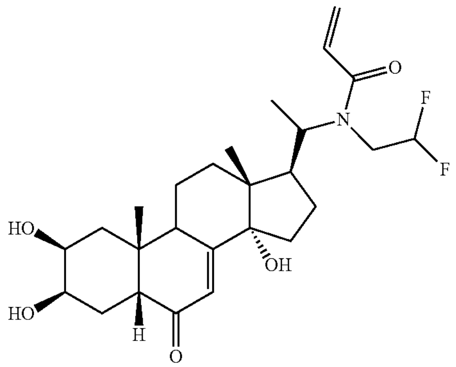 [SMILES: C=CC(=O)N(CC(F)F)C(C)[C@H]1CC[C@@]2(O)C3=CC(=O)[C@@H]4C[C@@H](O)[C@@H](O)C[C@]4(C)C3CC[C@]12C] | N-(2,2-difluoroethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]prop-2-enamide |
| 70 | 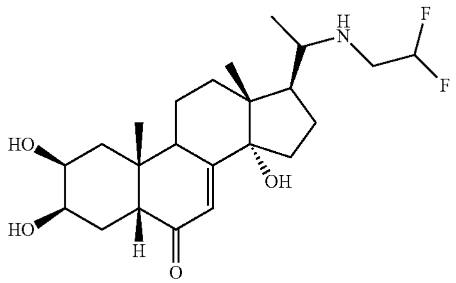 [SMILES: CC(NCC(F)F)[C@H]1CC[C@@]2(O)C3=CC(=O)[C@@H]4C[C@@H](O)[C@@H](O)C[C@]4(C)C3CC[C@]12C] | (2S,3R,5R,10R,13R,14S,17S)-17-[1-(2,2-difluoroethylamino)ethyl]-2,3,14-trihydroxy-10,13-dimethyl-2,3,4,5,9,11,12,15,16,17-decahydro-1H-cyclopenta[a]phenanthren-6-one |
| 71 | 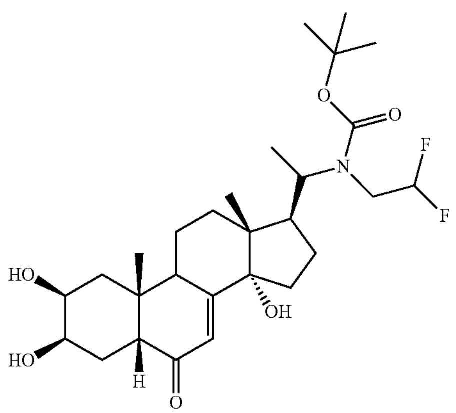 [SMILES: CC([C@H]1CC[C@@]2(O)C3=CC(=O)[C@@H]4C[C@@H](O)[C@@H](O)C[C@]4(C)C3CC[C@]12C)N(CC(F)F)C(=O)OC(C)(C)C] | Tert-butyl N-(2,2-difluoroethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]carbamate |
| 72 | 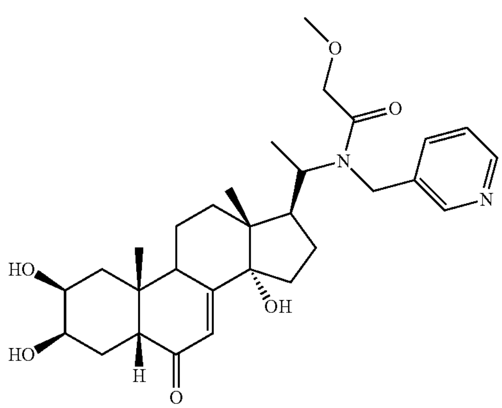 [SMILES: COCC(=O)N(Cc1cccnc1)C(C)[C@H]1CC[C@@]2(O)C3=CC(=O)[C@@H]4C[C@@H](O)[C@@H](O)C[C@]4(C)C3CC[C@]12C] | 2-methoxy-N-(3-pyridylmethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]acetamide |

TABLE 2-continued list of the compounds of which the synthesis is exemplified

| No. | Chemical structure | Chemical name |
|---|---|---|
| 73 | 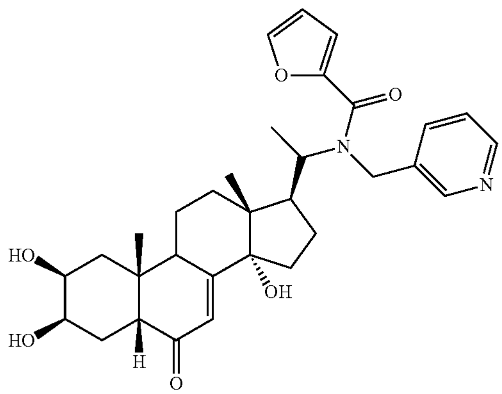 [SMILES: CC([C@H]1CC[C@@]2(O)C3=CC(=O)[C@@H]4C[C@@H](O)[C@@H](O)C[C@]4(C)C3CC[C@]12C)N(Cc1cccnc1)C(=O)c1ccco1] | N-(3-pyridylmethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta(a)phenanthren-17-yl]ethyl]furan-2-carboxamide |
| 74 | 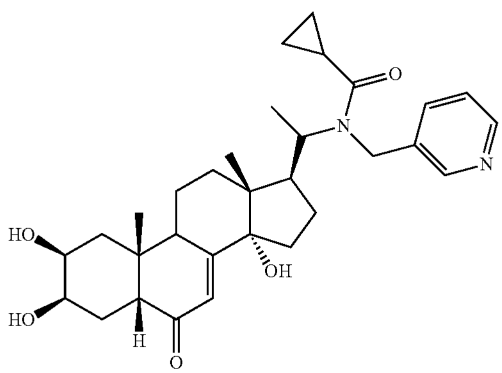 [SMILES: CC([C@H]1CC[C@@]2(O)C3=CC(=O)[C@@H]4C[C@@H](O)[C@@H](O)C[C@]4(C)C3CC[C@]12C)N(Cc1cccnc1)C(=O)C1CC1] | N-(3-pyridylmethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]cyclopropanecarboxamide |
| 75 | 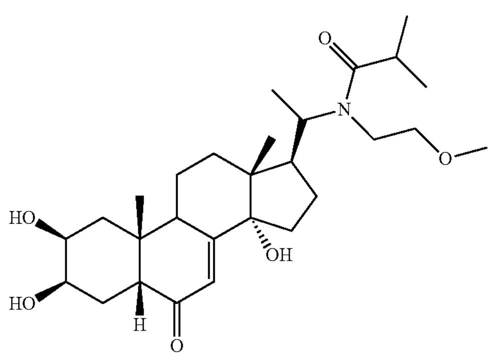 [SMILES: COCCN(C(=O)C(C)C)C(C)[C@H]1CC[C@@]2(O)C3=CC(=O)[C@@H]4C[C@@H](O)[C@@H](O)C[C@]4(C)C3CC[C@]12C] | N-(2-methoxyethyl)-2-methyl-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]propanamide |
| 76 | 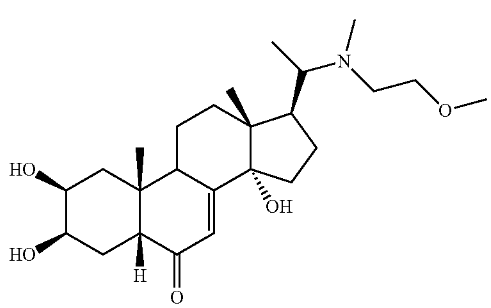 [SMILES: COCCN(C)C(C)[C@H]1CC[C@@]2(O)C3=CC(=O)[C@@H]4C[C@@H](O)[C@@H](O)C[C@]4(C)C3CC[C@]12C] | (2S,3R,5R,10R,13R,14S,17S)-2,3,14-trihydroxy-17-[1-(2-methoxyethyl(methyl)amino)ethyl]-10,13-dimethyl-2,3,4,5,9,11,12,15,16,17-decahydro-1H-cyclopenta[a]phenanthren-6-one |

TABLE 2-continued list of the compounds of which the synthesis is exemplified

| No. | Chemical structure | Chemical name |
|---|---|---|
| 77 | 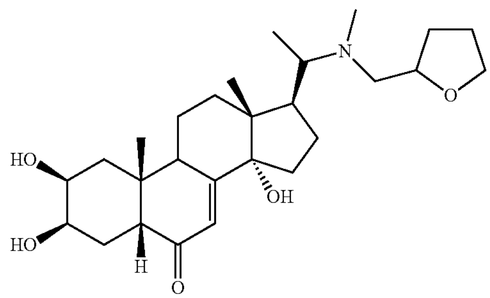 [SMILES: CC([C@H]1CC[C@@]2(O)C3=CC(=O)[C@@H]4C[C@@H](O)[C@@H](O)C[C@]4(C)C3CC[C@]12C)N(C)CC1CCCO1] | (2S,3R,5R,10R,13R,14S,17S)-2,3,14-trihydroxy-10,13-dimethyl-17-[1-(methyl(tetrahydrofuran-2-ylmethyl)amino)ethyl]-2,3,4,5,9,11,12,15,16,17-decahydro-1H-cyclopenta[a]phenanthren-6-one |
| 78 | 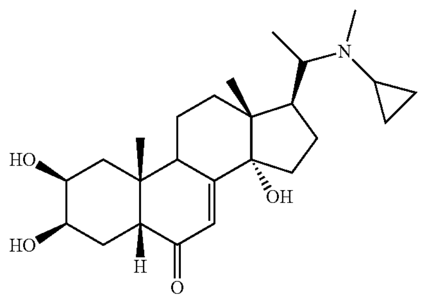 [SMILES: CC([C@H]1CC[C@@]2(O)C3=CC(=O)[C@@H]4C[C@@H](O)[C@@H](O)C[C@]4(C)C3CC[C@]12C)N(C)C1CC1] | (2S,3R,5R,10R,13R,14S,17S)-17-[1-(cyclopropyl(methyl)amino)ethyl]-2,3,14-trihydroxy-10,13-dimethyl-2,3,4,5,9,11,12,15,16,17-decahydro-1H-cyclopenta[a]phenanthren-6-one |
| 79 | 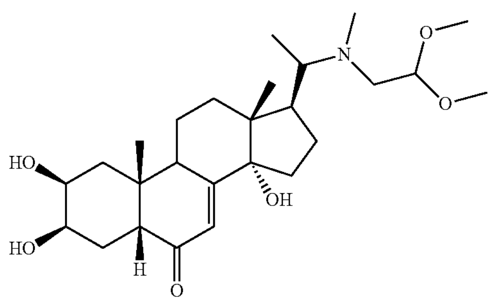 [SMILES: COC(CN(C)C(C)[C@H]1CC[C@@]2(O)C3=CC(=O)[C@@H]4C[C@@H](O)[C@@H](O)C[C@]4(C)C3CC[C@]12C)OC] | (2S,3R,5R,10R,13R,14S,17S)-17-[1-(2,2-dimethoxyethyl(methyl)amino)ethyl]-2,3,14-trihydroxy-10,13-dimethyl-2,3,4,5,9,11,12,15,16,17-decahydro-1H-cyclopenta[a]phenanthren-6-one |
| 80 | 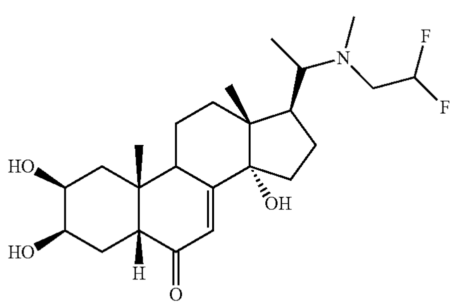 [SMILES: CC([C@H]1CC[C@@]2(O)C3=CC(=O)[C@@H]4C[C@@H](O)[C@@H](O)C[C@]4(C)C3CC[C@]12C)N(C)CC(F)F] | (2S,3R,5R,10R,13S,17S)-2,3-dihydroxy-10,13-dimethyl-17-[(E)-3-(1-methylpyrrol-2-yl)prop-2-enoyl]-1,2,3,4,5,9,11,12,14,15,16,17-dodecahydrocyclopenta[a]phenanthren-6-one |
| 81 | 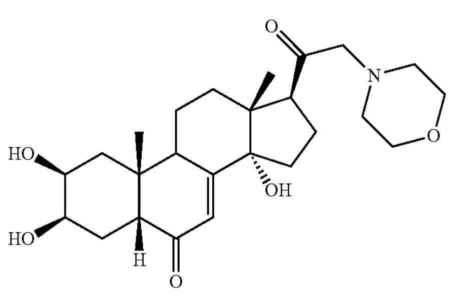 [SMILES: C[C@]12C[C@H](O)[C@H](O)C[C@H]1C(=O)C=C1C2CC[C@]2(C)[C@@H](C(=O)CN3CCOCC3)CC[C@@]12O] | (2S,3R,5R,10R,13R,14S,17S)-2,3,14-trihydroxy-10,13-dimethyl-17-(2-morpholinoacetyl)-2,3,4,5,9,11,12,15,16,17-decahydro-1H-cyclopenta[a]phenanthren-6-one |

TABLE 2-continued list of the compounds of which the synthesis is exemplified

| No. | Chemical structure | Chemical name |
|---|---|---|
| 82 | 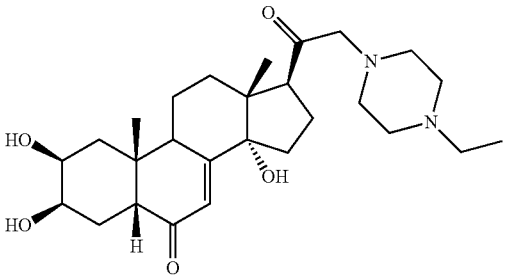 [SMILES: CCN1CCN(CC(=O)[C@H]2CC[C@@]3(O)C4=CC(=O)[C@@H]5C[C@@H](O)[C@@H](O)C[C@]5(C)C4CC[C@]23C)CC1] | (2S,3R,5R,10R,13R,14S,17S)-17-[2-(4-ethylpiperazin-1-yl)acetyl]-2,3,14-trihydroxy-10,13-dimethyl-2,3,4,5,9,11,12,15,16,17-decahydro-1H-cyclopenta[a]phenanthren-6-one |
| 83 | 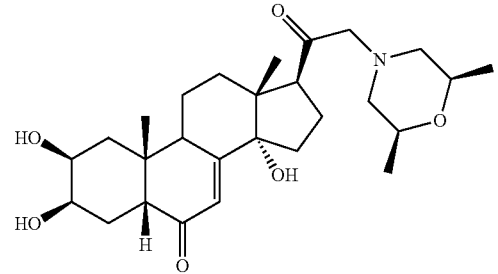 [SMILES: C[C@@H]1CN(CC(=O)[C@H]2CC[C@@]3(O)C4=CC(=O)[C@@H]5C[C@@H](O)[C@@H](O)C[C@]5(C)C4CC[C@]23C)C[C@H](C)O1] | (2S,3R,5R,10R,13R,14S,17S)-17-[2-[(2S,6R)-2,6-dimethylmorpholin-4-yl]acetyl]-2,3,14-trihydroxy-10,13-dimethyl-2,3,4,5,9,11,12,15,16,17-decahydro-1H-cyclopenta[a]phenanthren-6-one |
| 84 | 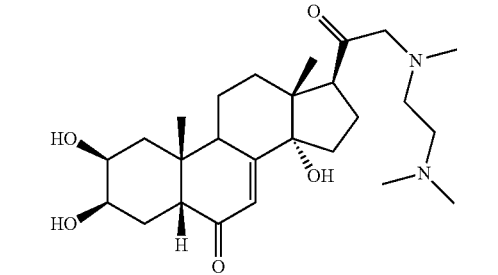 [SMILES: CN(C)CCN(C)CC(=O)[C@H]1CC[C@@]2(O)C3=CC(=O)[C@@H]4C[C@@H](O)[C@@H](O)C[C@]4(C)C3CC[C@]12C] | (2S,3R,5R,10R,13R,14S,17S)-17-[2-(2-dimethylaminoethyl(methyl)amino)acetyl]-2,3,14-trihydroxy-10,13-dimethyl-2,3,4,5,9,11,12,15,16,17-decahydro-1H-cyclopenta[a]phenanthren-6-one |
| 85 | 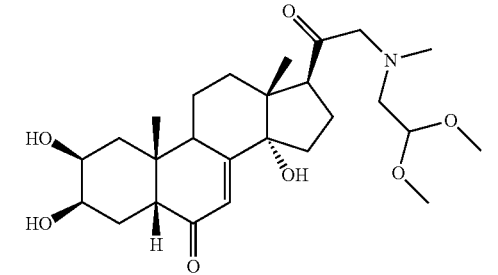 [SMILES: COC(CN(C)CC(=O)[C@H]1CC[C@@]2(O)C3=CC(=O)[C@@H]4C[C@@H](O)[C@@H](O)C[C@]4(C)C3CC[C@]12C)OC] | (2S,3R,5R,10R,13R,14S,17S)-17-[2-(2,2-dimethoxyethyl(methyl)amino)acetyl]-2,3,14-trihydroxy-10,13-dimethyl-2,3,4,5,9,11,12,15,16,17-decahydro-1H-cyclopenta[a]phenanthren-6-one |
| 86 | 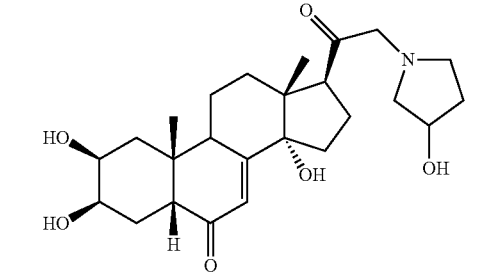 [SMILES: C[C@]12C[C@H](O)[C@H](O)C[C@H]1C(=O)C=C1C2CC[C@]2(C)[C@@H](C(=O)CN3CCC(O)C3)CC[C@@]12O] | (2S,3R,5R,10R,13R,14S,17S)-2,3,14-trihydroxy-17-[2-(3-hydroxypyrrolidin-1-yl)acetyl]-10,13-dimethyl-2,3,4,5,9,11,12,15,16,17-decahydro-1H-cyclopenta[a]phenanthren-6-one |

TABLE 2-continued list of the compounds of which the synthesis is exemplified

| No. | Chemical structure | Chemical name |
| --- | --- | --- |
| 87 | 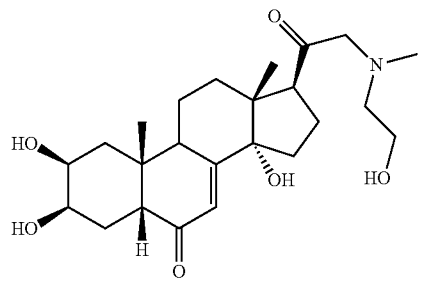 [SMILES: CN(CCO)CC(=O)[C@H]1CC[C@@]2(O)C3=CC(=O)[C@@H]4C[C@@H](O)[C@@H](O)C[C@]4(C)C3CC[C@]12C] | (2S,3R,5R,10R,13R,14S,17S)-2,3,14-trihydroxy-17-[2-(2-hydroxyethyl(methyl)amino)acetyl]-10,13-dimethyl-2,3,4,5,9,11,12,15,16,17-decahydro-1H-cyclopenta[a]phenanthren-6-one |
| 88 | 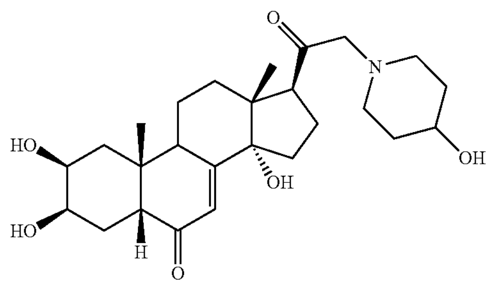 [SMILES: C[C@]12C[C@H](O)[C@H](O)C[C@H]1C(=O)C=C1C2CC[C@]2(C)[C@@H](C(=O)CN3CCC(O)CC3)CC[C@@]12O] | (2S,3R,5R,10R,13R,14S,17S)-2,3,14-trihydroxy-17-[2-(4-hydroxy-1-piperidyl)acetyl]-10,13-dimethyl-2,3,4,5,9,11,12,15,16,17-decahydro-1H-cyclopenta[a]phenanthren-6-one |
| 89 | 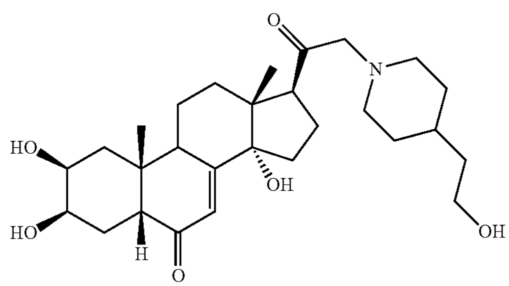 [SMILES: C[C@]12C[C@H](O)[C@H](O)C[C@H]1C(=O)C=C1C2CC[C@]2(C)[C@@H](C(=O)CN3CCC(CCO)CC3)CC[C@@]12O] | (2S,3R,5R,10R,13R,14S,17S)-2,3,14-trihydroxy-17-[2-[4-(2-hydroxyethyl)-1-piperidyl]acetyl]-10,13-dimethyl-2,3,4,5,9,11,12,15,16,17-decahydro-1H-cyclopenta[a]phenanthren-6-one |
| 90 | 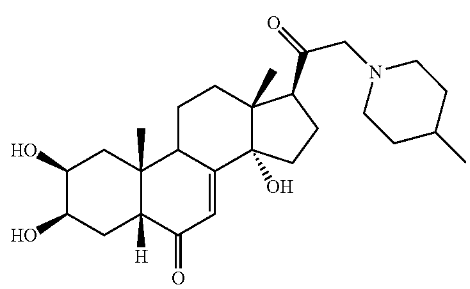 [SMILES: CC1CCN(CC(=O)[C@H]2CC[C@@]3(O)C4=CC(=O)[C@@H]5C[C@@H](O)[C@@H](O)C[C@]5(C)C4CC[C@]23C)CC1] | (2S,3R,5R,10R,13R,14S,17S)-2,3,14-trihydroxy-10,13-dimethyl-17-[2-(4-methyl-1-piperidyl)acetyl]-2,3,4,5,9,11,12,15,16,17-decahydro-1H-cyclopenta[a]phenanthren-6-one |
| 91 | 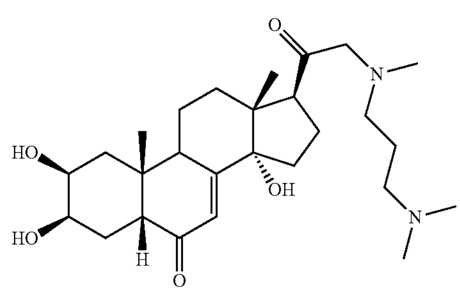 [SMILES: CN(C)CCCN(C)CC(=O)[C@H]1CC[C@@]2(O)C3=CC(=O)[C@@H]4C[C@@H](O)[C@@H](O)C[C@]4(C)C3CC[C@]12C] | (2S,3R,5R,10R,13R,14S,17S)-17-[2-(3-dimethylaminopropyl(methyl)amino)acetyl]-2,3,14-trihydroxy-10,13-dimethyl-2,3,4,5,9,11,12,15,16,17-decahydro-1H-cyclopenta[a]phenanthren-6-one |

TABLE 2-continued list of the compounds of which the synthesis is exemplified

| No. | Chemical structure | Chemical name |
|---|---|---|
| 92 | 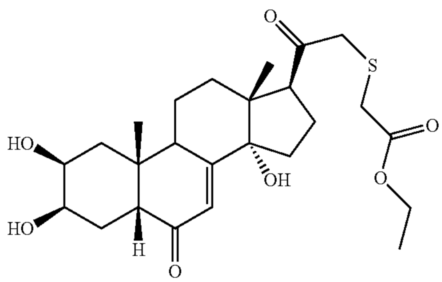 [SMILES: CCOC(=O)CSCC(=O)[C@H]1CC[C@@]2(O)C3=CC(=O)[C@@H]4C[C@@H](O)[C@@H](O)C[C@]4(C)C3CC[C@]12C] | Ethyl 2-[2-oxo-2-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]sulfanylacetate |
| 93 | 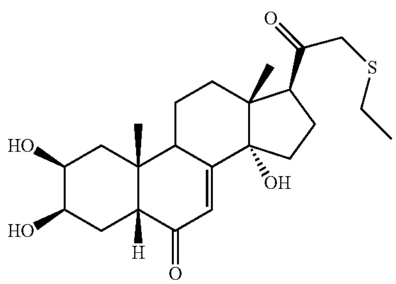 [SMILES: CCSCC(=O)[C@H]1CC[C@@]2(O)C3=CC(=O)[C@@H]4C[C@@H](O)[C@@H](O)C[C@]4(C)C3CC[C@]12C] | (2S,3R,5R,10R,13R,14S,17S)-17-(2-ethylsulfanylacetyl)-2,3,14-trihydroxy-10,13-dimethyl-2,3,4,5,9,11,12,15,16,17-decahydro-1H-cyclopenta[a]phenanthren-6-one |
| 94 | 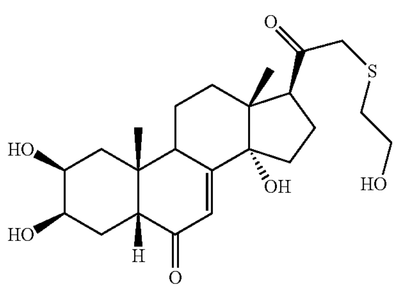 [SMILES: C[C@]12C[C@H](O)[C@H](O)C[C@H]1C(=O)C=C1C2CC[C@]2(C)[C@@H](C(=O)CSCCO)CC[C@@]12O] | (2S,3R,5R,10R,13R,14S,17S)-2,3,14-trihydroxy-17-[2-(2-hydroxyethylsulfanyl)acetyl]-10,13-dimethyl-2,3,4,5,9,11,12,15,16,17-decahydro-1H-cyclopenta[a]phenanthren-6-one |
| 95 | 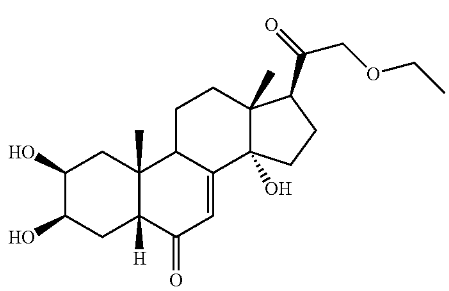 [SMILES: CCOCC(=O)[C@H]1CC[C@@]2(O)C3=CC(=O)[C@@H]4C[C@@H](O)[C@@H](O)C[C@]4(C)C3CC[C@]12C] | (2S,3R,5R,10R,13R,14S,17S)-17-(2-ethoxyacetyl)-2,3,14-trihydroxy-10,13-dimethyl-2,3,4,5,9,11,12,15,16,17-decahydro-1H-cyclopenta[a]phenanthren-6-one |
| 96 | 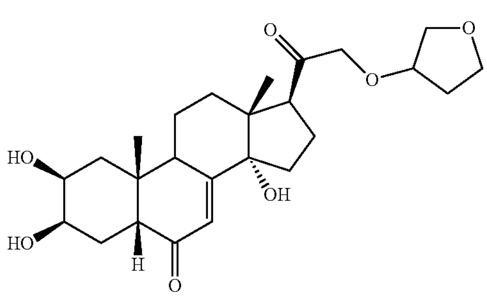 [SMILES: C[C@]12C[C@H](O)[C@H](O)C[C@H]1C(=O)C=C1C2CC[C@]2(C)[C@@H](C(=O)COC3CCOC3)CC[C@@]12O] | (2S,3R,5R,10R,13R,14S,17S)-2,3,14-trihydroxy-10,13-dimethyl-17-(2-tetrahydrofuran-3-yloxyacetyl)-2,3,4,5,9,11,12,15,16,17-decahydro-1H-cyclopenta[a]phenanthren-6-one |

TABLE 2-continued list of the compounds of which the synthesis is exemplified

| No. | Chemical structure | Chemical name |
|---|---|---|
| 97 | 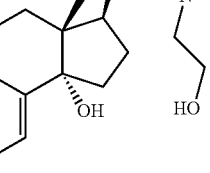 | (2S,3R,5R,10R,13R,14S,17S)-2,3,14-trihydroxy-17-[1-hydroxy-2-(2-hydroxyethyl(methyl)amino)ethyl]-10,13-dimethyl-2,3,4,5,9,11,12,15,16,17-decahydro-1H-cyclopenta[a]phenanthren-6-one |
| 98 | 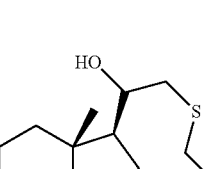 | (2S,3R,5R,10R,13R,14S,17S)-2,3,14-trihydroxy-17-[1-hydroxy-2-(2-hydroxyethylsulfanyl)ethyl]-10,13-dimethyl-2,3,4,5,9,11,12,15,16,17-decahydro-1H-cyclopenta[a]phenanthren-6-one |
| 99 | 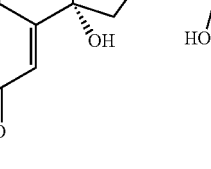 | (2S,3R,5R,10R,13R,14S,17S)-2,3,14-trihydroxy-17-[1-hydroxy-2-[4-(2-hydroxyethyl)-1-piperidyl]ethyl]-10,13-dimethyl-2,3,4,5,9,11,12,15,16,17-decahydro-1H-cyclopenta[a]phenanthren-6-one |
| 100 | 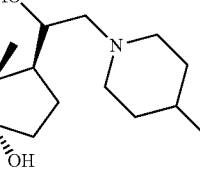 | (2S,3R,5R,10R,13R,14S,17S)-2,3,14-trihydroxy-17-[1-hydroxy-2-(3-hydroxypyrrolidin-1-yl)ethyl]-10,13-dimethyl-2,3,4,5,9,11,12,15,16,17-decahydro-1H-cyclopenta[a]phenanthren-6-one |
| 101 | 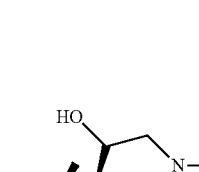 | (2S,3R,5R,10R,13R,14S,17S)-17-(2-bromoacetyl)-2,3,14-trihydroxy-10,13-dimethyl-2,3,4,5,9,11,12,15,16,17-decahydro-1H-cyclopenta[a]phenanthren-6-one |

TABLE 2-continued list of the compounds of which the synthesis is exemplified

| No. | Chemical structure | Chemical name |
|---|---|---|
| 102 | 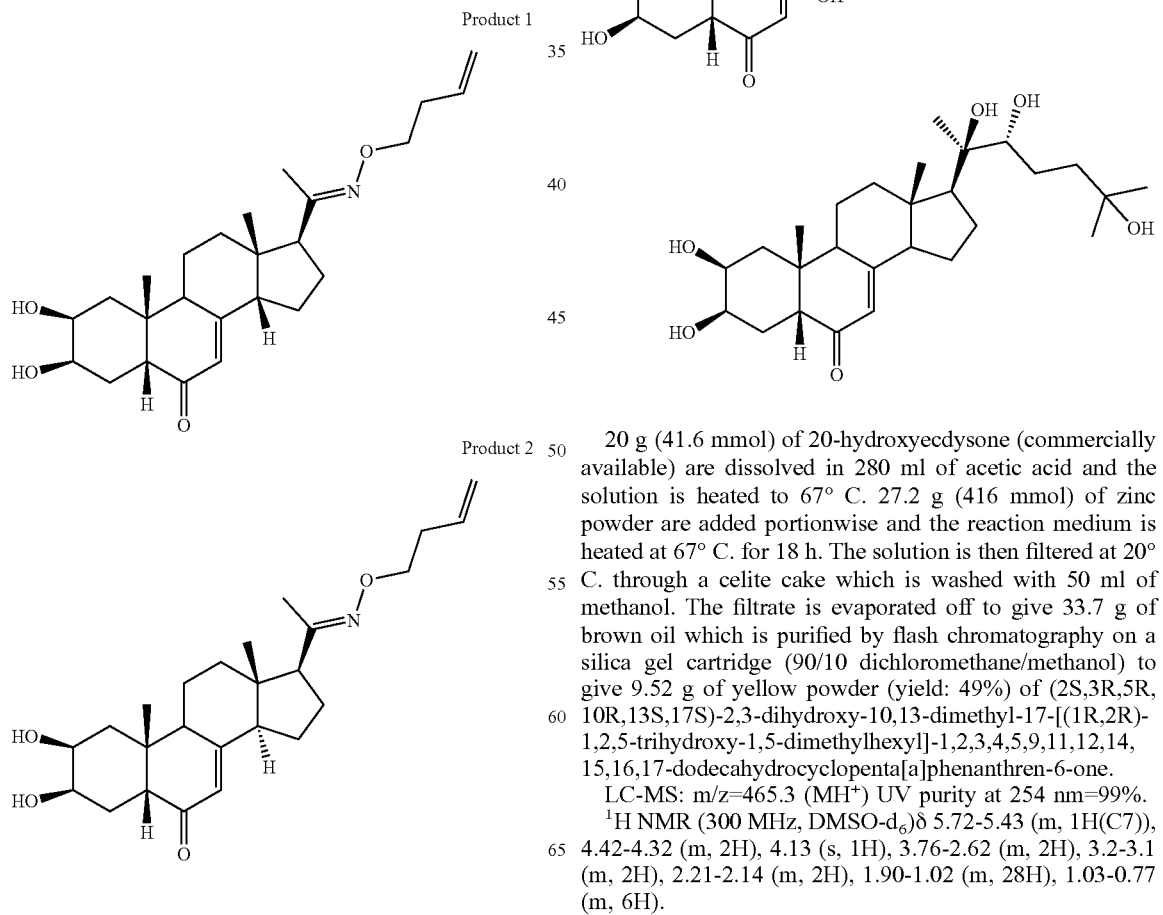 | (2S,3R,5R,10R,13R,14S,17S)-17-(2-bromoacetyl)-2,3,14-trihydroxy-10,13-dimethyl-2,3,4,5,9,11,12,15,16,17-decahydro-1H-cyclopenta[a]phenanthren-6-one |

Example 1

Scheme A

Preparation of Compounds No. 1 and No. 2: (2S,3R,5R,10R,13S,14S,17S)-17-(N-but-3-enoxy-C-methylcarbonimidoyl)-2,3-dihydroxy-10,13-dimethyl-1,2,3,4,5,9,11,12,14,15,16,17-dodecahydrocyclopenta[a]phenanthren-6-one and (2S,3R,5R,10R,13S,14R,17S)-17-(N-but-3-enoxy-C-methylcarbonimidoyl)-2,3-dihydroxy-10,13-dimethyl-1,2,3,4,5,9,11,12,14,15,16,17-dodecahydrocyclopenta[a]phenanthren-6-one Product 1

Product 2

Step 1: Preparation of (2S,3R,5R,10R,13S,17S)-2,3-dihydroxy-10,13-dimethyl-17-[(1R,2R)-1,2,5-trihydroxy-1,5-dimethylhexyl]-1,2,3,4,5,9,11,12,14,15,16,17-dodecahydrocyclopenta[a]phenanthren-6-one 20 g (41.6 mmol) of 20-hydroxyecdysone (commercially available) are dissolved in 280 ml of acetic acid and the solution is heated to 67° C. 27.2 g (416 mmol) of zinc powder are added portionwise and the reaction medium is heated at 67° C. for 18 h. The solution is then filtered at 20° C. through a celite cake which is washed with 50 ml of methanol. The filtrate is evaporated off to give 33.7 g of brown oil which is purified by flash chromatography on a silica gel cartridge (90/10 dichloromethane/methanol) to give 9.52 g of yellow powder (yield: 49%) of (2S,3R,5R,10R,13S,17S)-2,3-dihydroxy-10,13-dimethyl-17-[(1R,2R)-1,2,5-trihydroxy-1,5-dimethylhexyl]-1,2,3,4,5,9,11,12,14,15,16,17-dodecahydrocyclopenta[a]phenanthren-6-one.

LC-MS: m/z=465.3 (MH$^+$) UV purity at 254 nm=99%.
$^1$H NMR (300 MHz, DMSO-d$_6$)δ 5.72-5.43 (m, 1H(C7)), 4.42-4.32 (m, 2H), 4.13 (s, 1H), 3.76-2.62 (m, 2H), 3.2-3.1 (m, 2H), 2.21-2.14 (m, 2H), 1.90-1.02 (m, 28H), 1.03-0.77 (m, 6H).

Step 2: Preparation of (2S,3R,5R,10R,13S,17S)-17-acetyl-2,3-dihydroxy-10,13-dimethyl-1,2,3,4,5,9,11,12,14,15,16,17-dodecahydrocyclopenta[a]phenanthren-6-one

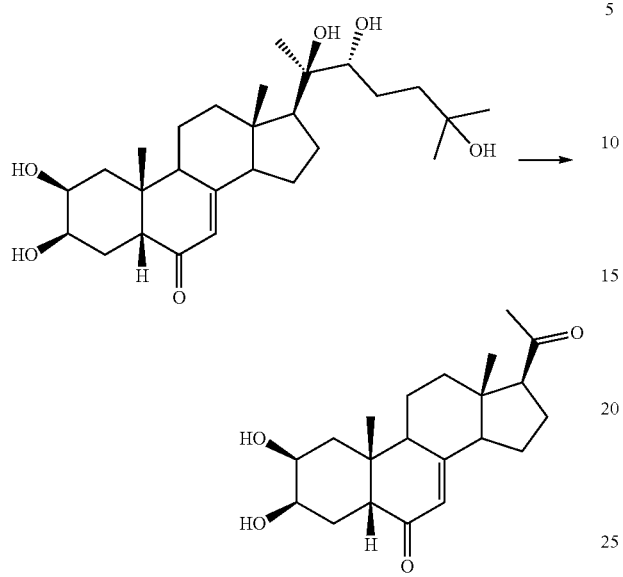

9.52 g (20.28 mmol) of (2S,3R,5R,10R,13S,17S)-2,3-dihydroxy-10,13-dimethyl-17-[(1R,2R)-1,2,5-trihydroxy-1,5-dimethylhexyl]-1,2,3,4,5,9,11,12,14,15,16,17-dodecahydrocyclopenta[a]phenanthren-6-one are dissolved in 46 ml of pyridine and 276 ml of dichloromethane. 6.69 g (30.4 mmol) of pyridinium chlorochromate are added portionwise over the course of 10 min and the reaction medium is stirred at 20° C. for 2 h 30. The pyridine and the dichloromethane are then evaporated off under vacuum and the residue is purified by flash chromatography on a silica gel cartridge (95/5 dichloromethane/methanol) to give 4 g of beige powder (yield: 56%) of (2S,3R,5R,10R,13S,17S)-17-acetyl-2,3-dihydroxy-10,13-dimethyl-1,2,3,4,5,9,11,12,14,15,16,17-dodecahydrocyclopenta[a]phenanthren-6-one.

LC-MS: m/z=347.2 (MH+) UV purity at 254 nm=99%.
$^1$H NMR (300 MHz, DMSO-d$_6$) δ 5.68-5.46 (m, 1H(C7)), 4.41-4.37 (m, 2H), 3.76-3.55 (m, 2H), 2.83-2.54 (m, 2H), 2.33-1.95 (m, 6H), 1.90-1.30 (m, 10H), 1.28-1.18 (m, 1H), 0.88-0.42 (m, 6H).

Step 3: Preparation of the epimers (2S,3R,5R,10R,13S,14S,17S)-17-(N-but-3-enoxy-C-methylcarbonimidoyl)-2,3-dihydroxy-10,13-dimethyl-1,2,3,4,5,9,11,12,14,15,16,17-dodecahydrocyclopenta[a]phenanthren-6-one and (2S,3R,5R,10R,13S,14R,17S)-17-(N-but-3-enoxy-C-methylcarbonimidoyl)-2,3-dihydroxy-10,13-dimethyl-1,2,3,4,5,9,11,12,14,15,16,17-dodecahydrocyclopenta[a]phenanthren-6-one

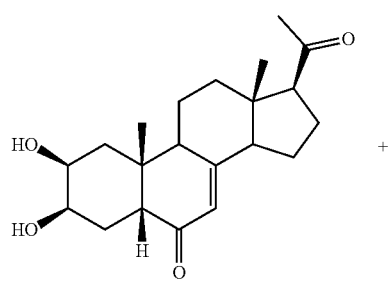

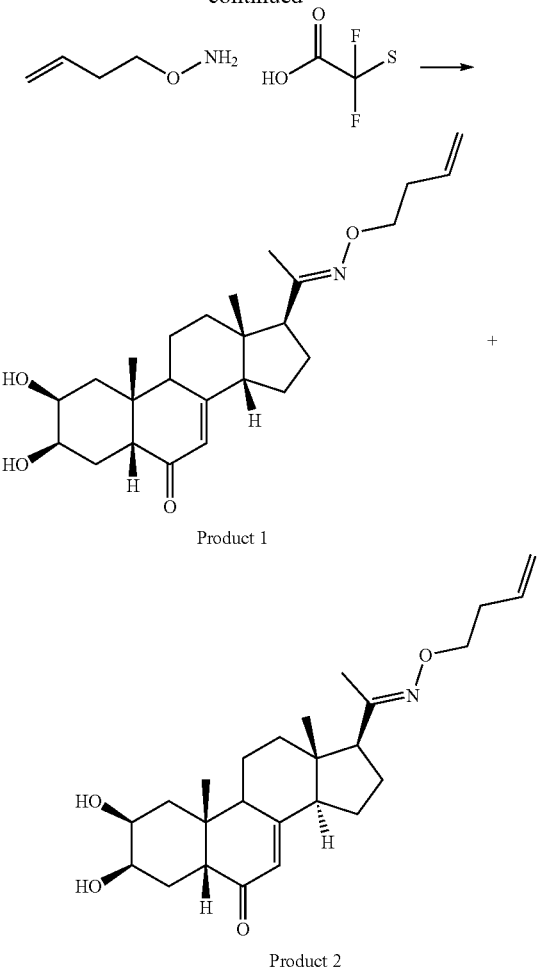

Product 1

Product 2

328 mg (0.947 mmol) of (2S,3R,5R,10R,13S,17S)-17-acetyl-2,3-dihydroxy-10,13-dimethyl-1,2,3,4,5,9,11,12,14,15,16,17-dodecahydrocyclopenta[a]phenanthren-6-one (14-deoxypoststerone) prepared in step 2 are dissolved in 1.2 ml of ethanol and 200 mg (0.994 mmol) of but-3-enoxyammonium 2,2,2-trifluoroacetate are added portionwise. The reaction medium is brought to reflux for 20 h. The solvent is evaporated off and the residue is purified by preparative chromatography on a C18 column (60/40 acetonitrile/water) to give 24 mg of beige powder (yield: 6%) of compound No. 1 (2S,3R,5R,10R,13S,14S,17S)-17-(N-but-3-enoxy-C-methylcarbonimidoyl)-2,3-dihydroxy-10,13-dimethyl-1,2,3,4,5,9,11,12,14,15,16,17-dodecahydrocyclopenta[a]phenanthren-6-one and 57 mg of beige powder (yield: 14%) of compound No. 2 (2S,3R,5R,10R,13S,14R,17S)-17-(N-but-3-enoxy-C-methylcarbonimidoyl)-2,3-dihydroxy-10,13-dimethyl-1,2,3,4,5,9,11,12,14,15,16,17-dodecahydrocyclopenta[a]phenanthren-6-one.

Compound No. 1:
LC-MS: m/z=416.2 (MH+) UV purity at 254 nm=99%.
$^1$H NMR (300 MHz, DMSO-d$_6$)—C14 beta epimer—δ 5.83-5.72 (m, 1H), 5.70 (s, 1H(C7)), 5.1-5 (m, 2H), 4.40-4.36 (m, 2H), 4 (t, 2H), 3.77-3.71 (m, 2H), 2.80-2.60 (m, 1H), 2.40-1.20 (m, 20H), 0.82-0.74 (m, 6H).

Compound No. 2:
LC-MS: m/z=416.2 (MH+) UV purity at 254 nm=99%.
$^1$H NMR (300 MHz, DMSO-D6)—C14 alpha epimer—δ 5.87-5.72 (m, 1H), 5.48 (s, 1H(C7)), 5.1-4.9 (m, 2H), 4.40-4.36 (m, 2H), 4 (t, 2H), 3.77-3.71 (m, 2H), 2.80-2.60 (m, 1H), 2.44-1.23 (m, 20H), 0.83 (s, 3H), 0.47 (s, 3H).

Compounds Nos. 3 to 6 were prepared according to the same scheme, in the form of C14 alpha and C14 beta epimers.

| No. | MW g/mol | Appearance | Purity[1] (%) | MS m/z MH+ | $^1$H NMR (300 MHz, DMSO-$d_6$) δ |
|---|---|---|---|---|---|
| 3 | 492.6 | beige powder | 92 | 493.2 | 8.56 (s, 1H), 7.78 (s, 1H), 6.34-5.47 (m, 1H(C7)), 4.48 (m, 4H), 3.72 (m, 3H), 2.28-1.30 (m, 20H), 0.85-0.44 (m, 6H) |
| 4 | 419.5 | beige powder | 92 | 420.2 | 5.69-5.46 (m, 1H(C7)), 4.43 (s, 2H), 3.74-3.64 (m, 3H), 2.80-2.60 (m, 1H), 2.31-1.16 (m, 19H), 0.85-0.44 (m, 6H) |
| 5 | 389.5 | white powder | 94 | 390.2 | 5.70-5.47(m, 1H(C7)), 4.39-4.36(m, 2H), 4.02-3.95(q, 2H), 3.76-3.60(m, 2H), 2.80-2.60(m, 1H), 2.41-1.2(m, 18H), 1.15(t, 3H), 0.83-0.47(m, 6H) |
| 6 | 361.5 | white powder | 93 | 362.2 | 10.44-10.39 (m, 1H), 5.67-5.47 (m, 1H(C7)), 4.37-4.35 (m, 2H), 3.75-3.60 (m, 2H), 2.80-2.60 (m, 1H), 2.45-1.1 (m, 18H), 0.83-0.45 (m, 6H) |

[1]LCMS purity, UV at 254 nm

Example 2

Scheme B

Preparation of Compound No. 7: [1-[(2S,3R,5R,6Z,10R,13R,17S)-2,3-dihydroxy-6-methoxyimino-10,13-dimethyl-1,2,3,4,5,9,11,12,16,17-decahydrocyclopenta[a]phenanthren-17-yl]ethanone oxime] and Compound No. 19: [(2S,3R,5R,6E,10R,13R,14S,17S)-17-(N-(2-methoxyethoxy)-C-methylcarbonimidoyl)-6-methoxyimino-10,13-dimethyl-2,3,4,5,9,11,12,15,16,17-decahydro-1H-cyclopenta[a]phenanthrene-2,3,14-triol]

Preparation of Compound No. 7

Step 1: Preparation of Compound (a) [(2S,3R,5R,6E,10R,13R,14S,17S)-6-methoxyimino-10,13-dimethyl-17-[(1R,2R)-1,2,5-trihydroxy-1,5-dimethylhexyl]-2,3,4,5,9,11,12,15,16,17-decahydro-1H-cyclopenta[a]phenanthrene-2,3,14-triol] and of Compound (b) [(2R,3R)-2-[(2S,3R,5R,6Z,10R,13R,17S)-2,3-dihydroxy-6-methoxyimino-10,13-dimethyl-1,2,3,4,5,9,11,12,16,17-decahydrocyclopenta[a]phenanthren-17-yl]-6-methylheptane-2,3,6-triol]

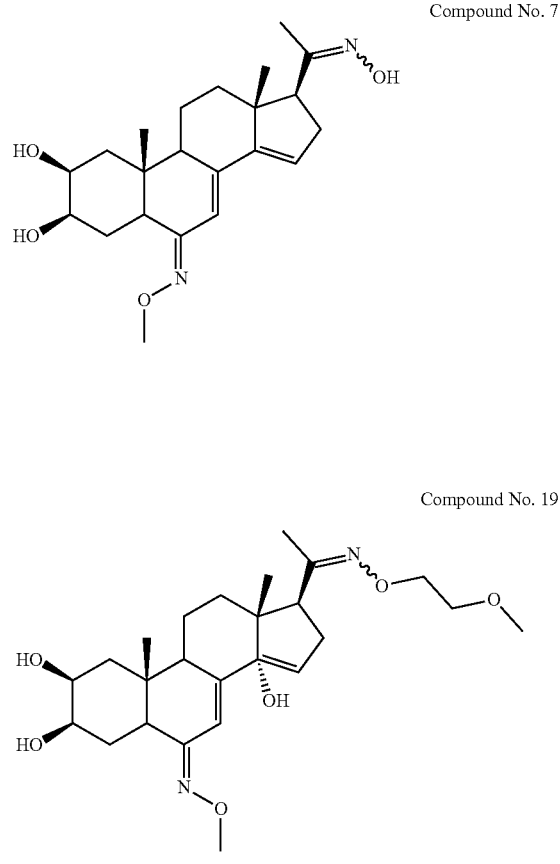

Compound No. 7

Compound No. 19

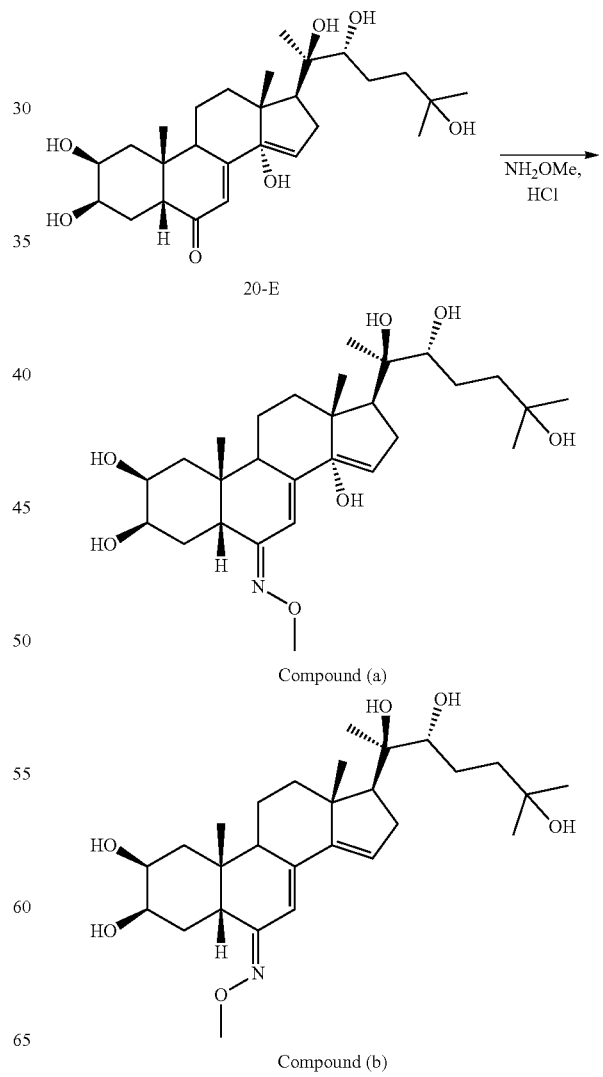

20-E

Compound (a)

Compound (b)

-continued

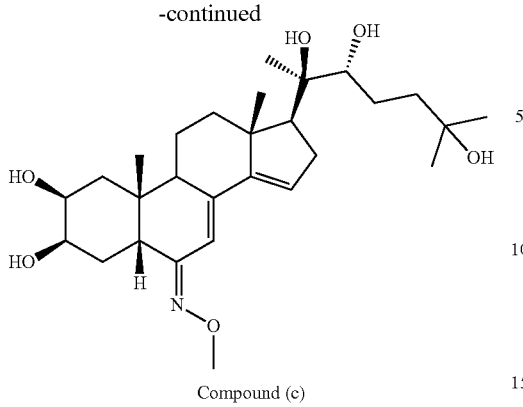

Compound (c)

According to the same procedure as that described in step 3 of scheme A, 788 mg of beige powder (yield: 37%) of compound (a) [(2S,3R,5R,6E,10R,13R,14S,17S)-6-methoxyimino-10,13-dimethyl-17-[(1R,2R)-1,2,5-trihydroxy-1,5-dimethylhexyl]-2,3,4,5,9,11,12,15,16,17-decahydro-1H-cyclopenta[a]phenanthrene-2,3,14-triol] were prepared from 20-hydroxyecdysone and from O-methylhydroxylamine hydrochloride. 667 mg (yield: 32%) of elimination compound (b) [(2R,3R)-2-[(2S,3R,5R,6Z,10R,13R,17S)-2,3-dihydroxy-6-methoxyimino-10,13-dimethyl-1,2,3,4,5,9,11,12,16,17-decahydrocyclopenta[a]phenanthren-17-yl]-6-methylheptane-2,3,6-triol] could also be isolated, and also 34 mg (yield: 2%) of elimination compound (c) [(2R,3R)-2-[(2S,3R,5R,6E,10R,13R,17S)-2,3-dihydroxy-6-methoxyimino-10,13-dimethyl-1,2,3,4,5,9,11,12,16,17-decahydrocyclopenta[a]phenanthren-17-yl]-6-methylheptane-2,3,6-triol] could also be likewise isolated.

Compound (a):

LC-MS: m/z=510.2 (MH$^+$) UV purity at 254 nm=99%.

$^1$H NMR (300 MHz, DMSO-d$_6$)δ 6.25 (s, 1H(C7)), 4.45-4.35 (m, 3H), 4.31-4.29 (m, 1H), 4.14 (s, 1H), 3.74-3.69 (m, 4H), 3.6-3.5 (m, 1H), 3.17-3.08 (m, 1H), 2.87-2.75 (m, 1H), 2.26-2.20 (m, 2H), 2.05-1.1 (m, 15H), 1.1-0.98 (m, 11H), 0.73 (s, 6H).

Compound (b):

LC-MS: m/z=492.2 (MH$^+$) UV purity at 254 nm=99%.

$^1$H NMR (300 MHz, DMSO-d$_6$) δ 6.04 (s, 1H), 5.77 (s, 1H), 4.45-4.30 (m, 2H), 4.25 (s, 1H), 4.11 (s, 1H), 3.75-3.65 (m, 5H), 3.63-3.55 (m, 1H), 3.20-3.08 (m, 2H), 2.17-1.90 (m, 3H), 1.70-1.20 (m, 11H), 1.15-0.93 (m, 14H), 0.74 (s, 3H).

Compound (c):

LC-MS: m/z=492.2 (MH$^+$) UV purity at 254 nm=99%.

$^1$H NMR (300 MHz, DMSO-d$_6$)δ 6.55 (s, 1H), 5.81 (s, 1H), 4.44-4.26 (m, 3H), 4.09 (s, 1H), 3.79-3.67 (m, 5H), 3.62-3.54 (m, 1H), 3.16-3.08 (m, 1H), 2.30-1.90 (m, 4H), 1.70-1.20 (m, 11H), 1.15-0.92 (m, 14H), 0.73 (s, 3H).

Starting from the Isolated Compound (b):

Step 2a: Preparation of Compound (d): [1-[(2S,3R,5R,6Z,10R,13R,17S)-2,3-dihydroxy-6-methoxyimino-10,13-dimethyl-1,2,3,4,5,9,11,12,16,17-decahydrocyclopenta[a]phenanthren-17-yl]ethanone]

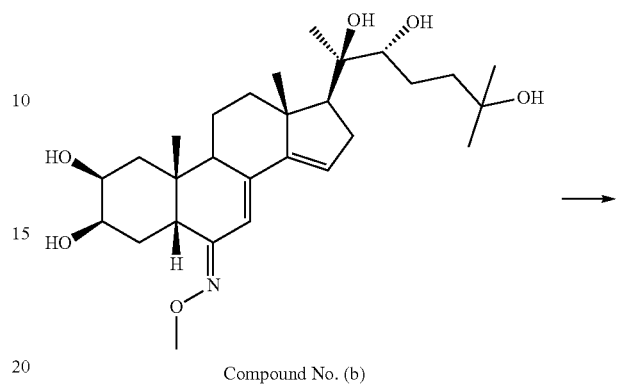

Compound No. (b)

Compound No. (d)

According to the same procedure as that described in step 2 of scheme A, 267 mg of beige powder (yield: 55%) of compound (d) [1-[(2S,3R,5R,6Z,10R,13R,17S)-2,3-dihydroxy-6-methoxyimino-10,13-dimethyl-1,2,3,4,5,9,11,12,16,17-decahydrocyclopenta[a]phenanthren-17-yl]ethanone] were prepared from compound (b).

Compound (d):

LC-MS: m/z=374.2 (MH$^+$) UV purity at 254 nm=99%.

$^1$H NMR (300 MHz, DMSO-d$_6$) δ 6.09 (s, 1H), 5.81-5.75 (m, 1H), 4.39-4.37 (m, 1H), 4.30-4.26 (m, 1H), 3.76 (s, 3H), 3.72-3.68 (m, 1H), 3.65-3.55 (m, 1H), 3.2-3 (m, 2H), 2.75-2.60 (m, 1H), 2.29-2.10 (m, 5H), 1.74-1.23 (m, 8H), 0.74-0.70 (m, 6H).

Step 3a: Preparation of Compound No. 7: [1-[(2S,3R,5R,6Z,10R,13R,17S)-2,3-dihydroxy-6-methoxyimino-10,13-dimethyl-1,2,3,4,5,9,11,12,16,17-decahydrocyclopenta[a]phenanthren-17-yl]ethanone oxime]

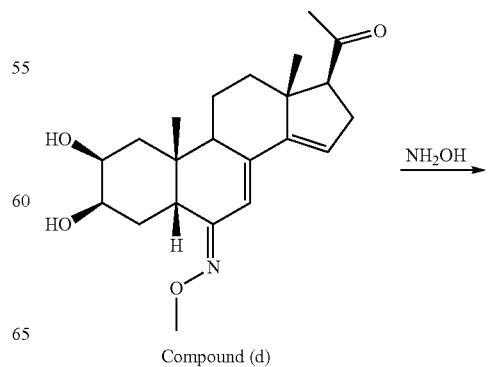

Compound (d)

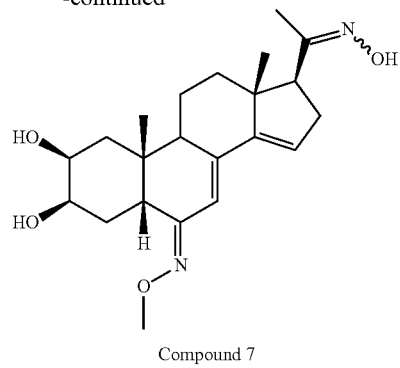

Compound 7

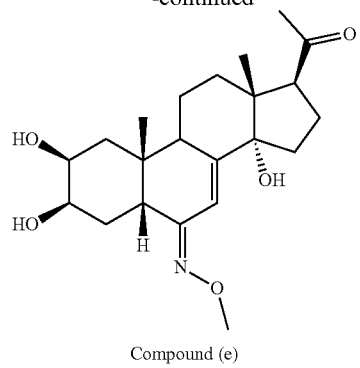

Compound (e)

According to the same procedure as that described in step 3 of scheme A, 81 mg of white powder (yield: 71%) of 1-[(2S,3R,5R,6Z,10R,13R,17S)-2,3-dihydroxy-6-methoxyimino-10,13-dimethyl-1,2,3,4,5,9,11,12,16,17-decahydrocyclopenta[a]phenanthren-17-yl]ethanone oxime were prepared from compound (d).

Compound No. 7:

LC-MS: m/z=389.2 (MH$^+$) UV purity at 254 nm=99%.

$^1$H NMR (300 MHz, DMSO-d$_6$) δ 10.53 (s, 1H), 6.09 (s, 1H), 5.04 (s, 1H), 4.37 (d, 1H), 4.30-4.26 (m, 1H), 3.77-3.67 (m, 4H), 3.65-3.55 (m, 1H), 3.15-3.03 (m, 1H), 2.80-2.65 (m, 2H), 2.25-2.12 (m, 1H), 2.05-1.99 (m, 1H), 1.79 (s, 3H), 1.74-1.20 (m, 8H), 0.76-0.66 (m, 6H).

Preparation of Compound No. 19 Starting from the Isolated Compound (a) (2S,3R,5R,6E,10R,13R,14S,17S)-6-methoxyimino-10,13-dimethyl-17-[(1R,2R)-1,2,5-trihydroxy-1,5-dimethylhexyl]-2,3,4,5,9,11,12,15,16,17-decahydro-1H-cyclopenta[a]phenanthrene-2,3,14-triol Step 2b: Preparation of Compounds (e): [1-[(2S,3R,5R,6E,10R,13R,14S,17S)-2,3,14-trihydroxy-6-methoxyimino-10,13-dimethyl-2,3,4,5,9,11,12,15,16,17-decahydro-1H-cyclopenta[a]phenanthren-17-yl]ethanone] and (f): [1-[(2S,3R,5R,6Z,10R,13R,14S,17S)-2,3,14-trihydroxy-6-methoxyimino-10,13-dimethyl-2,3,4,5,9,11,12,15,16,17-decahydro-1H-cyclopenta[a]phenanthren-17-yl]ethanone]

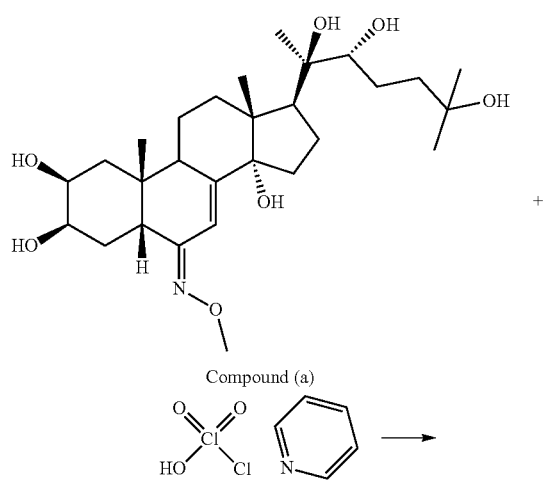

Compound (a)

Compound (f)

According to the same procedure as that described in step 2 of scheme A, 891 mg of beige powder (yield: 36%) of compound (e) [1-[(2S,3R,5R,6E,10R,13R,14S,17S)-2,3,14-trihydroxy-6-methoxyimino-10,13-dimethyl-2,3,4,5,9,11,12,15,16,17-decahydro-1H-cyclopenta[a]phenanthren-17-yl]ethanone] were isolated and also 23 mg (yield: 0.9%) of compound (f): [1-[(2S,3R,5R,6Z,10R,13R,14S,17S)-2,3,14-trihydroxy-6-methoxyimino-10,13-dimethyl-2,3,4,5,9,11,12,15,16,17-decahydro-1H-cyclopenta[a]phenanthren-17-yl]ethanone] were isolated from 3.5 g of the isolated compound (a) [2S,3R,5R,6E,10R,13R,14S,17S)-6-methoxyimino-10,13-dimethyl-17-[(1R,2R)-1,2,5-trihydroxy-1,5-dimethylhexyl]-2,3,4,5,9,11,12,15,16,17-decahydro-1H-cyclopenta[a]phenanthrene-2,3,14-triol].

Compound (e):

LC-MS: m/z=392.2 (MH$^+$) UV purity at 254 nm=99%.

$^1$H NMR (300 MHz, DMSO-d$_6$) 67 6.28 (s, 1H(C7)), 4.74 (s, 1H), 4.42-4.36 (m, 1H), 4.32-4.28 (m, 1H), 3.76-3.70 (m, 4H), 3.68-3.52 (m, 1H), 3.20-3.12 (m, 1H), 2.90-2.76 (m, 1H), 2.30-2.00 (m, 5H), 1.90-1.50 (m, 8H), 1.49-1.24 (m, 3H), 0.72 (s, 3H), 0.45 (s, 3H).

Compound (f):

LC-MS: m/z=392.2 (MH$^+$) UV purity at 254 nm=99%.

$^1$H NMR (300 MHz, DMSO-d$_6$) δ 5.71 (s, 1H(C7)), 4.45 (s, 1H), 4.45-4.41 (m, 1H), 4.26-4.23 (m, 1H), 3.76-3.70 (m, 4H), 3.65-3.55 (m, 1H), 3.18-3.09 (m, 1H), 2.90-2.80 (m, 1H), 2.22-2.00 (m, 5H), 1.88-1.22 (m, 11H), 0.73 (s, 3H), 0.47 (s, 3H).

Step 3b: Preparation of Compound No. 19: [(2S,3R,5R,6E,10R,13R,14S,17S)-17-(N-(2-methoxy-ethoxy)-C-methylcarbonimidoyl)-6-methoxyimino-10,13-dimethyl-2,3,4,5,9,11,12,15,16,17-decahydro-1H-cyclopenta[a]phenanthrene-2,3,14-triol]

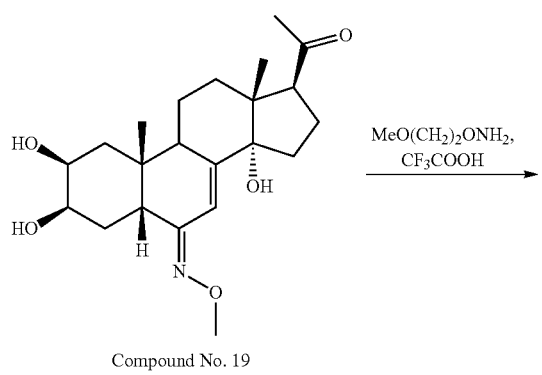

Compound No. 19

Compound (e)

According to the same procedure as that described in step 3 of scheme A, 46 mg of white powder (yield: 48%) of compound No. 19 [(2S,3R,5R,6E,10R,13R,14S,17S)-17-(N-(2-methoxyethoxy)-C-methylcarbonimidoyl)-6-methoxyimino-10,13-dimethyl-2,3,4,5,9,11,12,15,16,17-decahydro-1H-cyclopenta[a]phenanthrene-2,3,14-triol] were prepared from 233 mg of compound (e).

Compound No. 19:

LC-MS: m/z=465.2 (MH+) UV purity at 254 nm=99%.

$^1$H NMR (300 MHz, DMSO-d$_6$) δ 6.28 (s, 1H(C7)), 4.66 (s, 1H), 4.44-4.38 (m, 1H), 4.34-4.28 (m, 1H), 4.10-4.01 (m, 2H), 3.75-3.70 (m, 4H), 3.65-3.45 (m, 3H), 3.24 (s, 3H), 2.98-2.76 (m, 2H), 2.30-1.90 (m, 4H), 1.80-1.24 (m, 12H), 0.73 (s, 3H), 0.49 (s, 3H).

Compound No. 21 was prepared according to the same scheme.

Example 3

Scheme C

Preparation of Compound No. 23: (2S,3R,5R,10R,13R,14S,17S)-17-(N-ethoxy-C-methyl-carbonimidoyl)-2,3,14-trihydroxy-10,13-dimethyl-2,3,4,5,9,11,12,15,16,17-decahydro-1H-cyclopenta[a]phenanthren-6-one

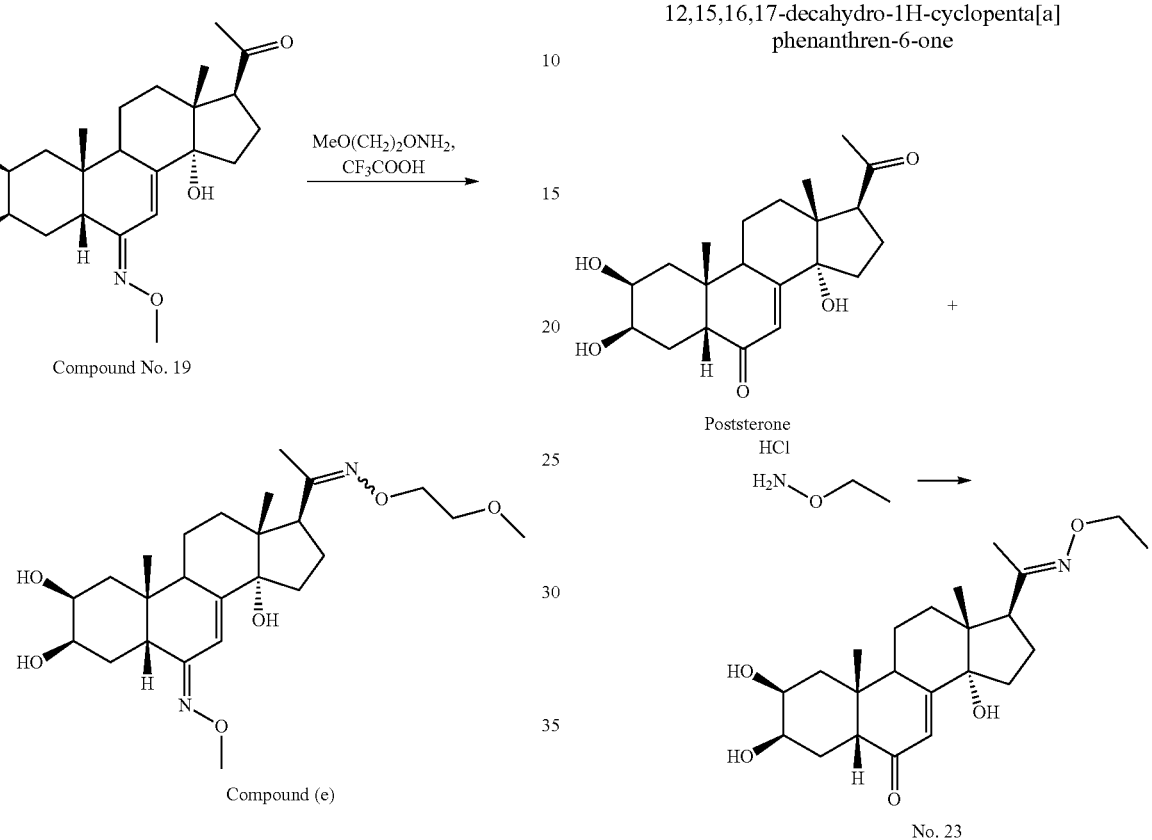

Poststerone HCl

No. 23

According to the same procedure as that described in step 3 of scheme A, 64 mg of white powder (yield: 22%) of (2S,3R,5R,10R,13R,14S,17S)-17-(N-ethoxy-C-methyl-carbonimidoyl)-2,3,14-trihydroxy-10,13-dimethyl-2,3,4,5,9,11,12,15,16,17-decahydro-1H-cyclopenta[a]phenanthren-6-one were prepared from poststerone (obtained by oxidative cleavage of the chain of 20-hydroxyecdysone according to the same procedure as that described in step 2 of scheme B).

Compound No. 23:

LC-MS: m/z=406.2 (MH+) UV purity at 254 nm=93%.

$^1$H NMR (300 MHz, CD$_3$OD) δ 5.82 (s, 1H(C7)), 4.04 (q, 2H), 3.97-3.92 (m, 1H), 3.89-3.80 (m, 1H), 3.22-3.10 (m, 1H), 3.04 (t, 1H), 2.43-1.55 (m, 15H), 1.45-1.37 (m, 1H), 1.21 (t, 3H), 0.96 (s, 3H), 0.64 (s, 3H).

Compounds Nos. 24 to 36 were prepared according to the same scheme.

| No. | MW g/mol | Appearance | Purity[1] (%) | MS m/z MH+ | $^1$H NMR (300 MHz, DMSO-d$_6$) δ |
|---|---|---|---|---|---|
| 21 | 460.6 | white powder | 99 | 461.3 | 10.35 (s, 1H), 6.38 (s, 1H), 5.39-5.27 (m, 1H), 4.58 (s, 1H), 4.49-4.27 (m, 1H), 4.25-4.22 (m, 1H), 3.74 (s, 1H), 3.65-3.55 (m, 1H), 2.96-2.77 (m, 2H), 2.3-1.22 (m, 24H), 0.72 (s, 3H), 0.49 (s, 3H). |

[1]LCMS purity, UV at 254 nm

| No. | MW g/mol | Appearance | Purity[1] (%) | MS m/z MH+ | 1H NMR (300 MHz, DMSO-d6) δ |
|---|---|---|---|---|---|
| 24 | 377.5 | white powder | 99 | 378.1 | (in CD3OD) δ 5.81 (s, 1H(C7)), 3.95 (s, 1H), 3.85-3.80 (m, 1H), 3.25-3.17 (m, 1H), 3.05 (t, 1H), 2.45-1.55 (m, 15H), 1.47-1.39 (m, 1H), 0.96 (s, 3H), 0.63 (s, 3H). |
| 25 | 391.5 | white powder | 95 | 392.2 | (in CD3OD) δ 5.81 (s, 1H(C7)), 3.95 (s, 1H), 3.88-3.75 (m, 4H), 3.23-3.12 (m, 1H), 3.03 (t, 1H), 2.41-1.55 (m, 15H), 1.45-1.39 (m, 1H), 0.96 (s, 3H), 0.63 (s, 3H). |
| 26 | 435.5 | brown powder | 99 | 436.2 | (DMSO + D2O) δ 5.66 (s, 1H(C7)), 4.41 (s, 1H), 3.77 (s, 1H), 3.68-3.58 (m, 1H), 3.03-2.96 (m, 1H), 2.92-2.84 (m, 1H), 2.23-1.21 (m, 16H), 0.8 (s, 3H), 0.47 (s, 3H). |
| 27 | 497.6 | white powder | 92 | 498.2 | 7.30-7.24 (m, 2H), 6.94-6.92 (m, 3H), 5.65 (s, 1H(C7)), 4.95 (s, 1H), 4.50-4.40 (m, 2H), 4.29-4.25 (m, 2H), 4.18-4.12 (m, 2H), 3.78-3.74 (m, 1H), 3.63-3.57 (m, 1H), 3.15-2.80 (m, 2H), 2.25-1.1 (m, 16H), 0.82 (s, 3H), 0.49 (s, 3H). RMN 13C (75 MHz, DMSO-D6)δ 202.8 (C6), 177.8, 164.1, 158.6, 157.8, 129.6, 120.7, 114.5, 82.5, 51.2, 47.2, 45.7, 30.5, 21.1, 16.2, 6.2. |
| 28 | 431.6 | white powder | 99 | 432.2 | 5.87-5.73 (m, 1H), 5.65 (s, 1H(C7)), 5.1-5 (m, 2H), 4.94 (s, 1H), 4.49 (d, 1H), 4.41-4.39 (m, 1H), 4.05-3.95 (m, 2H), 3.77 (s, 1H), 3.66-3.58 (m, 1H), 3.1-2.98 (m, 1H), 2.94 (t, 1H), 2.4-1.4 (m, 17H), 1.32-1.22 (m, 1H), 0.83 (s, 3H), 0.51 (s, 3H). RMN 13C (75 MHz, DMSO-d6)δ 202.8 (C6), 164.2, 156.9, 116.6, 82.5, 71.7, 47.2, 37.7, 33.5, 31.6, 21.1. |
| 29 | 435.6 | white powder | 99 | 436.2 | 5.65 (s, 1H(C7)), 4.94 (s, 1H), 4.50-4.48 (m, 1H), 4.42-4.39 (m, 1H), 4.10-4.02 (m, 2H), 3.8-3.72 (m, 1H), 3.7-3.55 (m, 1H), 3.52-3.48 (m, 2H), 3.24 (s, 3H), 3.08-3 (m, 1H), 2.94 (t, 1H), 2.28-2.03 (m, 3H), 1.92-1.42 (m, 12H), 1.34-1.20 (m, 1H), 0.83 (s, 3H), 0.51 (s, 3H). |
| 30 | 445.6 | beige powder | 90 | 446.2 | 5.65 (s, 1H(C7)), 5.37-5.29 (m, 1H), 4.92 (s, 1H), 4.51-4.35 (m, 3H), 3.81-3.74 (m, 1H), 3.68-3.56 (m, 1H), 3.08-2.85 (m, 2H), 2.25-1.18 (m, 23H), 0.83 (s, 3H), 0.50 (s, 3H). |
| 31 | 490.6 | white powder | 90 | 491.3 | 5.66 (s, 1H(C7)), 4.97 (s, 1H), 4.52-4.3 (m, 4H), 3.95-3.55 (m, 7H), 3.1-2.87 (m, 4H), 2.25-1.18 (m, 19H), 0.83 (s, 3H), 0.52 (s, 3H). |
| 32 | 476.7 | white powder | 99 | 477.3 | 5.65 (s, 1H(C7)), 4.98 (s, 1H), 4.52 (d, 1H), 4.44-4.40 (m, 1H), 4.39-4 (m, 2H), 3.77 (s, 1H), 3.70-3.54 (m, 1H), 3.1-2.85 (m, 6H), 2.28-2.02 (m, 4H), 1.9-0.92 (m, 21H), 0.83 (s, 3H), 0.52 (s, 3H). |
| 33 | 479.6 | orange powder | 99 | 480.2 | 7.34-7.24 (m, 2H), 6.97-6.89 (m, 3H), 6.14-6.08 (m, 1H), 5.57 (s, 1H), 4.48-4.15 (m, 6H), 3.66 (s, 1H), 3.47-3.37 (m, 1H), 2.35-1.95 (m, 4H), 1.92-1.65 (m, 8H), 1.62-1.43 (m, 4H), 0.97-0.94 (m, 6H). |
| 34 | 508.6 | white powder | 96 | 509.2 | 8.57 (s, 1H), 6.35 (s, 1H(C7)), 4.72 (s, 1H), 4.47 (s, 4H), 3.74 (m, 3H), 2.28-1.25 (m, 19H), 0.75-0.65 (m, 3H), 0.5 (s, 3H). |
| 35 | 448.6 | white powder | 97 | 449.2 | 5.66 (s, 1H(C7)), 4.97 (s, 1H), 4.55-4.25 (m, 4H), 3.77 (s, 1H), 3.68-3.56 (m, 1H), 3.12-2.9 (m, 3H), 2.77 (s, 6H), 2.28-2.05 (m, 4H), 1.9-1.4 (m, 12H), 1.34-1.21 (m, 1H), 0.84 (s, 3H), 0.54 (s, 3H). |
| 36 | 474.6 | white powder | 96 | 475.2 | (in D2O) δ 5.95 (s, 1H(C7)), 4.38-4.31 (m, 2H), 4.06-3.91 (m, 2H), 3.74-3.60 (m, 2H), 3.55-3.48 (m, 2H), 3.20-3.05 (m, 2H), 3.03-2.93 (m, 1H), 2.35-1.55 (m, 20H), 1.41-1.28 (m, 1H), 0.95 (s, 3H), 0.62 (s, 3H). |

[1] LCMS purity, UV at 254 nm

Example 4

Scheme D

Preparation of Compound No. 37: N-(2,2-difluoroethyl)-N-[1-[(2S,3R,5R,6E,10R,13R,14S,17S)-2,3,14-trihydroxy-6-methoxyimino-10,13-dimethyl-2,3,4,5,9,11,12,15,16,17-decahydro-1H-cyclopenta[a]phenanthren-17-yl]ethyl]furan-2-carboxamide

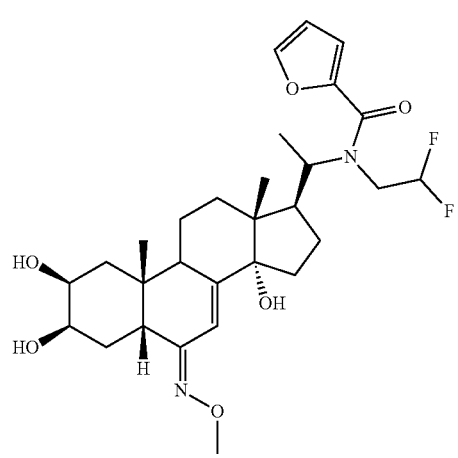

No. 37

Step 1: Preparation of Compound No. 39: [(2S,3R,5R,6E,10R,13R,14S,17S)-17-[1-(2,2-difluoroethylamino)ethyl]-6-methoxyimino-10,13-dimethyl-2,3,4,5,9,11,12,15,16,17-decahydro-1H-cyclopenta[a]phenanthrene-2,3,14-triol]

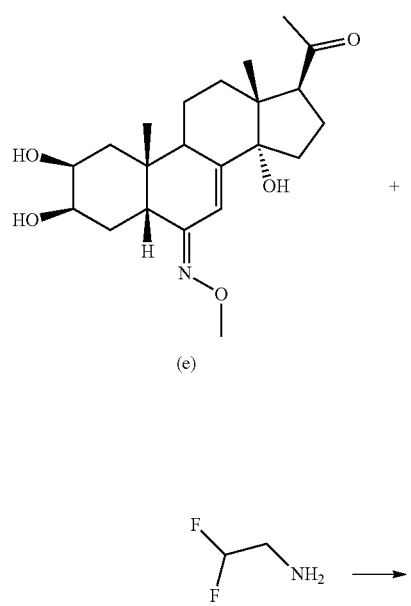

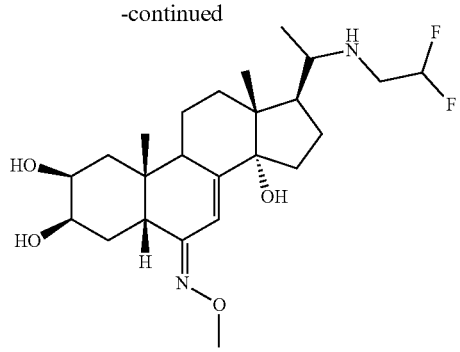

No. 39

180 mg (0.46 mmol) of compound (e) [1-[(2S,3R,5R,6E,10R,13R,14S,17S)-2,3,14-trihydroxy-6-methoxyimino-10,13-dimethyl-2,3,4,5,9,11,12,15,16,17-decahydro-1H-cyclopenta[a]phenanthren-17-yl]ethanone] obtained in step 2b of method B are dissolved in 5 ml of methanol and 0.21 ml (2.76 mmol) of 2,2-difluoroethanamine is added to the reaction medium. The pH of the solution is adjusted to 6 using the sufficient amount of concentrated acetic acid. 31.8 mg (0.506 mmol) of sodium cyanoborohydride are then added portionwise and the suspension obtained is refluxed for 20 h. The solvent is evaporated off and the residue obtained is taken up in 20 ml of water and the pH is adjusted to 8 using a saturated sodium bicarbonate solution. This aqueous phase is extracted with two times 15 ml of butanol and the butanol phase is dried over solvate, filtered and evaporated to give a yellow solid, which, taken up in 30 ml of isopropyl ether and filtered, gives, after drying, 134 mg (yield: 62%) of compound No. 39 (2S,3R,5R,6E,10R,13R,14S,17S)-17-[1-(2,2-difluoroethylamino)ethyl]-6-methoxyimino-10,13-dimethyl-2,3,4,5,9,11,12,15,16,17-decahydro-1H-cyclopenta[a]phenanthrene-2,3,14-triol in the form of a yellow powder.

Compound No. 39:

LC-MS: m/z=457.4 (MH$^+$) UV purity at 254 nm=97%.

$^1$H NMR (300 MHz, DMSO-d$_6$) δ 6.30-6.23 (m, 1H), 5.95-5.70 (m, 1H), 4.43-4.25 (m, 3H), 3.72 (s, 3H), 3.65-3.55 (m, 1H), 3.42-3.32 (m, 1H), 2.88-2.76 (m, 2H), 2.29-2.23 (m, 1H), 1.99-1.15 (m, 16H), 1.05-0.82 (m, 3H), 0.73 (s, 3H), 0.61-0.53 (m, 3H).

Step 2: Preparation of Compound No. 37: N-(2,2-difluoroethyl)-N-[1-[(2S,3R,5R,6E,10R,13R,14S,17S)-2,3,14-trihydroxy-6-methoxyimino-10,13-dimethyl-2,3,4,5,9,11,12,15,16,17-decahydro-1H-cyclopenta[a]phenanthren-17-yl]ethyl]furan-2-carboxamide

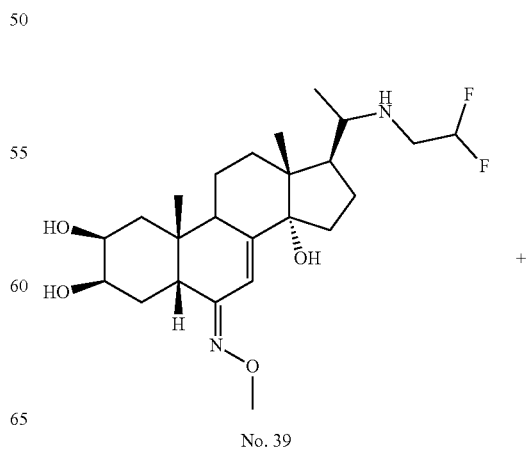

No. 39

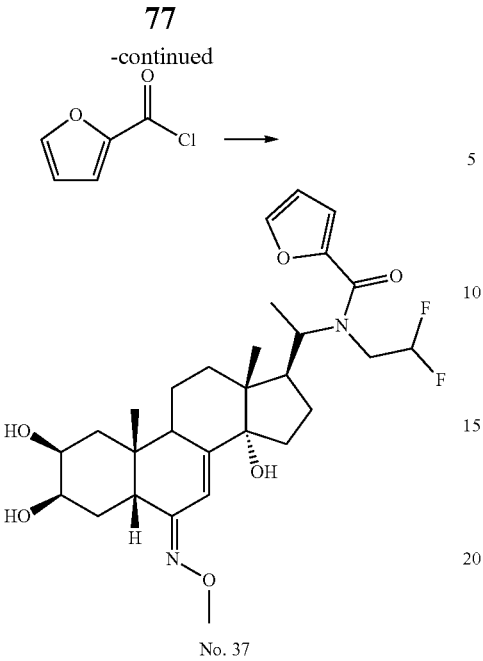

134 mg (0.285 mmol) of compound No. 39 [(2S,3R,5R,6E,10R,13R,14S,17S)-17-[1-(2,2-difluoroethylamino)ethyl]-6-methoxyimino-10,13-dimethyl-2,3,4,5,9,11,12,15,16,17-decahydro-1H-cyclopenta[a]phenanthrene-2,3,14-triol] are dissolved in 2 ml of THF and 52 mg (0.854 mmol) of sodium bicarbonate are added to the reaction medium under an argon atmosphere. 30 μL (0.299 mmol) of furoyl chloride are added and the reaction medium is stirred for 20 h at 20° C. The solution is then poured onto 5 ml of water and extracted two times with 10 ml of butanol. The butanol phase is evaporated off to give 118 mg of solid purified by flash chromatography on a silica gel cartridge (95/5 dichloromethane/MeOH) to give 100 mg of white powder (yield: 60%) of compound No. 37: N-(2,2-difluoroethyl)-N-[1-[(2S,3R,5R,6E,10R,13R,14S,17S)-2,3,14-trihydroxy-6-methoxyimino-10,13-dimethyl-2,3,4,5,9,11,12,15,16,17-decahydro-1H-cyclopenta[a]phenanthren-17-yl]ethyl]furane-2-carboxamide.

Compound No. 37:

LC-MS: m/z=551.3 (MH$^+$) UV purity at 254 nm=93%.

$^1$H NMR (300 MHz, DMSO-d$_6$) δ 7.87 (s, 1H), 7.03 (s, 1H), 6.64 (s, 1H), 6.25 (s, 1H), 4.58 (d, 1H), 4.43-4.27 (m, 3H), 3.95-3.83 (m, 1H), 3.75-3.65 (m, 4H), 3.63-3.49 (m, 2H), 2.85-2.68 (m, 1H), 2.31-2.18 (m, 1H), 2.01-1 (m, 17H), 0.73-0.15 (m, 6H).

Compounds Nos. 38 and 40 were prepared according to the same scheme.

Example 5

Scheme E

Preparation of Compound No. 41: 2-methoxy-N-(2-methoxyethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]acetamide

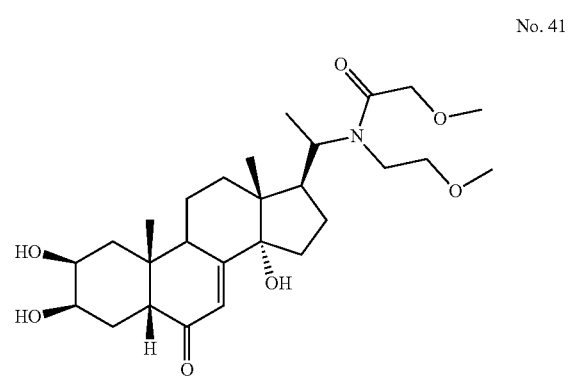 [SMILES: COCCN(C(=O)COC)C(C)[C@H]1CC[C@@]2(O)C3=CC(=O)[C@@H]4C[C@@H](O)[C@@H](O)C[C@]4(C)C3CC[C@]12C]

No. 41

Step 1: Preparation of Compound No. 42: (2S,3R,5R,10R,13R,14S,17S)-2,3,14-trihydroxy-17-[1-(2-methoxyethylamino)ethyl]-10,13-dimethyl-2,3,4,5,9,11,12,15,16,17-decahydro-1H-cyclopenta[a]phenanthren-6-one

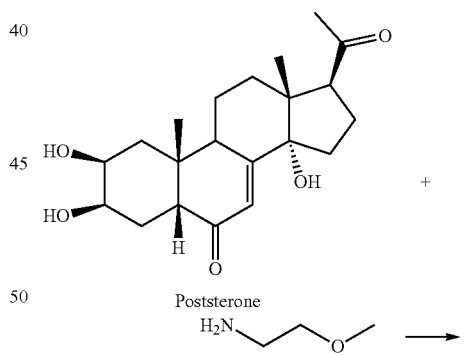

Poststerone

| No. | MW g/mol | Appearance | Purity[1] (%) | MS m/z MH$^+$ | $^1$H NMR (300 MHz, DMSO-d$_6$) δ |
|---|---|---|---|---|---|
| 38 | 550.7 | white powder | 93 | 551.5 | 6.27 (s, 1H(C7)), 4.55-4.22 (m, 4H), 3.78-3.67 (m, 4H), 3.62-3.54 (m, 1H), 3.32-3.22 (m, 6H), 2.95-2.70 (m, 2H), 2.30-2.19 (m, 1H), 2-0.9 (m, 25H), 0.79-0.40 (m, 6H). |
| 40 | 480.6 | beige powder | 99 | 481.4 | 6.35-6.24 (m, 1H), 4.48-4.25 (m, 4H), 3.71 (s, 3H), 3.65-3.55 (m, 1H), 3.40-3.20 (m, 7H), 2.88-2.76 (m, 1H), 2.75-2.66 (m, 1H), 2.29-2.22 (m, 1H), 2-1.15 (m, 15H), 1.05-0.76 (m, 4H), 0.73 (s, 3H), 0.61-0.54 (m, 3H). |

[1]LCMS purity, UV at 254 nm

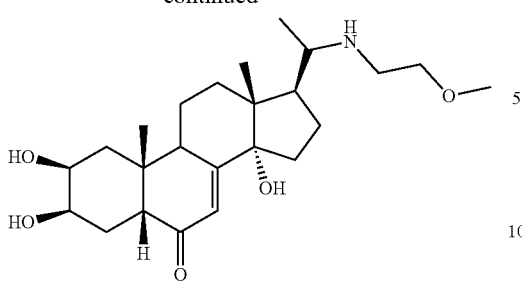

No. 42

5 g (13.8 mmol) of poststerone (obtained by oxidative cleavage of the chain of 20-hydroxyecdysone according to the same procedure as that described in step 2 of scheme B) are dissolved in 250 ml of methanol and 7.2 ml (83 mmol) of 2-methoxyethylamine are added dropwise. The pH of the solution is then brought to pH 6 by adding concentrated acetic acid, and 250 ml of THF are added. 0.954 g of sodium cyanoborohydrure are added portionwise and the reaction medium is brought to reflux for 20 h. The solvents are evaporated off and the crude product obtained is taken up in 100 ml of water and the pH is adjusted to 8 by adding a saturated sodium bicarbonate solution. The medium is extracted three times with 80 ml of butanol and the butanol phase is evaporated off to give a brown foam which, taken up with 5 ml of ethyl acetate, gives, after filtration and drying, 3.32 g (yield: 57%) of compound No. 42: (2S,3R, 5R,10R,13R,14S,17S)-2,3,14-trihydroxy-17-[1-(2-methoxyethylamino)ethyl]-10,13-dimethyl-2,3,4,5,9,11,12, 15,16,17-decahydro-1H-cyclopenta[a]phenanthren-6-one in the form of a gray powder.

Compound No. 42:

LC-MS: m/z=422.2 (MH$^+$) UV purity at 254 nm=95%.

$^1$H NMR (300 MHz, DMSO-d$_6$) δ 5.70-5.60 (m, 1H(C7)), 4.80-4.62 (m, 1H), 4.55-4.47 (m, 1H), 4.43-4.35 (m, 1H), 3.78-3.70 (m, 2H), 3.68-3.50 (m, 3H), 3.30-3.18 (m, 5H), 3.10-2.91 (m, 1H), 2.30-0.9 (m, 18H), 0.82 (s, 3H), 0.59 (s, 3H).

$^{13}$C NMR (75 MHz, DMSO-d$_6$) δ 202.9 (C$_6$), 120.5, 82.9, 66.7, 58.1, 46.2, 37.8, 30.5, 23.9, 6.2.

Step 2: Preparation of Compound No. 41: 2-methoxy-N-(2-methoxyethyl)-N-[1-[(2S,3R,5R, 10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]acetamide

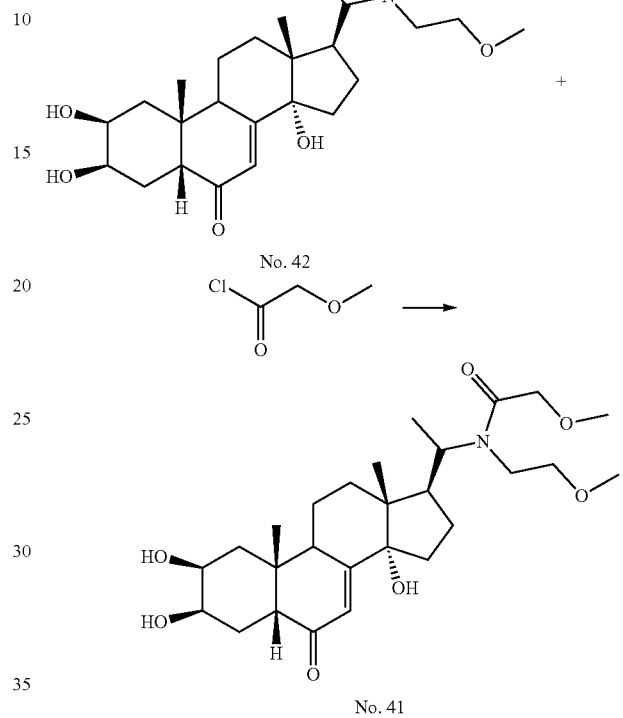

According to the same procedure as step 2 of example 5, 89 mg (yield: 58%) of compound No. 41 [2-methoxy-N-(2-methoxyethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]acetamide] were obtained in the form of an orange powder from compound No. 42.

Compound No. 41:

LC-MS: m/z=494.4 (MH$^+$) UV purity at 254 nm=94%.

$^1$H NMR (300 MHz, DMSO-d$_6$) δ 5.63 (s, 1H(C7)), 4.88-4.7 (m, 1H), 4.5-4.35 (m, 2H), 4.2-3.9 (m, 2H), 3.76 (s, 1H), 3.68-3.52 (m, 1H), 3.5-3.3 (m, 4H), 3.28-3.18 (m, 6H), 3.08-2.9 (m, 1H), 2.3-0.95 (m, 18H), 0.88-0.75 (m, 3H), 0.7-0.42 (m, 3H).

Compounds Nos. 43 to 75 were prepared according to the same scheme:

| No. | MW g/mol | Appearance | Purity[1] (%) | MS m/z MH$^+$ | $^1$H NMR (300 MHz, DMSO-d$_6$) δ |
|---|---|---|---|---|---|
| 43 | 454.6 | white powder | 91 | 455.2 | 8.54-8.38 (m, 2H), 7.75-7.68 (m, 1H), 7.35-7.28 (m, 1H), 5.60 (s, 1H(C7)), 4.63 (s, 1H), 4.42 (d, 1H), 4.37-4.34 (m, 1H), 3.88-3.48 (m, 5H), 3.10-2.85 (m, 1H), 2.25-1.05 (m, 15H), 1.03 (d, 3H), 0.83 (s, 3H), 0.52 (s, 3H). |
| 44 | 476.7 | white powder | 91 | 477.3 | 5.67-5.60 (m, 1H(C7)), 4.98-4.40 (m, 3H), 3.76 (s, 1H), 3.68-3.45 (m, 5H), 3.10-2.78 (m, 2H), 2.45-0.95 (m, 26H), 0.83 (s, 3H), 0.64-0.58 (m, 3H). |
| 45 | 403.6 | white powder | 85 | 404.2 | 5.73-5.60 (m, 1H(C7)), 4.80-4.62 (m, 1H), 4.56-4.50 (m, 1H), 4.46-4.38 (m, 1H), 3.77 (s, 1H), 3.68-3.53 (m, 2H), 3.53-3.45 (m, 1H), 3.10-2.85 (m, 1H), 2.30-0.98 (m, 22H), 0.84 (s, 3H), 0.65-0.5 (m, 3H). |

-continued

| No. | MW g/mol | Appearance | Purity[1] (%) | MS m/z MH+ | $^1$H NMR (300 MHz, DMSO-d6) δ |
|---|---|---|---|---|---|
| 46 | 447.6 | yellow oil | 92 | 448.2 | 5.69-5.61 (m, 1H(C7)), 4.92-4.75 (m, 1H), 4.48-4.33 (m, 2H), 4.18-3.55 (m, 4H), 3.1-2.7 (m, 3H), 2.3-1 (m, 24H), 0.85 (s, 3H), 0.65-0.55 (m, 3H). 13C NMR (75 MHz, DMSO-d6)δ 202.8 (C6), 163.9, 120.5, 82.8, 67.5, 66.7, 50.1, 46.2, 37.7, 36.6, 33.3, 28.9, 25.2, 23.9, 20, 15.2. |
| 47 | 515.7 | white powder | 93 | 516.1 | 5.68-5.60 (m, 1H(C7)), 4.87-4.65 (m, 1H), 4.48-4.35 (m, 2H), 4.08-3.88 (m, 1H), 3.81-3.50 (m, 4H), 3.35-3.25 (m, 2H), 3.08-2.9 (m, 1H), 2.3-0.95 (m, 23H), 0.9-0.4 (m, 10H). |
| 48 | 501.7 | white powder | 97 | 502.4 | 6.85-6.65 (m, 1H), 6.20-5.9 (m, 1H), 5.70-5.50 (m, 2H), 4.85-4.70 (m, 1H), 4.48-4.30 (m, 2H), 4.2-3.8 (m, 1H), 3.77-3.70 (m, 2H), 3.68-3.40 (m, 3H), 3.10-2.85 (m, 1H), 2.27-1 (m, 23H), 0.85-0.75 (m, 3H), 0.70-0.46 (m, 3H). |
| 49 | 515.6 | white powder | 99 | 516.3 | 7.82 (s, 1H), 6.93 (s, 1H), 6.60 (s, 1H), 5.65-5.55 (m, 1H), 4.84 (s, 1H), 4.48-4.35 (m, 2H), 4.30-4.20 (m, 1H), 3.77-3.33 (m, 3H), 3.32-3.12 (m, 5H), 3.10-2.85 (m, 1H), 2.25-1 (m, 18H), 0.84-0.76 (m, 3H), 0.74-0.17 (m, 3H). |
| 50 | 503.7 | mauve powder | 99 | 504.3 | 5.62 (s, 1H(C7)), 4.88-4.65 (m, 1H), 4.47-4.33 (m, 2H), 4.08-3.85 (m, 1H), 3.8-3.5 (m, 4H), 3.08-2.9 (m, 2H), 2.3-0.9 (m, 28H), 0.88-0.72 (m, 3H), 0.69-0.4 (m, 3H). |
| 51 | 519.7 | white powder | 94 | 520.4 | 5.63 (s, 1H(C7)), 4.88-4.7 (m, 1H), 4.45-4.35 (m, 2H), 3.75 (s, 1H), 3.68-3.52 (m, 1H), 3.52-3.35 (m, 2H), 3.27-3.21 (m, 5H), 3.08-2.9 (m, 1H), 2.26-0.86 (m, 23H), 0.87-0.72 (m, 9H), 0.70-0.47 (m, 3H). |
| 52 | 503.7 | orange powder | 99 | 504.4 | 5.91-5.75 (m, 1H), 5.68-5.60 (m, 1H(C7)), 5.07-4.89 (m, 2H), 4.83-4.65 (m, 1H), 4.45-4.28 (m, 2H), 3.76 (s, 1H), 3.68-3.52 (m, 1H), 3.46-3.35 (m, 2H), 3.30-3.15 (m, 5H), 3.08-2.09 (m, 1H), 2.47-0.92 (m, 22H), 0.90-0.77 (m, 3H), 0.7-0.45 (m, 3H). |
| 53 | 531.7 | white powder | 99 | 532.4 | 7.76-7.70 (m, 1H), 7.39-7.32 (m, 1H), 7.12-7.08 (m, 1H), 5.59 (s, 1H(C7)), 4.81 (s, 1H), 4.43-4.22 (m, 2H), 3.78-3.53 (m, 2H), 3.52-3.32 (m, 2H), 3.28-3.08 (m, 5H), 3.05-2.85 (m, 1H), 2.25-1.15 (m, 18H), 0.83-0.76 (m, 3H), 0.70-0.15 (m, 3H). |
| 54 | 475.6 | white powder | 99 | 476.3 | 5.63 (s, 1H(C7)), 4.78-4.68 (m, 1H), 4.45-4.32 (m, 2H), 4.28-4.08 (m, 2H), 3.8-3.7 (m, 1H), 3.68-3.54 (m, 1H), 3.28-3.18 (m, 5H), 3.05-2.85 (m, 1H), 2.25-1.09 (m, 17H), 0.88-0.7 (m, 7H), 0.68-0.52 (m, 3H). |
| 55 | 459.6 | white powder | 99 | 460.3 | 5.63 (s, 1H(C7)), 4.78-4.52 (m, 1H), 4.48-4.32 (m, 2H), 3.76 (s, 1H), 3.68-3.54 (m, 1H), 3.05-2.85 (m, 1H), 2.48-1.08 (m, 21H), 1.02-0.92 (m, 3H), 0.90-0.69 (m, 7H), 0.68-0.52 (m, 3H). |
| 56 | 532.7 | white powder | 99 | 533.3 | 7.89 (d, 2H), 7.60 (d, 2H), 5.66 (s, 1H(C7)), 4.81 (s, 1H), 4.49-4.32 (m, 2H), 3.76 (s, 1H), 3.68-3.54 (m, 1H), 3.05-2.85 (m, 1H), 2.80-2.72 (m, 1H), 2.27-1.18 (m, 18H), 0.85 (s, 3H), 0.73-0.22 (m, 7H). |
| 57 | 534.7 | white powder | 99 | 535.3 | 5.62 (s, 1H(C7)), 4.78 (s, 1H), 4.46 (d, 1H), 4.39-4.35 (m, 1H), 3.75 (s, 1H), 3.68-3.4 (m, 5H), 3.28-3.13 (m, 5H), 3.10-2.82 (m, 7H), 2.4-1.1 (m, 18H), 0.88-0.75 (m, 3H), 0.65-0.51 (m, 3H). |
| 58 | 508.7 | pink powder | 99 | 509.4 | 8.68-8.55 (m, 2H), 7.85-7.77 (m, 1H), 7.5-7.35 (m, 1H), 5.66 (s, 1H(C7)), 4.82 (s, 1H), 4.48-4.30 (m, 2H), 3.76 (s, 1H), 3.68-3.54 (m, 1H), 3.12-2.78 (m, 2H), 2.25-1.15 (m, 18H), 0.88-0.18 (m, 10H). |
| 59 | 537.7 | white powder | 92 | 538.8 | 7.42 (t, 2H), 6.98-6.85 (m, 2H), 5.69-5.62 (m, 1H(C7)), 4.85-4.79 (m, 1H), 4.49-4.35 (m, 2H), 3.78-3.73 (m, 4H), 3.67-3.51 (m, 1H), 3.10-2.87 (m, 2H), 2.27-1.20 (m, 18H), 0.87-0.83 (m, 3H), 0.74-0.18 (m, 7H). |

-continued

| No. | MW g/mol | Appearance | Purity[1] (%) | MS m/z MH+ | 1H NMR (300 MHz, DMSO-d$_6$) δ |
|---|---|---|---|---|---|
| 60 | 545.7 | white powder | 99 | 546.2 | 7.83 (s, 1H), 6.94 (s, 1H), 6.61 (s, 1H), 5.67-5.57 (m, 1H(C7)), 4.84 (s, 1H), 4.63-4.17 (m, 4H), 3.75 (s, 1H), 3.67-3.51 (m, 2H), 3.29-3.24 (m, 6H), 3.10-2.87 (m, 1H), 2.25-1.03 (m, 18H), 0.85-0.74 (m, 3H), 0.70-0.10 (m, 3H). |
| 61 | 505.7 | white powder | 99 | 506.2 | 6.85-6.65 (m, 1H), 6.20-6.00 (m, 1H), 5.70-5.62 (m, 1H), 4.87-4.70 (m, 1H), 4.48-4.36 (m, 2H), 3.75 (s, 1H), 3.65-3.42 (m, 2H), 3.29-3.24 (m, 6H), 3.10-2.87 (m, 2H), 2.27-0.98 (m, 19H), 0.86-0.78 (m, 3H), 0.70-0.46 (m, 3H). |
| 62 | 519.7 | white powder | 99 | 520.3 | 5.63 (s, 1H(C7)), 4.9-4.65 (m, 1H), 4.48-4.36 (m, 2H), 4.25-3.85 (m, 3H), 3.82-3.70 (m, 2H), 3.68-3.56 (m, 2H), 3.29-3.23 (m, 3H), 3.08-2.93 (m, 2H), 2.28-1.02 (m, 23H), 0.86-0.79 (m, 3H), 0.66-0.47 (m, 3H). |
| 63 | 541.7 | white powder | 97 | 542.2 | 7.84-7.75 (m, 1H), 6.94-6.86 (m, 1H), 6.62-6.57 (m, 1H), 5.64-5.53 (m, 1H(C7)), 4.84 (s, 1H), 4.48-4.36 (m, 2H), 4.34-3.80 (m, 2H), 3.78-3.50 (m, 5H), 3.08-2.93 (m, 2H), 2.24-1.05 (m, 21H), 0.85-0.74 (m, 3H), 0.73-0.16 (m, 3H). |
| 64 | 561.7 | white powder | 97 | no mass | 7.77-7.71 (m, 1H), 7.41-7.30 (m, 1H), 7.13-7.09 (m, 1H), 5.70-5.56 (m, 1H(C7)), 4.84 (s, 1H), 4.62-4.17 (m, 4H), 3.74-3.51 (m, 3H), 3.32-3.26 (m, 6H), 3.08-2.93 (m, 2H), 2.24-1.15 (m, 17H), 0.85-0.70 (m, 3H), 0.68-0.17 (m, 3H). |
| 65 | 519.7 | white powder | 97 | 520.2 | 5.68-5.60 (m, 1H(C7)), 4.86-4.70 (m, 1H), 4.56-4.34 (m, 3H), 3.75 (s, 1H), 3.67-3.53 (m, 2H), 3.30-3.23 (m, 6H), 3.10-2.9 (m, 2H), 2.23-0.93 (m, 19H), 0.87-0.77 (m, 3H), 0.75-0.40 (m, 7H). |
| 66 | 521.7 | white powder | 94 | 522.3 | 5.63 (s, 1H(C7)), 4.86-4.70 (m, 1H), 4.55-4.34 (m, 3H), 3.76 (s, 1H), 3.68-3.53 (m, 1H), 3.35-3.20 (m, 6H), 3.10-2.87 (m, 2H), 2.29-0.9 (m, 26H), 0.88-0.72 (m, 3H), 0.69-0.41 (m, 3H). |
| 67 | 521.6 | white powder | 99 | 522.1 | 7.87 (s, 1H), 7.07-7.01 (m, 1H), 6.67-6.61 (m, 1H), 5.63-5.54 (m, 1H(C7)), 4.88-4.84 (m, 1H), 4.45-4.32 (m, 3H), 4.01-3.35 (m, 3H), 3.10-2.85 (m, 1H), 2.25-1.05 (m, 19H), 0.80-0.76 (m, 3H), 0.70-0.17 (m, 3H). |
| 68 | 495.6 | white powder | 99 | 496.2 | 6.43-5.87 (m, 1H), 5.67-5.63 (m, 1H(C7)), 4.88-4.70 (m, 1H), 4.47-4.25 (m, 3H), 3.80-3.52 (m, 3H), 3.10-2.85 (m, 1H), 2.30-0.95 (m, 19H), 0.90-0.46 (m, 10H). |
| 69 | 481.6 | white powder | 99 | 482.1 | 6.95-6.68 (m, 1H), 6.38-5.90 (m, 2H), 5.78-5.61 (m, 2H), 4.88-4.70 (m, 1H), 4.47-4.34 (m, 2H), 4.15-3.85 (m, 1H), 3.83-3.74 (m, 2H), 3.68-3.5 (m, 1H), 3.10-2.85 (m, 1H), 2.30-0.98 (m, 18H), 0.81-0.77 (m, 3H), 0.65 (s, 1H), 0.50(s, 2H). |
| 70 | 427.5 | yellow powder | 99 | 428.1 | 6.13-5.59 (m, 1H), 5.61 (s, 1H(C7)), 4.63 (s, 1H), 4.44 (s, 1H), 4.35 (s, 1H), 3.76 (s, 1H), 3.68-3.53 (m, 1H), 3.10-2.85 (m, 1H), 2.30-2.15 (m, 2H), 2-1.1 (m, 16H), 0.97 (s, 3H), 0.84 (s, 3H), 0.61 (s, 3H). |
| 71 | 527.6 | yellow powder | 99 | 528.2 | 6.13-5.71 (m, 1H), 5.67 (s, 1H(C7)), 5.03-4.99 (m, 1H), 4.77 (s, 1H), 4.70-4.57 (m, 1H), 3.99 (s, 1H), 3.12-3 (m, 1H), 2.92-2.70 (m, 2H), 2.30-2.24 (m, 1H), 2.10-1.18 (m, 24H), 1.08-0.96 (m, 3H), 0.87 (s, 3H), 0.57 (s, 3H). |
| 72 | 526.7 | yellow powder | 99 | 527.2 | 8.50-8.37 (m, 2H), 7.64-7.60 (m, 1H), 7.45-7.28 (m, 1H), 5.67-5.62 (m, 1H(C7)), 4.95-4 (m, 6H), 3.83-3.50 (m, 3H), 3.35-3.24 (m, 3H), 3.12-2.85 (m, 1H), 2.25-0.80 (m, 18H), 0.84 (s, 3H), 0.70 (m, 3H). |
| 73 | 548.7 | yellow powder | 99 | 549.2 | 8.55-8.32 (m, 2H), 7.88-7.80 (m, 1H), 7.75-7.60 (m, 1H), 7.34-7.25 (m, 1H), 7.05-6.80 (m, 1H), 6.66-6.40 (m, 1H), 5.62 (s, 1H(C7)), 4.90-4.70 (m, 2H), 4.49-4.27 (m, 3H), 3.76 (s, 1H), 3.69-3.53 (m, 1H), 3.12-2.85 (m, 1H), 2.27-0.95 (m, 18H), 0.84-0.73 (m, 3H), 0.65-0.19 (m, 3H). |
| 74 | 522.7 | yellow powder | 96 | 523.2 | 8.60-8.30 (m, 2H), 7.73-7.5 (m, 1H), 7.41-7.25 (m, 1H), 5.67-5.62 (m, 1H(C7)), 4.92-4.75 (m, 2H), 4.5-4.3 (m, 2H), 3.76 (s, 1H), 3.69-3.53 (m, 1H), 3.12-2.89 (m, 1H), 2.28-0.96 (m, 20H), 0.97-0.40 (m, 10H). |
| 75 | 491.7 | white powder | 99 | 492.2 | 5.68-5.60 (m, 1H(C7)), 4.84 (s, 1H), 4.82-4.65 (m, 1H), 4.46-4.32 (m, 2H), 3.76 (s, 1H), 3.68-3.52 (m, 2H), 3.48-3.38 (m, 1H), 3.23-3.19 (m, 5H), 3.20-2.71 (m, 3H), 2.29-0.90 (m, 22H), 0.80-0.77 (m, 3H), 0.71-0.45 (m, 3H). |

[1] LCMS purity, UV at 254 nm

Example 6

Scheme F

Preparation of Compound No. 76: (2S,3R,5R,10R,13R,14S,17S)-2,3,14-trihydroxy-17-[1-(2-methoxyethyl(methyl)amino)ethyl]-10,13-dimethyl-2,3,4,5,9,11,12,15,16,17-decahydro-1H-cyclopenta[a]phenanthren-6-one

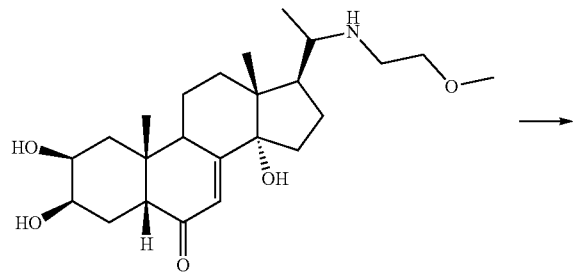

No. 42

155 mg (0.368 mmol) of compound No. 42 [(2S,3R,5R,10R,13R,14S,17S)-2,3,14-trihydroxy-17-[1-(2-methoxyethylamino)ethyl]-10,13-dimethyl-2,3,4,5,9,11,12,15,16,17-decahydro-1H-cyclopenta[a]phenanthren-6-one] prepared according to the technique described in step 1 of example 5 are dissolved in 2.5 ml of DMF and 61.8 mg (0.735 mmol) of sodium bicarbonate are added to the reaction medium, along with 0.034 ml (0.552 mmol) of iodomethane. The suspension obtained is stirred at 20° C. for 20 h. The solution is then poured onto 15 ml of water and extracted three times with 15 ml of butanol. The butanol phase is evaporated off to give 220 mg of powder purified by flash chromatography on a silica gel cartridge (95/5 dichloromethane/MeOH) to give 40 mg of white powder (yield: 25%) of compound No. 76: (2S,3R,5R,10R,13R,14S,17S)-2,3,14-trihydroxy-17-[1-(2-methoxyethyl(methyl)amino)ethyl]-10,13-dimethyl-2,3,4,5,9,11,12,15,16,17-decahydro-1H-cyclopenta[a]phenanthren-6-one in the form of a white powder.

Compound No. 76:

LC-MS: m/z=436.3 (MH$^+$) UV purity at 254 nm=99%.

$^1$H NMR (300 MHz, DMSO-d$_6$) δ 5.61 (s, 1H(C7)), 4.64 (s, 1H), 4.47-4.34 (m, 2H), 3.75 (s, 1H), 3.67-3.50 (m, 1H), 3.25-3.16 (m, 5H), 3.05-2.85 (m, 1H), 2.27-1.15 (m, 20H), 0.90-0.70 (m, 6H), 0.59 (s, 3H).

Compounds Nos. 77 to 80 were prepared according to the same scheme.

| No. | MW g/mol | Appearance | Purity[1] (%) | MS m/z MH$^+$ | $^1$H NMR(300 MHz, DMSO-d$_6$) δ |
|---|---|---|---|---|---|
| 77 | 461.6 | white powder | 86 | 462.3 | 5.68-5.58 (m, 1H(C7)), 4.50-4.30 (m, 2H), 3.85-3.50 (m, 4H), 3.10-2.90 (m, 2H), 2.25-1.10 (m, 25H), 0.90-0.75 (m, 6H), 0.65-0.45 (m, 3H). |
| 78 | 417.6 | white powder | 99 | 418.3 | 5.63-5.58 (m, 1H(C7)), 4.65 (s, 1H), 4.42 (d, 1H), 4.38-4.33 (m, 1H), 3.75 (s, 1H), 3.67-3.53 (m, 1H), 3.04-2.90 (m, 1H), 2.96-2.67 (m, 1H), 2.23-1.12 (m, 18H), 0.89 (d, 3H), 0.82 (s, 3H), 0.57-0.15 (m, 7H). |
| 79 | 465.6 | beige powder | 94 | 466.2 | 5.67-5.57 (m, 1H(C7)), 4.70-4.64 (m, 1H), 4.48-4.33 (m, 3H), 3.76 (s, 1H), 3.65-3.55 (m, 1H), 3.27-3.22 (m, 6H), 3.05-2.85 (m, 1H), 2.26-1.10 (m, 20H), 0.87-0.73 (m, 6H), 0.64-0.47 (m, 3H). |
| 80 | 441.6 | yellow powder | 99 | 442.1 | 6.25-5.75 (m, 1H), 5.65-5.61 (m, 1H(C7)), 4.71-4.66 (m, 1H), 4.48-4.40 (m, 1H), 4.39-4.35 (m, 1H), 3.76 (s, 1H), 3.65-3.55 (m, 1H), 3.05-2.85 (m, 1H), 2.76-2.70 (m, 1H), 2.28-1.15 (m, 19H), 0.90-0.80 (m, 6H), 0.62-0.46 (m, 3H). |

[1]LCMS purity, UV at 254 nm

-continued

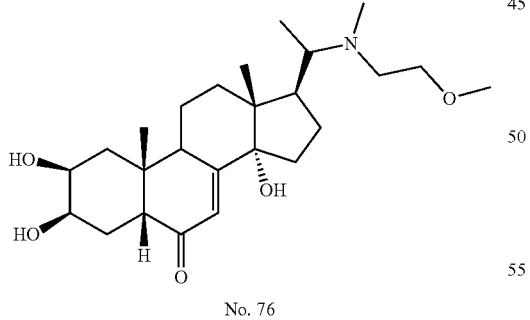

No. 76

Example 7

Scheme G

Preparation of Compound No. 81: (2S,3R,5R,10R,13R,14S,17S)-2,3,14-trihydroxy-10,13-dimethyl-17-(2-morpholinoacetyl)-2,3,4,5,9,11,12,15,16,17-decahydro-1H-cyclopenta[a]phenanthren-6-one

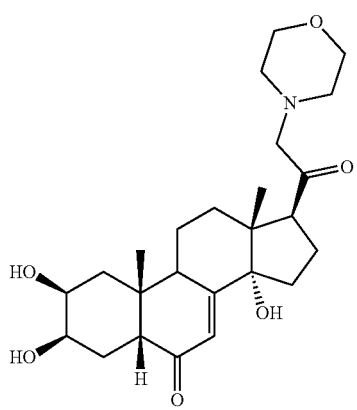

No. 81

Step 1: Preparation of Compound No. 102: (2S,3R, 5R,10R,13R,14S,17S)-17-(2-bromoacetyl)-2,3,14-trihydroxy-10,13-dimethyl-2,3,4,5,9,11,12,15,16,17-decahydro-1H-cyclopenta[a]phenanthren-6-one

Step 2: Preparation of Compound No. 81: (2S,3R, 5R,10R,13R,14S,17S)-2,3,14-trihydroxy-10,13-dimethyl-17-(2-morpholinoacetyl)-2,3,4,5,9,11,12,15,16, 17-decahydro-1H-cyclopenta[a]phenanthren-6-one

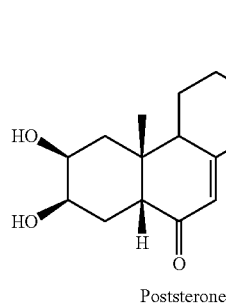

Poststerone

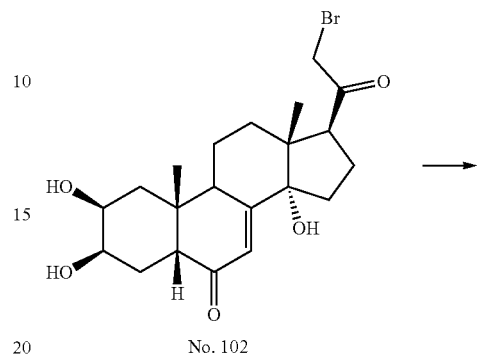

No. 102

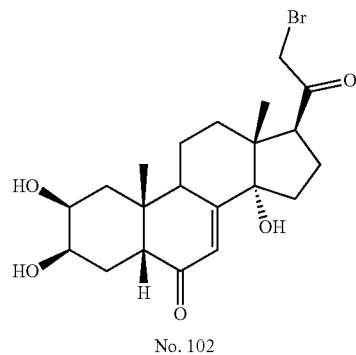

No. 102

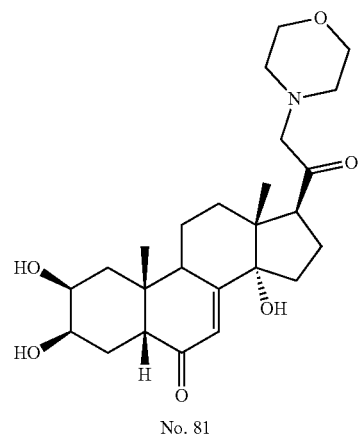

No. 81

1 g (2.76 mmol) of poststerone (obtained by oxidative cleavage of the chain of 20-hydroxyecdysone according to the same procedure as that described in step 2 of scheme B) is dissolved in 20 ml of methanol. The solution is cooled to 0° C. and 0.284 ml (5.52 mmol) of bromine is added dropwise and the reaction medium is stirred for 1 h at this temperature, then left at ambient temperature for 16 h. The reaction medium is poured onto 50 ml of a saturated sodium bicarbonate solution and extracted three times with 100 ml of ethyl acetate. The organic phases are washed with 50 ml of saturated sodium bicarbonate solution, then salt water, dried over sodium sulfate, and filtered, and the solvent is evaporated off to give 833 mg of powder, which, taken up in 30 ml of dichloromethane, gives, after filtration and desiccation, 412 mg (yield: 31%) of compound No. 102: 2S,3R, 5R,10R,13R,14S,17S)-17-(2-bromoacetyl)-2,3,14-trihydroxy-10,13-dimethyl-2,3,4,5,9,11,12,15,16,17-decahydro-1H-cyclopenta[a]phenanthren-6-one in the form of a yellow powder.

Compound No. 102:

LC-MS: m/z=443.1 (MH$^+$) UV purity at 254 nm=91%.

$^1$H NMR (300 MHz, DMSO-d$_6$) δ 5.69-5.63 (m, 1H(C7)), 5.08 (s, 1H), 4.42-4.35 (m, 3H), 4.33-4.22 (m, 1H), 3.77 (s, 1H), 3.66-3.58 (m, 1H), 3.39 (t, 1H), 3.10-2.95 (m, 1H), 2.25-1.20 (m, 13H), 0.83 (s, 3H), 0.51 (s, 3H).

50 mg (0.103 mmol) of compound No. 102 [(2S,3R,5R, 10R,13R,14S,17S)-17-(2-bromoacetyl)-2,3,14-trihydroxy-10,13-dimethyl-2,3,4,5,9,11,12,15,16,17-decahydro-1H-cyclopenta[a]phenanthren-6-one] are dissolved in 1 ml of DMF and 42.7 mg of potassium carbonate are added, along with 10.78 µl (0.124 mmol) of morpholine. After stirring for 18 h at 20° C., the reaction medium is poured onto 10 ml of water and this aqueous phase is extracted two times with 15 ml of butanol. The organic phase is evaporated off to give 71 mg of powder purified by flash chromatography on a silica gel cartridge (90/10 dichloromethane/MeOH) to give 28 mg (yield: 60%) of compound No. 81: (2S,3R,5R,10R,13R,14S, 17S)-2,3,14-trihydroxy-10,13-dimethyl-17-(2-morpholinoacetyl)-2,3,4,5,9,11,12,15,16,17-decahydro-1H-cyclopenta [a]phenanthren-6-one in the form of a white powder.

Compound No. 81:

LC-MS: m/z=448.4 (MH$^+$) UV purity at 254 nm=99%.

$^1$H NMR (300 MHz, DMSO-d$_6$) δ 5.65 (s, 1H(C7)), 5.02 (s, 1H), 4.45 (d, 1H), 4.40-4.37 (m, 1H), 3.77 (s, 1H), 3.68-3.53 (m, 5H), 3.34-3.24 (m, 4H), 3.08-2.95 (m, 1H), 2.45-1.17 (m, 16H), 0.82 (s, 3H), 0.48 (s, 3H).

Compounds No. 82 to 94 were prepared according to the same scheme.

| No. | MW g/mol | Appearance | Purity[1] (%) | MS m/z MH$^+$ | $^1$H NMR (300 MHz, DMSO-d$_6$) δ |
|---|---|---|---|---|---|
| 82 | 474.6 | orange powder | 99 | 475.3 | 5.65 (s, 1H(C7)), 5.03 (s, 1H), 4.49-4.38 (m, 2H), 3.77 (s, 1H), 3.68-3.53 (m, 1H), 3.3-3.1 (m, 4H), 3.08-2.95 (m, 1H), 2.9-2.45 (m, 6H), 2.28-0.92 (m, 19H), 0.82 (s, 3H), 0.48 (s, 3H). |

-continued

| No. | MW g/mol | Appearance | Purity[1] (%) | MS m/z MH+ | $^1$H NMR (300 MHz, DMSO-d$_6$) δ |
|---|---|---|---|---|---|
| 83 | 475.6 | white powder | 99 | 476.6 | 5.65 (s, 1H(C7)), 5.01 (s, 1H), 4.45 (d, 1H), 4.41-4.38 (m, 1H), 3.77 (s, 1H), 3.7-3.48 (m, 3H), 3.35-3.23 (m, 2H), 3.08-2.95 (m, 1H), 2.72-2.55 (m, 2H), 2.28-2 (m, 3H), 1.9-1.38 (m, 12H), 1.35-1.18 (m, 1H), 1.05-0.85 (m, 6H), 0.82 (s, 3H), 0.48 (s, 3H). |
| 84 | 462.6 | yellow powder | 99 | 463.3 | 5.66 (s, 1H(C7)), 5.08 (s, 1H), 4.55-4.25 (m, 2H), 3.77 (s, 1H), 3.70-3.45 (m, 4H), 3.25-2.90 (m, 5H), 2.80-2.60 (m, 6H), 2.33-1.15 (m, 16H), 0.83 (s, 3H), 0.50 (s, 3H). |
| 85 | 479.6 | yellow oil | 99 | 480.3 | 5.65 (s, 1H(C7)), 5.01 (s, 1H), 4.48-4.37 (m, 3H), 3.77 (s, 1H), 3.70-3.52 (m, 1H), 3.25 (s, 6H), 3.25-2.90 (m, 1H), 2.57-2.47 (m, 2H), 2.3-1.19 (m, 19H), 0.82 (s, 3H), 0.48 (s, 3H). |
| 86 | 447.6 | orange oil | 99 | 448.2 | 5.67 (s, 1H(C7)), 5.44-5.39 (m, 1H), 5.14 (s, 1H), 4.5-4.15 (m, 5H), 3.77 (s, 1H), 3.68-3.55 (m, 1H), 3.27-3.15 (m, 4H), 3.25-2.90 (m, 1H), 2.25-1.17 (m, 16H), 0.83 (s, 3H), 0.54 (s, 3H). |
| 87 | 435.6 | colorless oil | 99 | 436.2 | 5.65 (s, 1H(C7)), 5.02 (s, 1H), 4.49-4.38 (m, 3H), 3.77 (s, 1H), 3.68-3.55 (m, 1H), 3.52-3.36 (m, 2H), 3.30-3.18 (m, 2H), 3.25-2.95 (m, 1H), 2.30-1.17 (m, 19H), 0.82 (s, 3H), 0.48 (s, 3H). |
| 88 | 461.6 | white powder | 99 | 462.2 | 5.65 (s, 1H(C7)), 5.02 (s, 1H), 4.58 (s, 1H), 4.46 (s, 1H), 4.42-4.39 (m, 1H), 3.77 (s, 1H), 3.68-3.55 (m, 1H), 3.48-3.33 (m, 1H), 3.31-3.17 (m, 2H), 3.08-2.95 (m, 1H), 2.70-2.56 (m, 2H), 2.3-1.18 (m, 20H), 0.82 (s, 3H), 0.47 (s, 3H). |
| 89 | 489.7 | colorless oil | 99 | 490.3 | 5.65 (s, 1H(C7)), 5.01 (s, 1H), 4.48-4.30 (m, 3H), 3.77 (s, 1H), 3.68-3.55 (m, 1H), 3.45-3.35 (m, 2H), 3.28-3.11 (m, 2H), 3.08-2.95 (m, 1H), 2.85-2.58 (m, 2H), 2.28-1.03 (m, 23H), 0.82 (s, 3H), 0.47 (s, 3H). |
| 90 | 459.6 | colorless oil | 99 | 460.3 | 5.64 (s, 1H(C7)), 5.01 (s, 1H), 4.49-4.38 (m, 2H), 3.77 (s, 1H), 3.68-3.55 (m, 1H), 3.25-3.20 (m, 1H), 3.10-2.85 (m, 2H), 2.77-2.61 (m, 2H), 2.25-1.03 (m, 21H), 0.88 (d, 3H), 0.82 (s, 3H), 0.47 (s, 3H). |
| 91 | 476.7 | yellow powder | 99 | 477.3 | 5.66 (s, 1H(C7)), 5.10 (s, 1H), 4.55-4.40 (m, 2H), 3.77 (s, 1H), 3.68-3.55 (m, 1H), 3.22 (t, 2H), 3.15-2.93 (m, 3H), 2.75 (s, 6H), 2.35-1.20 (m, 21H), 0.83 (s, 3H), 0.51 (s, 3H). |
| 92 | 480.6 | white powder | 99 | 481.1 | 5.65 (s, 1H(C7)), 5.06 (s, 1H), 4.46 (d, 1H), 4.41-4.38 (m, 1H), 4.08 (q, 2H), 3.77 (s, 1H), 3.68-3.51 (m, 3H), 3.32 (s, 2H), 3.08-2.90 (m, 1H), 2.28-1.25 (m, 14H), 1.19 (t, 3H), 0.82 (s, 3H), 0.49 (s, 3H). |
| 93 | 422.6 | white powder | 99 | 423.1 | 5.65 (s, 1H(C7)), 5.06 (s, 1H), 4.46 (d, 1H), 4.41-4.38 (m, 1H), 3.77 (s, 1H), 3.68-3.51 (m, 1H), 3.50-3.36 (m, 2H), 3.08-2.90 (m, 1H), 2.48-2.40 (m, 2H), 2.28-1.20 (m, 14H), 1.14 (t, 3H), 0.82 (s, 3H), 0.51 (s, 3H). |
| 94 | 438.6 | white powder | 99 | 439.2 | 5.65 (s, 1H(C7)), 5.05 (s, 1H), 4.81 (t, 1H), 4.46 (d, 1H), 4.41-4.38 (m, 1H), 3.77 (s, 1H), 3.68-3.55 (m, 1H), 3.52-3.40 (m, 4H), 3.08-2.90 (m, 1H), 2.58-2.50 (m, 2H), 2.23-1.20 (m, 14H), 0.82 (s, 3H), 0.50 (s, 3H). |

[1]LCMS purity, UV at 254 nm

Example 8

Scheme H

Preparation of Compound No. 95: (2S,3R,5R,10R,13R,14S,17S)-17-(2-ethoxyacetyl)-2,3,14-trihydroxy-10,13-dimethyl-2,3,4,5,9,11,12,15,16,17-decahydro-1H-cyclopenta[a]phenanthren-6-one

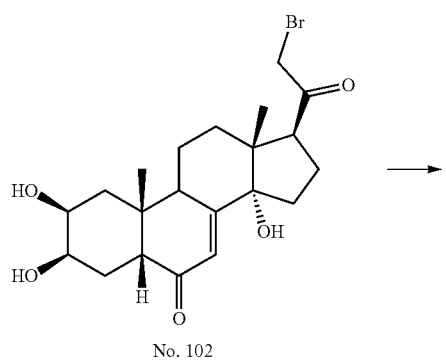

No. 102

→

100 mg (0.227 mmol) of compound No. 102 [2S,3R,5R,10R,13R,14S,17S)-17-(2-bromoacetyl)-2,3,14-trihydroxy-10,13-dimethyl-2,3,4,5,9,11,12,15,16,17-decahydro-1H-cyclopenta[a]phenanthren-6-one] prepared in step 1 of example 7 are dissolved in 2 ml of ethanol and 0.102 ml (0.272 mmol) of a solution of sodium ethoxide at 21% in ethanol, diluted in 1 ml of ethanol, is added dropwise and the solution obtained is brought to reflux for 30 min. The reaction medium cooled to 20° C. is poured onto 25 ml of water and extracted with two times 20 ml of butanol. The organic phase is evaporated off to give 30 mg of an oil purified by flash chromatography on a silica gel cartridge (95/5 dichloromethane/MeOH) to give 13.5 mg (yield: 14%) of compound No. 95: (2S,3R,5R,10R,13R,14S,17S)-17-(2-ethoxyacetyl)-2,3,14-trihydroxy-10,13-dimethyl-2,3,4,5,9,11,12,15,16,17-decahydro-1H-cyclopenta[a]phenanthren-6-one in the form of a yellow oil.

Compound No. 95:

LC-MS: m/z=407.2 (MH$^+$) UV purity at 254 nm=93%.

$^1$H NMR (300 MHz, DMSO-d$_6$) δ 5.65-5.59 (m, 1H(C7)), 4.96 (s, 1H), 4.46 (d, 1H), 4.41-4.36 (m, 1H), 4.03 (q, 2H), 3.77 (s, 1H), 3.68-3.55 (m, 1H), 3.08-2.90 (m, 1H), 2.75-2.62 (m, 1H), 2.3-2.15 (m, 2H), 1.92-1.42 (m, 13H), 1.18 (t, 3H), 0.83 (s, 3H), 0.58-0.49 (m, 3H).

Compound No. 96 was prepared according to the same scheme

| No. | MW g/mol | Appearance | Purity[1] (%) | MS m/z MH$^+$ | $^1$H NMR(300 MHz, DMSO-d$_6$) δ |
|---|---|---|---|---|---|
| 96 | 448.6 | white powder | 99 | 449.1 | 5.61 (s, 1H(C7)), 5.23-5.15 (m, 1H), 4.97 (s, 1H), 4.48-4.42 (m, 1H), 4.39-4.35 (m, 1H), 3.82-3.55 (m, 6H), 3.08-2.90 (m, 1H), 2.72-2.55 (m, 1H), 2.32-1.17 (m, 17H), 0.83 (s, 3H), 0.58 (s, 3H). |

[1]LCMS purity, UV at 254 nm

-continued

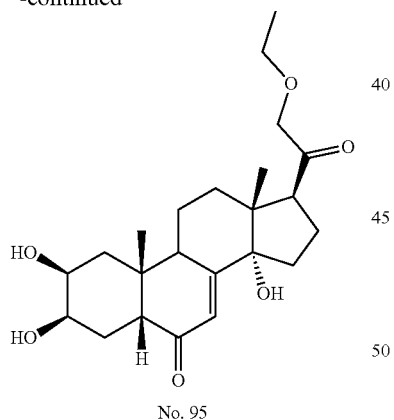

No. 95

Example 9

Scheme I

Preparation of Compound No. 97: (2S,3R,5R,10R,13R,14S,17S)-2,3,14-trihydroxy-17-[1-hydroxy-2-(2-hydroxyethyl(methyl)amino)ethyl]-10,13-dimethyl-2,3,4,5,9,11,12,15,16,17-decahydro-1H-cyclopenta[a]phenanthren-6-one

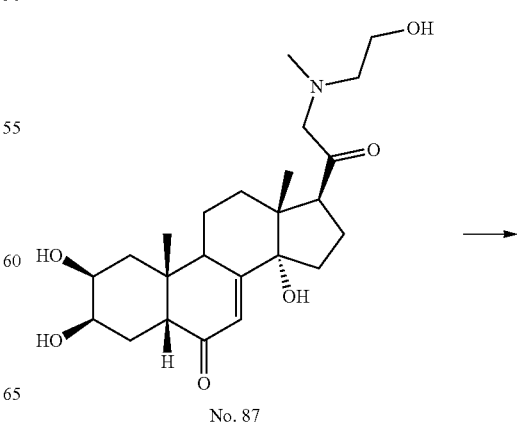

No. 87

→

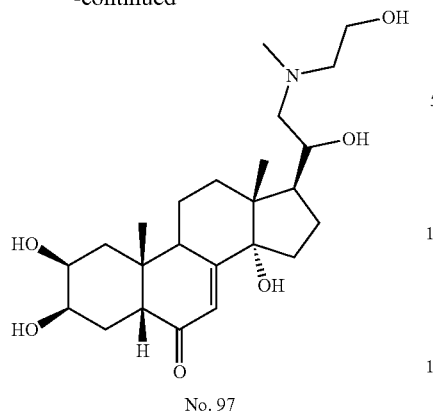

No. 97

157 mg (0.360 mmol) of compound No. 87 [(2S,3R,5R, 10R,13R,14S,17S)-2,3,14-trihydroxy-17-[2-(2-hydroxyethyl(methyl)amino)acetyl]-10,13-dimethyl-2,3,4,5,9,11, 12,15,16,17-decahydro-1H-cyclopenta[a]phenanthren-6-one] obtained according to the method of step 2 of example 7 are dissolved in 7.5 ml of ethanol and 21.14 mg (0.559 mmol) of sodium borohydride are added portionwise. After stirring for 16 h at 20° C., the reaction medium is poured onto 20 ml of water and extracted with three times 15 ml of butanol. The organic phase is evaporated off to give a powder purified by flash chromatography on a silica gel cartridge (85/14/1 dichloromethane/MeOH/NH$_4$OH) to give 96 mg (yield: 60%) of compound No. 97: (2S,3R,5R,10R, 13R,14S,17S)-2,3,14-trihydroxy-17-[1-hydroxy-2-(2-hydroxyethyl(methyl)amino)ethyl]-10,13-dimethyl-2,3,4,5,9, 11,12,15,16,17-decahydro-1H-cyclopenta[a]phenanthren-6-one in the form of a white powder.

Compound No. 97:

LC-MS: m/z=438.2 (MH$^+$) UV purity at 254 nm=99%.

$^1$H NMR (300 MHz, DMSO-d$_6$) δ 5.6 (s, 1H(C7)), 5.32-5.2 (m, 2H), 4.77 (s, 1H), 4.47 (d, 1H), 4.42-4.38 (m, 1H), 3.92-3.57 (m, 4H), 3.3-2.95 (m, 4H), 2.82 (s, 3H), 2.31-1.18 (m, 16H), 0.85 (s, 3H), 0.69 (s, 3H).

$^{13}$C NMR (75 MHz, DMSO-d$_6$)δ 203.2, 164.9, 121.0, 82.8, 66.9, 59.0, 55.6, 50.6, 46.9, 40.7, 37, 34, 31.9, 31.1, 30.3, 24.5, 23.2, 20.4, 16.3.

Compounds No. 98 to 100 were prepared according to the same scheme.

Example 10

Scheme J

Preparation of Compound No. 101: (2S,3R,5R,6E, 10R,13R,14S,17S)-6-methoxyimino-17-(N-methoxy-C-(morpholinomethyl)carbonimidoyl)-10, 13-dimethyl-2,3,4,5,9,11,12,15,16,17-decahydro-1H-cyclopenta[a]phenanthrene-2,3,14-triol

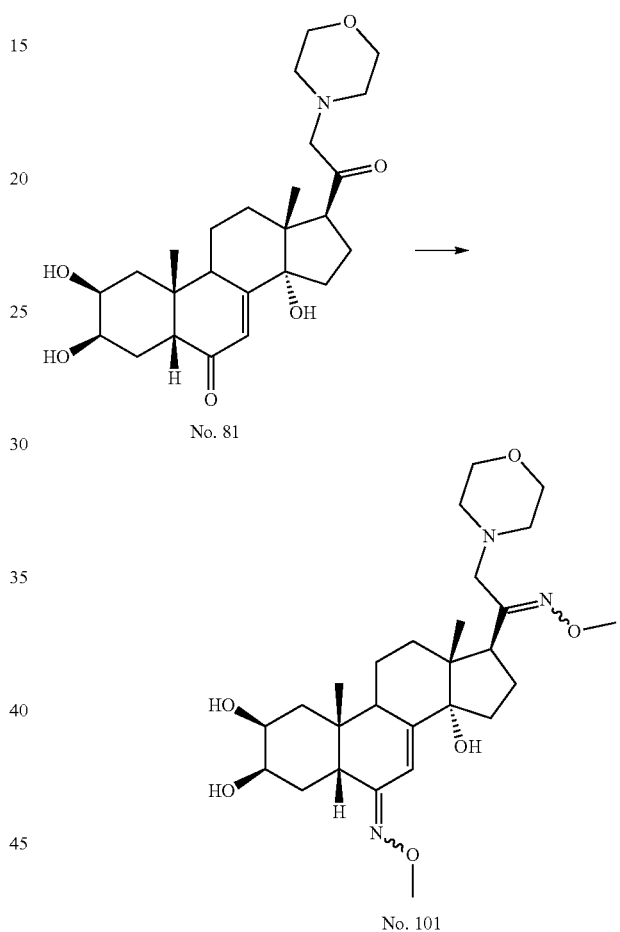

| No. | MW g/mol | Appearance | Purity[1] (%) | MS m/z MH$^+$ | $^1$H NMR (300 MHz, DMSO-d$_6$) δ |
|-----|----------|------------|---------------|---------------|-----------------------------------|
| 98  | 440.6    | white powder | 99          | 441.1         | 5.6 (s, 1H(C7)), 4.76 (t, 1H), 4.65 (s, 1H), 4.47 (d, 1H), 4.43 (d, 1H), 4.36-4.33 (m, 1H), 3.76 (s, 1H), 3.82-3.55 (m, 1H), 3.53-3.45 (m, 3H), 3.08-2.90 (m, 1H), 2.65-2.55 (m, 3H), 2.45-1.10 (m, 15H), 0.84 (s, 3H), 0.63 (s, 3H). |
| 99  | 491.66   | white powder | 99          | 492.2         | 5.61 (s, 1H(C7)), 4.70-4.62 (m, 1H), 4.48-4.28 (m, 3H), 3.76 (s, 1H), 3.65-3.55 (m, 1H), 3.53-3.31 (m, 3H), 3.03-2.84 (m, 2H), 2.78-2.65 (m, 1H), 2.25-1.04 (m, 26H), 0.84 (s, 3H), 0.70-0.55 (m, 3H). |
| 100 | 449.58   | orange oil  | 98           | 450.2         | (in DMSO + D2O) δ 5.65-5.58 (m, 1H(C7)), 4.23-4.13 (m, 1H), 3.75 (s, 1H), 3.04-2.93 (m, 1H), 2.87-2.65 (m, 2H), 2.25-1.10 (m, 22H), 0.83 (s, 3H), 0.63 (m, 3H). |

[1]LCMS purity, UV at 254 nm

30 µl (0.301 mmol) of methoxylamine hydrochloride are dissolved in 0.6 ml of pyridine and 136 mg (0.301 mmol) of compound No. 81 [(2S,3R,5R,10R,13R,14S,17S)-2,3,14-trihydroxy-10,13-dimethyl-17-(2-morpholinoacetyl)-2,3,4,5,9,11,12,15,16,17-decahydro-1H-cyclopenta[a]phenanthren-6-one] prepared in step 2 of example 7 are added portionwise. After stirring for 36 h at 20° C., the reaction medium is taken up in 10 ml of dichloromethane and this solution is washed two times with salt water, dried over sodium sulfate, filtered and evaporated to give a powder purified by flash chromatography on a silica gel cartridge (90/10 dichloromethane/MeOH) to give 81 mg (yield: 53%) of compound No. 101: (2S,3R,5R,6E,10R,13R,14S,17S)-6-methoxyimino-17-(N-methoxy-C-(morpholinomethyl)carbonimidoyl)-10,13-dimethyl-2,3,4,5,9,11,12,15,16,17-decahydro-1H-cyclopenta[a]phenanthrene-2,3,14-triol in the form of a yellow powder.

Compound No. 101:

LC-MS: m/z=506.2 (MH$^+$) UV purity at 254 nm=99%.

$^1$H NMR (300 MHz, DMSO-d$_6$) δ mixture of C6 (Z) and (E) conformers: 6.28 (s,0.45H (C7-conformer E), 5.72 (s,0.55H (C7-conformer Z), 4.62 (s,0.45H-conformer E), 4.53 (s,0.55H-conformer Z), 4.47-4.35 (m,1H), 4.33-4.21 (m,1H), 3.77-3.70 (m,7H), 3.60-3.48 (m,5H), 3.16-3.06 (m,1H), 2.90-2.70 (m,2H), 2.45-1.20 (m,18H), 0.72 (s,3H), 0.64-0.57 (m, 3H).

Cascade for Screening and Characterization of the Biological Effects of the 20-Hydroxyecdysone Derivatives The development of the screening test was initiated on the basis of the studies in the literature and was based on the characteristics of the pathology of sarcopenia. At the physiopathological level, this disease is characterized by a decrease in protein synthesis and an increase in proteolysis. The development of future medicaments should thus be screened on molecular factors in relation to these two phenomena.

At the cellular level, on cultures of muscle cells derived from the C2C12 murine line, Gorelick-Feldman et al. (2008) showed that treatment with phytoecdysones increases protein synthesis by +20% on average. The first development studies were based on the culture and treatment conditions described by Gorelick-Feldman in the presence of reference products (IGF-1 and 20-hydroxyecdysone or 20E). Measurements of tritiated leucine incorporation into these cells were carried out in order to evaluate the de novo protein synthesis. These first results made it possible to determine that the optimal sequence for observing the effects of phytoecdysones on protein synthesis was to differentiate the cells for 5 days, then to add the tritiated leucine for 2 h 30 in the presence of IGF-1 or of 20E.

The analysis of the literature showed that molecules such as IGF-1 increased protein synthesis only by 20%, while at the same time activating targets of this signaling pathway in a more sustained manner that could reach stimulations of about 200% [Kazi et al., 2010]. These targets comprise phosphorylations that activate proteins such as Akt or S6 kinase. Furthermore, in the same C2C12 cell system, Zubeldia et al. (2012) analyzed the phenomena of apoptosis and proteolysis. In their study, they in particular reported that plant extracts containing phytoecdysones such as turkesterone or 20E were capable, after 24 h of treatment of differentiated C2C12 cells, of inhibiting myostatin and caspase 3 gene expression by a factor of 4 and 2, respectively [Zubeldia et al., 2012].

After several experiments in which the C2C12 cells differentiated into myotubes were incubated in the presence of IGF-1 or 20E for 2 h 30 or 6 h, two screening tests were developed. Thus, the phosphorylation of the S6 protein kinase and the expression of the myostatin gene were studied in order to determine their modulation by a growth hormone or an ecdysone and to characterize these modulations from a statistical point of view.

Protocols

Inhibition of Myostatin Expression in C2C12 Cells:

The C2C12 myoblast cells (ATCC CRL-1772) are seeded into 24-well plates at a density of 30 000 cells per well and cultured in a DMEM medium containing glucose in a proportion of 4.5 g/l and supplemented with fetal calf serum (10%) and with antibiotics (penicillin and streptomycin). Forty-eight hours later, the myoblasts are induced to differentiate by partial serum depletion (2% instead of 10%) for 5 days. The cells are then placed in a medium which is glucose-depleted (DMEM containing 1 g/l of glucose) and serum-free in the presence of the test molecules or of the references (100 ng/ml IGF-1 or 10 µM 20E) for 6 h. At the end of the experiment, the messenger RNAs (mRNAs) are extracted using the conventional methodology based on phenol and chloroform. Briefly, the cells are lysed in a Trizol solution (Sigma T9424) containing a strong acid and phenol. The mRNAs are separated from the proteins by addition of chloroform and then centrifugation. They are then precipitated from isopropanol and then suspended at a concentration of 1 µg/µl in an RNAses-free and DNAses-free ultrapure water. 1 µg of mRNA is then converted by reverse transcription into complementary DNA by the AMV enzyme in the presence of a primer and of a mixture of nucleotides according to the protocol given by the supplier (Applied Biosystems 4368814). The gene expression is studied by chain reaction initiated by a polymerase enzyme and commonly referred to as PCR under quantitative conditions, hence the specific name qPCR. The qPCRs are carried out on a 7900HT Fast real-Time PCR detection system (Applied Biosystems). The programming conditions are standard and consist of 1 cycle at 95° C. for 15 min, followed by 40 cycles at 95° C. for 15 s and at 60° C. for 1 min and the program ends with a melt curve step between 60° C. and 95° C. The samples analyzed all contain 100 ng of cDNA, a qPCR buffer including the enzyme, the mixture of oligonucleotides and the intercalating agent (sybergreen or SYBRgreen), and the pair of primers specific for the gene studied, strategically chosen between two exon sequences and at a final concentration of 200 nM. Fluorescent probes bind to the double-stranded DNA and are fluorescent only once bound to the DNA. A fluorescence threshold is established by the machine's program. When the amount of DNA allows the fluorescent probe to exceed this threshold, a PCR cycle number, called "Ct" for "Cycle Threshold", is obtained. It is this value which forms the basis of the calculations to quantify the DNA relatively. A ratio R is established between the amount of starting DNA of a sample and that of a control, which has not undergone treatment (i.e. $R = 2^{-(Ct\ sample - Ct\ control)}$) and this measurement will be related to that of a housekeeping gene known not to be modulated by the treatment (i.e. $R = 2^{-\Delta\Delta Ct}$).

The primers used are reported in the following table:

TABLE 3 primers used to evaluate the gene expression modifications

| Gene | 5' → 3' sequence | Number of bases | Tm | Accession No. |
|---|---|---|---|---|
| Myostatin d | GAGTCTGACTTTCTAATGCAAG | 21 | 62 | mouse: NM_010834 |
| Myostatin ind | TGTTGTAGGAGTCTTGACGG | 20 | 60 | rat: AF019624 |
| Atrogin d | AGAGTCGGCAAGTCTGTGCT | 20 | 62 | mouse: AF441120 |
| Atrogin ind | GTGAGGCCTTTGAAGGCAG | 19 | 60 | human: NM_058229 |
| beta-actin d | CTCTAGACTTCGAGCAGGAG | 20 | 62 | mouse: X03672 |
| beta-actin ind | GGTACCACCAGACAGCACT | 19 | 60 | |

Phosphorylation of the S6 Kinase:

The C2C12 myoblast cells (ATCC CRL-1772) are seeded into 6-well plates at a density of 170 000 cells per well and cultured in a DMEM medium containing glucose in a proportion of 4.5 g/l and supplemented with fetal calf serum (10%) and with antibiotics (penicillin and streptomycin). Forty-eight hours later, the myoblasts are induced to differentiate by partial serum depletion (2% instead of 10%) for 5 days. The cells are then placed in a medium which is glucose-depleted (DMEM containing 1 g/l of glucose) and serum-free in the presence of the test molecules or of the references (100 ng/ml IGF-1 or 10 µM 20E) for 2 h. At the end of the experiment, the cells are lysed in a commercial lysis buffer (Invitrogen FNN0011) supplemented with a commercial mixture of anti-proteases (Roche 05056489001). After centrifugation, the cytoplasmic fraction containing the soluble proteins is kept and the protein concentration is determined using a commercial kit (Biorad 500-0114), the principle of which is composed of assaying by the Lowry method. The assaying of the S6 kinase phosphorylation is carried out using a commercial ELISA (Enzyme Linked ImmunoSorbent Assay) kit (Cell signaling 7063). Briefly, 50 µg of protein lysate are deposited in the wells of a 96-well microplate and incubated overnight at 4° C. with the solution of antigen specific for the pS6 kinase threonine 389 antibody. The binding of the antigen to the bottom of the wells is done electrostatically. The solution of antibody to be assayed (pS6K T389) is then incubated at 37° C. in the wells for 2 hours. The antibodies bind specifically to the antigen. The wells are then washed with washing buffer in order to remove the antigen-specific primary antibodies to be assayed which are in excess. The third step consists in binding the detection antibody. The solution of detection antibodies is incubated at 37° C. in the wells for 1 hour. The wells are then washed in order to remove the excess detection antibodies. It should be noted that the detection antibodies are coupled to an enzyme which, in the presence of its substrate, converts it into a reaction product that can be detected and measured by virtue of the appearance of a coloration. The final step consists in revealing the bound antibodies. A revealing solution containing the substrate for the enzyme, in this case TMB (3,3',5,5'-tetramethylbenzidine), is incubated at 37° C. in the dark for 30 min. The appearance of a blue coloration in the substrate indicates the presence of the antibody to be assayed. In order to prevent any saturation phenomenon, a stop solution (generally containing sodium hydroxide) is added and brings about a change in coloration, which goes from blue to yellow. The strength thereof is proportional to the amount of enzyme present and thus to the concentration of antibody sought.

The strength of the signal is measured using spectrophotometry at a wavelength of 450 nm.

Evaluation of the Effect of the Molecules in a Model of Mice Subjected to a High-fat Diet The 20E as comparative compound and the compounds according to the invention (Nos. 51 and 93) were administered orally, at a dose of 5 mg/kg of body weight, to 12-week-old C57BL/6J mice subjected to a high-fat diet for 6 weeks. The effect of the compounds on the weight and the amount of proteins of the Soleus muscle and also the transcripts of genes involved in myogenesis were evaluated.

Myogenesis, which is the process for forming muscle tissues, is controlled by several myogenic transcription factors which act as end effectors of the signaling cascade and produce transcripts involved in the various stages of development. The roles of the transcription factors have been described in various journals (Sabourin and Rudnicki 2000 and Le Grand and Rudnicki 2007). The Pax7 protein (Paired-box protein 7) maintains a population of satellite cells in quiescence and, with Myf5 (Myogenic factor 5), plays a role in the expansion of activated myoblasts. The MyoD protein (Myoblast Determination protein) appears to determine the differentiation potential of activated myoblasts, and cooperates with myogenin and the MEF2 (Myocyte Enhancer Factor 2) protein to control and bring about differentiation. Finally, MRF4 (Muscle-specific Regulatory Factor 4) is required for hypertrophy, even though it probably plays other roles. Quite obviously, these transcription factors do not act alone, but exist in the context of complex signaling cascades which control each step of myogenesis (Knight and Kothary, 2011).

The amount of proteins is determined by first lysing the muscles sampled in a 0.1N NaOH solution with the FastPrep technique. The proteins are quantified by means of a colorimetric assay derived from the Lowry method.

In order to carry out the gene expression analysis, the muscle tissues were homogenized in a Trizol solution (500 µl), and the RNAs were extracted and purified using the phenol/chloroform method. An amount of 1 pg of RNA was used as template for the synthesis of the first cDNA strand using oligo (dT)s as primers and the AMV reverse transcriptase enzyme as described by the supplier (Applied Biosystems 4368814). The q-PCRs were then carried out using a 7900HT machine equipped with a rapid system for real-time detection by PCR (Applied Biosystems) and the standard qPCR program (1 cycle of 95° C. for 15 min, 40 cycles of 95° C. for 15 s and 60° C. for 1 min, a 60-95° C. melt curve for the Sybergreen probes). The experiments are carried out in a Sybergreen SYBR master mix (Applied Biosystems) containing the 100 ng cDNA samples and a set of primers which bind to the two different exons and at a final concentration of 200 nM.

The relative differences in gene expression between treatments are expressed as increase or decrease in the number of cycle times [Ct] compared with the control group, the [Ct] value of each gene having been standardized with the beta-actin gene.

Oral Pharmacokinetic Study of the Molecules in Rats

The pharmacokinetics of the compounds were evaluated orally using male Wistar rats (Charles River). The 20E as comparative compound was administered at a dose of 50 mg/kg of body weight. The novel compounds according to the invention were administered at a dose of 10 mg/kg of body weight in the form of a mixture of 4 to 6 products. After administration, the blood was sampled from the tail at t=0.25 h, 0.5 h, 1 h, 3 h, 6 h and 8 h. The blood samples were centrifuged and the plasmas removed. The assaying of the plasma samples made it possible to determine the pharmacokinetic parameters, namely the $C_{max}$, which corresponds to the maximum concentration observed after the administration of the molecule, the $T_{max}$, which is the time required to reach the maximum concentration after administration of the molecule, and the AUC: area under the curve composed of the various concentrations of compounds at the various sampling times.

Results

The Effects on Myostatin Expression

TABLE 4 effects on myostatin expression. The results are expressed as percentage myostatin gene expression in the cells in contact with the compounds related to the expression in the control cells. A represents a percentage of less than 70%, B represents a percentage between 71% and 85%. Compounds are tested at a concentration of 10 μM.

| Number | Myostatin gene expression |
|---|---|
| 4 | A |
| 5 | A |
| 7 | A |
| 19 | B |
| 21 | A |
| 23 | B |
| 25 | A |
| 27 | A |
| 28 | A |
| 29 | A |
| 30 | B |
| 31 | A |
| 32 | A |
| 33 | A |
| 35 | B |
| 36 | B |
| 37 | B |
| 38 | A |
| 41 | A |
| 43 | A |
| 46 | A |
| 47 | A |
| 48 | B |
| 51 | A |
| 52 | A |
| 53 | A |
| 54 | A |
| 56 | B |
| 57 | B |
| 60 | B |

TABLE 4-continued effects on myostatin expression. The results are expressed as percentage myostatin gene expression in the cells in contact with the compounds related to the expression in the control cells. A represents a percentage of less than 70%, B represents a percentage between 71% and 85%. Compounds are tested at a concentration of 10 μM.

| Number | Myostatin gene expression |
|---|---|
| 62 | A |
| 63 | A |
| 64 | A |
| 65 | A |
| 67 | A |
| 68 | A |
| 71 | A |
| 73 | B |
| 75 | A |
| 76 | A |
| 79 | A |
| 81 | A |
| 83 | B |
| 85 | B |
| 86 | A |
| 88 | B |
| 89 | A |
| 91 | B |
| 92 | A |
| 93 | A |
| 94 | A |
| 99 | A |
| 101 | A |

The following 38 compounds: 4, 5, 7, 21, 25, 27 to 29, 31 to 33, 38, 41, 43, 46, 47, 51 to 54, 62 to 65, 67, 68, 71, 75, 76, 79, 81, 86, 89, 92 to 94, 99 and 101 very significantly inhibit myostatin expression in muscle cells.

The following 15 compounds: 19, 23, 30, 35 to 37, 48, 56, 57, 60, 73, 83, 85, 88 and 91 significantly inhibit myostatin expression in muscle cells.

The Effects on Protein Synthesis Via S6K1 Phosphorylation

TABLE 5 effects on protein synthesis. The results are expressed as percentage increase in S6K phosphorylation in muscle cells. A represents values greater than 130%, B represents values of between 110% and 129%. The compounds are tested at a concentration of 10 μM.

| Number | Protein synthesis |
|---|---|
| 28 | A |
| 32 | B |
| 41 | B |
| 42 | A |
| 43 | B |
| 46 | B |
| 51 | B |
| 52 | B |
| 62 | A |
| 63 | B |
| 67 | A |
| 76 | B |
| 81 | B |
| 86 | A |
| 88 | B |
| 89 | A |
| 91 | B |
| 92 | B |
| 93 | A |
| 94 | A |

The following 8 compounds: 28, 42, 62, 67, 86, 89, 93 and 94 very significantly stimulate S6Ka phosphorylation at levels equivalent to IGF-1 (130-140%).

The following 12 compounds: 32, 41, 43, 46, 51, 52, 63, 76, 81, 88, 91 and 92 significantly stimulate S6K1 phosphorylation at levels equivalent to that of 20E (120%).

Study of the Molecules in a Model of Mice Subjected to a High-fat Diet

The in vivo study is carried out by evaluating the effect of 20E as comparative compound and of the molecules according to the invention (Nos. 51 and 93) administered orally, at a dose of 5 mg/kg of body weight, to C57BL/6 mice subjected to a high-fat diet for 6 weeks. The effect of the molecules on the weight and the amount of proteins of the Soleus muscle and also the transcripts of genes involved in myogenesis were evaluated.

Figure 3A:
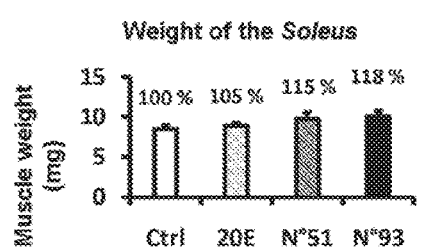
FIG. 3A illustrates the effects of 20E (comparative compound) and of compounds in accordance with the invention Nos. 51 and 93 on the weight of C57BL/6 mice subjected to a high-fat diet for 6 weeks.
Figure 3B:
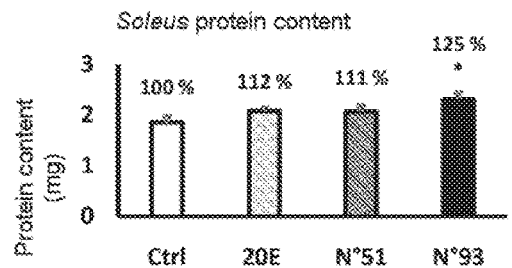
FIG. 3B illustrates the effects of 20E (comparative compound) and of compounds in accordance with the invention Nos. 51 and 93 on the amount of protein of the Soleus muscle of C57BL/6 mice subjected to a high-fat diet for 6 weeks.

The effects of 20E as comparative compound and of the compounds according to the invention Nos. 51 and 93 on the weight of the muscle are illustrated in FIG. 3A and the effects of 20E and of the compounds Nos. 51 and 93 on the amount of proteins of the Soleus muscle are illustrated in FIG. 3B.

All three of the 20E and the compounds administered at 5 mg/kg induce increases in the weight and in the amount of proteins of the Soleus muscle compared with the control group. The compounds in accordance with the invention show just as high an effectiveness as that of 20E. A significant increase in the protein content is even noted with compound No. 93.

Figure 4:
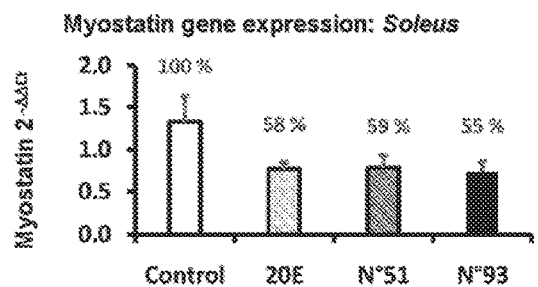
FIG. 4 illustrates the effects of 20E (comparative compound) and of compounds in accordance with the invention Nos. 51 and 93 on the myostatin transcript of the Soleus muscle of C57BL/6 mice subjected to a high-fat diet for 6 weeks.

The effects of 20E as comparative compound and of the administered compounds according to the invention No. 51 and No. 93, on the myostatin transcript of the Soleus muscle, are illustrated in FIG. 4.

The 20E and the compounds Nos. 51 and 93 comparably inhibit myostatin expression in the Soleus muscle. These molecules also inhibited the myostatin transcript in the in vitro studies in the C2C12 cell lines as presented in table 4 above.

Figure 5A:
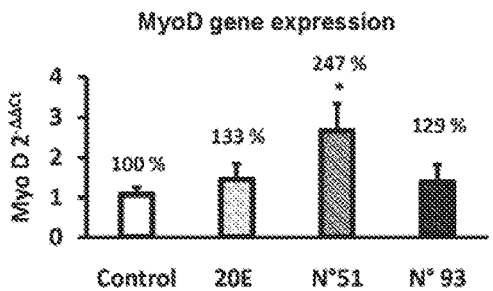
FIG. 5A illustrates the effects of 20E (comparative compound) and of compounds in accordance with the invention Nos. 51 and 93 on the MyoD transcripts of C57BL/6 mice subjected to a high-fat diet for 6 weeks.
Figure 5B:
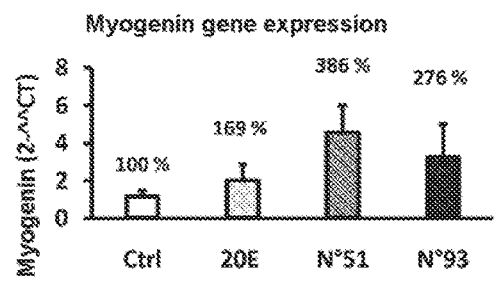
FIG. 5B illustrates the effects of 20E (comparative compound) and of compounds in accordance with the invention Nos. 51 and 93 on the myogenin transcripts of C57BL/6 mice subjected to a high-fat diet for 6 weeks.

The effects of the 20E as comparative compound and of the compounds according to the invention Nos. 51 and 93 on the transcripts of MyoD and of myogenin, which are genes involved in Soleus muscle myogenesis, are respectively illustrated in FIGS. 5A and 5B.

The 20E and compounds Nos. 51 and 93 induce an increase in the transcripts of the MyoD gene which determines the differentiation potential and the Myf5 gene involved in the proliferation of myocytes. They also induce an increase in the transcript of the myogenin gene involved in the early differentiation of the myocytes.

Pharmacokinetic Study of the Molecules in Rats

The pharmacokinetics of 20E and of compounds according to the invention were evaluated in rats by oral administration at a dose of 10 mg/kg in the case of the compounds and 50 mg/kg in the case of 20E.

TABLE 6 principal pharmacokinetic parameters ($T_{max}$; $C_{max}$ and AUC) of the 20E and of the compounds tested in Wistar rats

| Compound | Dose (mg/kg) | $T_{max}$ (h) | $C_{max}$ (ng/ml) | AUC (ng · h/ml) | Cexp |
|---|---|---|---|---|---|
| 20E | 50 | 0.5 | 68 | 382 | 1.0 |
| 31 | 10 | 0.25 | 105 | 281 | 3.7 |
| 46 | 10 | 0.25 | 40 | 202 | 2.6 |
| 51 | 10 | 0.25 | 174 | 273 | 3.6 |
| 93 | 10 | 0.5 | 230 | 785 | 10.3 |

Taking into account the 20E dose which is 5 times higher (50 mg/kg) compared with that of the compounds according to the invention (10 mg/kg), the coefficient of exposure Cexp [Cexp=(Dose$_{20E}$×AUC$_{compound}$): (Dose$_{compound}$×AUC$_{20E}$)] demonstrates the improvement in the pharmacokinetic profile of all compounds tested compared with 20E. Thus, this study in rats shows that compounds Nos. 31; 46; 51 and 93 have a better plasma exposure compared with 20E.

Overview

The table illustrated in FIG. 6 sets out the results obtained for compounds of the present invention during the experiments in which the myostatin gene expression and the protein synthesis were analyzed.

With regard to the myostatin gene expression, the results were expressed as percentage myostatin gene expression in the cells in contact with the compounds related to the expression in the control cells. A represents a percentage of less than 70%, B represents a percentage of between 71% and 85%.

With regard to the protein synthesis analysis, the results are expressed as percentage increase in S6K phosphorylation in the muscle cells. A represents values greater than 130%, B represents values of between 110% and 129%.

TABLE 7 overview regarding the results illustrated in FIG. 6

| Q | Number of examples with a myostatin gene expression category A | Number of examples with a protein synthesis category A/B | Number of the best compounds AA | Number of the best compounds AB |
|---|---|---|---|---|
| C=NOR$^5$ | 12 | 1/1 | 28 | 32 |
| CHNR$^2$R$^3$ | 19 | 3/7 | 62 and 67 | 41, 43, 46, 51, 63 and 76 |
| Carbonyl | 6 | 4/4 | 86, 89, 93 and 94 | 81 and 92 |
| CHOH | 1 | | | |

The most attractive products are of category AA or AB, namely of category A in terms of their gene expression on myostatin combined with a category A or B in terms of protein synthesis.

LITERATURE

Arounleut P, Bialek P, Liang L F, et al. 2013. A myostatin inhibitor (propeptide-Fc) increases muscle mass and muscle fiber size in aged mice but does not increase bone density or bone strength. *Exper Gerontol* 48:898-904.

Aubertin-Leheudre M, Lord C, Khalil A, Dionne I J. 2007. Six months of isoflavone supplement increases fat-free mass in obese-sarcopenic postmenopausal women: a randomized double-blind controlled trial. *Eur J Clin Nutr* 61:1442-1444.

Aussel C, Woelffle E, Lemoigne P, Depailler L, Bouillanne O. 2013. Une nouvelle strategie nutritionnelle pour lutter contre la denutrition et la sarcopenie: le regime proteique pulsé [A novel nutritional strategy for combating undernutritionment and sarcopenia: the pulsed protein diet]. *Cahiers Nutrition Dietetique* 48:33-40.

Azizov A P, Seifulla R D, Ankudinova I A, Kondrat'eva II, Borisova I G. 1998. Effect of the antioxidants elton and leveton on the physical work capacity of athletes. *Eksp Klin Farmakol* 61(1):60-62.

Baptista I L, Leal M L, Artioli G G, et al. 2010. Leucine attenuates skeletal muscle wasting via inhibition of ubiquitin ligases. *Muscle Nerve* 41(6):800-808.

Báthori M, Tóth N, Hunyadi A, Márki A, Zador E. (2008). Phytoecdysteroids and anabolic-androgenic steroids—Structure and effects on Humans. *Current Medicinal Chemistry* 15:75-91.

Bennett B T, Mohamed J S, Alway S E. 2013. Effects of resveratrol on the recovery of muscle mass following disuse in the plantaris muscle of aged rats. *PLoS One* 8(12):e83518.

Boirie Y, Gachon P, Beaufrere B. 1997. Splanchnic and whole body leucine kinetics in young and elderly men. *Am J Clin Nutr.* 65:489-495.

Bonnefoy M, Constans T, Ferry M. 2000. Dénutrition du sujet âgé. Influence de la nutrition et de l'activité physique sur le muscle au grand âge [Undernutritionment in the elderly. Influence of nutrition and physical activity on muscle in old age]. *Presse Med* 29:2177-2182.

Bonnefoy M. 2008. Interventions pour restaurer la masse musculaire chez le sujet âge [Interventions for restoring muscle mass in the elderly]. *Nutr Clin Metab* 22:80-83.

Buehring B, Binkley N. 2013. Myostatin—the holy grail for muscle, bone, and fat? *Curr Osteoporos Rep* 11(4):407-414.

Castan-Laurell I, Dray C, Knauf C, Kunduzova O, Valet P. 2012. Apelin, a promising target for type 2 diabetes treatment? *Trends Endocrinol Metab* 23(5):234-241.

Chermnykh N S, Shimanovsky N L, Shutko G V, Syrov V N. 1988. Effects of methandrostenolone and ecdysterone on physical endurance of animals and protein metabolism in the skeletal muscles. *Farmakologiya i Toksikologiya* 6: 57-62.

Coëffier M, Petit A, Dechelotte P. 2009. Quelle pharmaconutrition pour lutter contre la sarcopenie? [Which pharmaconutrition for combating sarcopenia?] *Nutrition Clinique Metabolisme* 23:76-79.

Collins-Hooper H, Sartori R, Macharia R, et al. 2014. Propeptide-mediated inhibition of myostatin increases muscle mass through inhibiting proteolytic pathways in aged mice. *J Gerontol A Biol Sci Med Sci*, doi:10.1093/gerona/gh170.

Crenn P. 2013. Sarcopénie et cachexie: approche médicamenteuse [Sarcopenia and cachexia: a drug approach]. *Nutrition Clinique Métabolisme* 27:69-73.

de Jager N, Hudson N J, Reverter A, et al. 2011. Chronic exposure to anabolic steroids induces the muscle expression of oxytocin and a more than fiftyfold increase in circulating oxytocin in cattle. *Physiol Genomics* 43:467-478.

Dumonceaux J, Marie S, Beley C, Trollet C, Vignaud A, Ferry A, Butler-Browne G, Garcia L. 2010. Combination of myostatin pathway interference and dystrophin rescue enhances tetanic and specific force in dystrophic mdx mice. *Mol Ther* 18(5): 881-887.

Fiatarone M A, Marks E C, Ryan N D, Meredith C N, Lipsitz L A, Evans W J. 1990. High-intensity strength training in nonagerians. *JAMA* 263: 3029-3034.

Foucault A S, Mathé V, Lafont R, Even P, Dioh W, Veillet S, Tomé D, Huneau D, Hermier D, Quignard-Boulangé A. 2012. Quinoa extract enriched in 20-hydroxyecdysone protects mice from diet-induced obesity and modulates adipokines expression. *Obesity* 20:270-277.

Foucault A S, Dioh W, Lafont R, Veillet S, Tomé D, Quignard-Boulangé A, Clément K, Rizkalla S. 2014. 20-Hydroxyecdysone increases android fat mass loss with no significant effect on muscle mass loss during a weight loss program in obese and overweight subjects. ICFSR 2014 International Conference of Frailty and Sarcopenia Research, Barcelona, 12-14, Mar. 2014.

Gadzhieva R M, Portugalov S N, Paniushkin V V, Kondrat'eva I I. 1995. A comparative study of the anabolic action of ecdysten, leveton and Prime Plus, preparations of plant origin. *Eksp Klin Farmakologiya* 58(5): 46-48.

Gilson H, Schakman O, Combaret L, et al. 2007. Myostatin gene deletion prevents glucocorticoid-induced muscle atrophy. *Endocrinology* 148:452-460.

Gorelick-Feldman J, MacLean D, Ilic N, Poulev A, Lila M A, Raskin I. 2008. Phytoecdysteroids increase protein synthesis in skeletal muscle cells. *J. Agric. Food Chem.* 56: 3532-3537.

Gorelick-Feldman J, Cohick W, Raskin I. 2010. Ecdysteroids elicit a rapid $Ca^{2+}$ flux leading to Akt activation and increased protein synthesis in skeletal muscle cells. *Steroids* 70: 632-637.

Greenberg S A. 2012. Pathogenesis and therapy of inclusion body myositis. *Curr Opin Neurol* 25(5): 630-639.

Han H Q, Mitch W E. 2011. Targeting the myostatin signaling pathway to treat muscle wasting diseases. *Curr Opin Support Palliat Care* 5(4):334-341.

Hung T J, Chen W M, Liu S F, et al. 2012. 20-Hydroxyecdysone attenuates TGF-β1-induced renal cellular fibrosis in proximal tubule cells. *J Diabetes Complications* 26(6):463-469.

Kazi A A, Lang C H 2010. PRAS40 Regulates Protein Synthesis and Cell Cycle in C2C12 Myoblasts *Mol Med.* 16(9-10):359-371.

Kizelsztein P, Govorko D, Komarnytsky S, Evans A, Wang Z, Cefalu W T, Raskin I. 2009. 20-Hydroxyecdysone decreases weight and hyperglycemia in a diet-induced obesity mice model. *Am. J. Physiol. Endocrinol. Metab.* 296:E433-E439.

Knight J D R, Kothary R. 2011. The myogenic kinome: protein kinases critical tomammalian skeletal myogenesis Skeletal Muscle, 1:29, www.skeletalmusclejournal.com/content/1/1/29

Lafont R, Clément K, Rizkalla S, Foucault A S, Veillet S, Dioh W. 2013 Phytoecdysones for use in weight stabilization after a weight-loss diet. PCT patent application WO 2013/068704

Lafont R, Harmatha J, Marion-Poll F, Dinan L, Wilson I D. 2002. Ecdybase, a free ecdysteroid database. ecdybase.org Larock R C. 1989. Comprehensive organic transformations: A guide to functional group preparations. VCH Publishers, New York.

Lawrence M M. 2012. *Ajuga turkestanica* as a countermeasure against sarcopenia and dynapenia. Ms thesis, Appalachian State University.

Le Grand F, Rudnicki M A. 2007. Skeletal muscle satellite cells and adult myogenesis. Curr Opin Cell Biol, 19:628-633.

Léger B, Derave W, De Bock K; Hespel P, Russell A P. 2008. Human sarcopenial reveals an increase in SOCS-3 and myostatin and a reduced efficiency of Akt phosphorylation. *Rejuvenation Res* 11(1):163-175.

Li Z, Heber D. 2011. Sarcopenic obesity in the elderly and strategies for weight management. *Nutrition Reviews* 70(1):57-64.

Li Z B, Kollias H D, Wagner K R. 2008. Myostatin directly regulates skeletal muscle fibrosis. *J. Biol. Chem.* 283(28): 19371-19378.

Little J P, Phillips S M. 2009. Resistance exercise and nutrition to counteract muscle wasting. *Appl Physiol Nutr Metab* 34:817-828.

Liu W, Thomas S G, Asa S L, et al. 2003. Myostatin is a skeletal muscle target of growth hormone anabolic action. *J Clin Endocr Metab* 88(11):5490-5496.

Macell T J, Harman S M, Urban R J, et al. 2001. Comparison of G H, IGF-I, and testosterone with mRNA of receptors and myostatin in skeletal muscle in older men. *Am J Physiol Endocrinol Metab* 281: E1159-E1164.

Murad M H, Elamin K B, Abu Elnour N O, et al. 2011. Clinical review: the effect of vitamin D on falls: a systematic review and meta-analysis. *J Clin Endocrinol Metab* 96(10):2997-3006.

Murphy K T, Koopman R, Naim T, et al. 2010. Antibody-directed myostatin inhibition in 21-mo-old mice reveals novel roles for myostatin signaling in skeletal muscle structure and function. *FASEB J* 24:4433-4442.

Pierno S, Tricarico D, Liantonio A, et al. 2014. An olive oil-derived antioxidant mixture ameliorates the age-related decline of skeletal muscle function. *AGE* 36:73-88.

Quillot D, Böhme P, Malgras P, Malgras A, Ziegler 0. 2013. L'obésité du sujet âgé [Obesity in the elderly]. *Nutr Clin Métabolisme* 27:95-101.

Ryall J G, Plant D R, Gregorevic P, Silence M N, Lynch G S. 2004. ß2-Agonist administration reverses muscle wasting and improves muscle function in aged rats. *J Physiol* 555(1):175-188.

Ryall J G, Church J E, Lynch G S. 2007. A novel role of ß-adrenoreceptor signalling in skeletal muscle growth, development and regeneration. *Proc Australian Physiol Soc* 40:103-108.

Ryan A S, Li G, Blumenthal J B, Ortmeyer H K. 2013. Aerobic exercise+weight loss decreases skeletal muscle myostatin expression and improves insulin sensitivity in older adults. *Obesity* 21(7): 1350-1356.

Sabourin L A, Rudnicki M A. 2000. The molecular regulation of myogenesis. *Clin Genet* 57:16-25. Saini A, Faulkner S, A L-Shanti N, Stewart C. 2009. Powerful signals for weak muscles. *Ageing Res Rev* 8:251-267.

Sakuma K, Yamaguchi A. 2012. Sarcopenia and age-related endocrine function. *Int J Endocrinol*, doi:10.1155/2012/127362.

Sattler F R. 2013. Growth hormone in the aging male. *Best Practice Res Clin Endocr Metab* 27:541-555.

Schaap L A, Pluijm S M F, Deeg D J H, et al. 2009. Higher inflammatory marker levels in older persons: associations with 5-year change in muscle mass and muscle strength. *J Gerontol A Biol Sci Med Sci* 64A(11):1183-1189.

Seidlova-Wuttke D, Erhardt C, Wuttke W. 2010. Metabolic effects of 20-OH ecdysone in ovariectomized rats. *J Steroid Biochem Mol Biol* 119:121-126.

Seidman S N. 2007. Androgens and the aging male. *Psychopharmacol Bull* 40:205-218.

Shadfar S, Couch M E, McKinney K A, et al. 2011. Oral resveratrol therapy inhibits cancer-induced skeletal muscle and cardiac atrophy in vivo. *Nutr Cancer* 63(5): 749-762.

Simakin S Yu, Panyushkin V V, Portugalov S N, Kostina L V, Martisorov E G. 1988. Combined application of preparation Ecdysten and product Bodrost during training in cyclic sports. *Sports Science Bulletin No* 2, 29-31.

Stenholm S, Alley D, Bandinelli S, et al. 2009. The effect of obesity combined with low muscle strength on decline in mobility in older persons: results from the InCHIANTI study. *Int J Obesity* 33:635-644.

Syrov V N. 2000. Comparative experimental investigations of the anabolic activity of ecdysteroids and steranabols. *Pharm Chem Journal* 34(4):193-197.

Syrov V N, Saatov V, Sagdullaev ShSh, Mamatkhanov A U. (2001). Study of the structure—anabolic activity relationship for the phytoecdysteroids extracted from some plants of central Asia. *Pharmaceutical Chemistry Journal* 35: 667-671.

Tchoukouegno Ngueu S. 2013. Estrogenic, cytotoxic and anabolic effects on estrogen target organs of an extract of *Erythrina excelsa* and ecdysterone. PhD thesis, German Sports University of Cologne.

Tisdale M J. 2001. Facteurs lipolytiques et protéolytiques de la cachexie cancéreuse [Lipolytic and proteolytic factors of cancer-related cachexia]. *Nutr Clin Métabol* 15:266-272.

Todorov I N, Mitrokhin YuI, Efremova O I, Sidorenko L I. 2000. The effect of ecdysterone on the biosynthesis of proteins and nucleic acids in mice. *Pharmaceut Chem J* 34(9):455-458.

Tóth N, Szabó A, Kacsala P, Héger J, Zádor E. 2008. 20-Hydroxyecdysone increases fiber size in a muscle-specific fashion in rat. *Phytomedicine* 15:691-698.

Verghese J, Holtzer R, Oh-Park M, et al. 2011. Inflammatory markers and gait speed decline in older adults. *J Gerontol A Biol Sci Med Sci* 66A:1083-1089.

Walston J D. 2012. Sarcopenia in older adults. *Curr. Opinion Rheumatol.* 24:623-627.

White J P, Gao S, Puppa M J, et al. 2013. Testosterone regulation of Akt/mTORC1/FoxO3a signaling in skeletal muscle. *Mol Cell Endocrinol* 365:174-186.

White T A, LeBrasseur, N K. 2014. Myostatin and sarcopenia: opportunities and challenges—a mini-review. *Gerontology*, doi:10.1159/000356740.

Wuttke W, Seidlová-Wuttke D. 2013. Pflanzliche Präparate für die Therapie klimaterischer und postmenopausaler Beschwerden und Erkrankungen. *Frauenartz* 54:580-587.

Zhao J, Brault J J, Schild A, Goldberg A L. 2008. Coordinate activation of autophagy and the proteasome pathway by FoxO transcription factor. *Autophagy* 4(3):378-380.

Zhu W M, Zhu H J, Tian W S, Hao X J, Pittman Jr C U. 2002. The selective dehydroxylation of 20-hydroxyecdysone by Zn powder and anhydrous acetic acid. *Synthetic Communications* 32:1385-1391.

Zubeldia J M, Hernández-Santana A, Jiménez-de-Rio M, et al. 2012. In vitro characterization of the efficacy and safety profile of a proprietary *Ajuga turkestanica* extract. *Chinese Medicine* 3:215-222.

The invention claimed is:
1. A compound of formula (I) below:

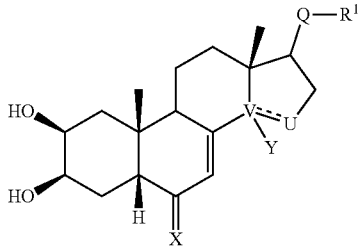

(I)

wherein:
V—U is a carbon-carbon single bond and Y is a hydroxyl group or a hydrogen, or V—U is a C═C ethylenic bond;
X is chosen from: an oxygen, an N—OR$^5$ group,
R$^5$ then being chosen from: a hydrogen; a C$_1$-C$_6$ alkyl group optionally having unsaturations on the chain; a (C$_1$-C$_6$)CO$_2$R$^6$ group with R$^6$ possibly being a hydrogen or a C$_1$-C$_6$ group; a (C$_1$-C$_6$)OR$^7$ group, R$^7$ being an aromatic or heteroaromatic ring optionally monosubstituted or polysubstituted with an alkyl or alkoxyl group, CF$_3$, Cl; a (C$_1$-C$_6$)NR$^8$R$^9$ group, R$^8$ and R$^9$ being C$_1$-C$_6$ groups, or (C$_1$-C$_6$)N(C$_1$-C$_6$) groups or (C$_1$-C$_6$)N(C$_1$-C$_6$)OR$^6$ groups with R$^6$ as defined above, NR$^8$R$^9$ can also be a heterocycle; and wherein:
Q is chosen from: a C═NOR$^5$ group, R$^5$ being defined as above; a CHNR$^2$R$^3$ group,
with R$^1$ being a (C$_1$-C$_6$) alkyl group;
with R$^2$ and R$^3$, which may be identical or different, each chosen from: a hydrogen atom; a (C$_1$-C$_6$) alkyl group; a (C$_1$-C$_6$)W(C$_1$-C$_6$) group; a cycloalkyl group; a (C$_1$-C$_6$)CHF$_2$ group; a (C$_1$-C$_6$)A group with A representing a heterocycle defined as above; a group of COR$^4$ type,
R$^4$ being chosen from: an optionally unsaturated (C$_1$-C$_6$) alkyl or cycloalkyl group; a heterocyclic group of A type as defined above, an aromatic or heteroaromatic group optionally substituted with a group of the type OH, OMe, (C$_1$-C$_6$), N(C$_1$-C$_6$), CO$_2$(C$_1$-C$_6$), CF$_3$, OCF$_3$, CN, Cl, F; a (C$_1$-C$_6$)W(C$_1$-C$_6$) group;
W being a heteroatom chosen from N, O and S; and
the compound being in the form of an enantiomer, a diastereoisomer, a hydrate, a solvate, a tautomer, a racemic mixture or a pharmaceutically acceptable salt.

2. The compound as claimed in claim 1, wherein, in formula (I), Q represents a C═NOR$^5$ group.

3. The compound as claimed in claim 2, wherein, in formula (I):
X is an oxygen;
V—U is a carbon-carbon single bond;
Y is a hydroxyl group; and
R$^1$ is a methyl group.

4. The compound as claimed in claim 1, wherein, in formula (I), Q represents a CHNR$^2$R$^3$ group, with R$^2$ and R$^3$, which may be identical or different, each being chosen from: a hydrogen atom; a (C$_1$-C$_6$) alkyl group; a (C$_1$-C$_6$)W(C$_1$-C$_6$) group; a cycloalkyl group; a (C$_1$-C$_6$)CHF$_2$ group; a (C$_1$-C$_6$)A group with A representing a heterocycle defined as above; a group of COR$^4$ type, R$^4$ being chosen from: an optionally unsaturated (C$_1$-C$_6$) alkyl or cycloalkyl group; a heterocyclic group of A type as defined above, an aromatic or heteroaromatic group optionally substituted with a group of the type OH, OMe, (C$_1$-C$_6$), N(C$_1$-C$_6$), CO$_2$(C$_1$-C$_6$), CF$_3$, OCF$_3$, CN, Cl, F; a (C$_1$-C$_6$)W(C$_1$-C$_6$) group.

5. The compound as claimed in claim 4, wherein, in formula (I):
X is an oxygen;
V—U is a carbon-carbon single bond;
Y is a hydroxyl group;
R$^1$ is a methyl group; and
W is a heteroatom chosen from N, O and S.

6. The compound as claimed in claim 1, wherein, in formula (I), V—U is a C═C ethylenic bond.

7. The compound as claimed in claim 1, wherein, in formula (I), X is an N—OR$^5$ group.

8. The compound as claimed in any one of claims 1 to 7, chosen from the following compounds:
No. 28: (2S,3R,5R,10R,13R,14S,17S)-17-(N-but-3-enoxy-C-methyl-carbonimidoyl)-2,3,14-trihydroxy-10,13-dimethyl-2,3,4,5,9,11,12,15,16,17-decahydro-1H-cyclopenta[a]phenanthren-6-one;
No. 32: (2S,3R,5R,10R,13R,14S,17S)-17-(N-(2-diethylaminoethoxy)-C-methyl-carbonimidoyl)-2,3,14-trihydroxy-10,13-dimethyl-2,3,4,5,9,11,12,15,16,17-decahydro-1H-cyclopenta[a]phenanthren-6-one;
No. 41: 2-methoxy-N-(2-methoxyethyl)-N[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]acetamide;
No. 42: (2S,3R,5R,10R,13R,14S,17S)-2,3,14-trihydroxy-17-[1-(2-methoxyethylamino)ethyl]-10,13-dimethyl-2,3,4,5,9,11,12,15,16,17-decahydro-1H-cyclopenta[a]phenanthren-6-one;
No. 43: (2S,3R,5R,10R,13R,14S,17S)-2,3,14-trihydroxy-10,13-dimethyl-17-[1-(3-pyridylmethylamino)ethyl]-2,3,4,5,9,11,12,15,16,17-decahydro-1H-cyclopenta[a]phenanthren-6-one;
No. 46: (2S,3R,5R,10R,13R,14S,17S)-2,3,14-trihydroxy-10,13-dimethyl-17-[1-(tetrahydrofuran-2-ylmethylamino)ethyl]-2,3,4,5,9,11,12,15,16,17-decahydro-1H-cyclopenta[a]phenanthren-6-one;
No. 51: 2-ethyl-N-(2-methoxyethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]butanamide;
No. 62: 2-methoxy-N-(tetrahydrofuran-2-ylmethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]acetamide;
No. 63: N-(tetratetrahydrofuran-2-ylmethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]furan-2-carboxamide;
No. 67: N-(2,2-difluoroethyl)-N-[1-[(2S,3R,5R,10R,13R,14S,17S)-2,3,14-trihydroxy-10,13-dimethyl-6-oxo-2,3,4,5,9,11,12,15,16,17-decahydro-1H-cyclopenta[a]phenanthren-17-yl]ethyl]furan-2-carboxamide; and
No. 76: (2S,3R,5R,10R,13R,14S,17S)-2,3,14-trihydroxy-17-[1-(2-methoxyethyl(methyl)amino)ethyl]-10,13-dimethyl-2,3,4,5,9,11,12,15,16,17-decahydro-1H-cyclopenta[a]phenanthren-6-one.

9. A pharmaceutical composition comprising the compound as claimed in claim 1 and a pharmaceutically acceptable carrier.

10. A method of treating sarcopenia and associated complications or pathological conditions thereof using the chemical compound as claimed in claim 1.

11. The method as claimed in claim 10 for treating loss of strength, loss of muscle mass, loss of physical performance and capacity, and loss of mobility in mammals.

12. A method of treating sarcopenic obesity and associated complications or pathological conditions thereof using the chemical compound as claimed in claim 1.

13. The method as claimed in claim 12 for treating loss of strength, loss of muscle mass, loss of physical performance and capacity, and loss of mobility in mammals.

14. A method of treating obesity and associated complications or pathological conditions thereof using the chemical compound as claimed in claim 1.

15. The method as claimed in claim 14 for treating type 2 diabetes or metabolic syndrome in mammals.

* * * * *